US008565475B2

(12) United States Patent
Moon et al.

(10) Patent No.: US 8,565,475 B2
(45) Date of Patent: *Oct. 22, 2013

(54) OPTICAL SYSTEM AND METHOD FOR READING ENCODED MICROBEADS

(75) Inventors: John A. Moon, San Diego, CA (US); Martin A. Putnam, Cheshire, CT (US)

(73) Assignee: Illumina, Inc., San Diego, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/243,422

(22) Filed: Sep. 23, 2011

(65) Prior Publication Data

US 2012/0074225 A1 Mar. 29, 2012

Related U.S. Application Data

(63) Continuation of application No. 11/281,907, filed on Nov. 16, 2005, now Pat. No. 8,081,792, which is a continuation-in-part of application No. 10/645,689, filed on Aug. 20, 2003, now abandoned, and a continuation-in-part of application No. 10/661,234, filed on Sep. 12, 2003, now Pat. No. 7,106,513.

(60) Provisional application No. 60/628,897, filed on Nov. 16, 2004.

(51) Int. Cl.
*G06K 9/00* (2006.01)
*G06K 5/00* (2006.01)

(52) U.S. Cl.
USPC .......................... 382/100; 235/380; 356/601

(58) Field of Classification Search
None
See application file for complete search history.

(56) References Cited

U.S. PATENT DOCUMENTS

| 3,074,634 A | 1/1963 | Gamo |
| 3,600,223 A | 8/1971 | Glick et al. |
| 3,614,193 A | 10/1971 | Beiser |
| 3,791,788 A | 2/1974 | Taylor |
| 3,858,979 A | 1/1975 | Elbe |
| 3,880,497 A | 4/1975 | Bryngdahl |
| 3,891,302 A | 6/1975 | Dabby |
| 3,903,415 A | 9/1975 | Holzapfel |

(Continued)

FOREIGN PATENT DOCUMENTS

| CH | 598661 | 5/1978 |
| DE | 2416652 | 10/1975 |

(Continued)

OTHER PUBLICATIONS

"Compact Disc Arrayer"; V&P Scientific; Nov. 17, 2003; pp. 1-4.

(Continued)

*Primary Examiner* — Wenpeng Chen
(74) *Attorney, Agent, or Firm* — The Small Patent Law Group LLC; Dean D. Small; Jason P. Gross

(57) ABSTRACT

An optical system for reading encoded microbeads. The microbeads provide output light signals onto a Fourier plane when illuminated by an incident light. The system includes an input light source that is configured to illuminate the microbeads thereby providing the output light signals. The output light signals are configured to be projected onto the Fourier plane in a readable manner. The system also includes a reading device that is positioned to detect the output light signals from the Fourier plane. The system also includes a processor that is configured to perform Fourier plane analysis of the optical light signals to determine corresponding codes of the microbeads.

22 Claims, 36 Drawing Sheets

(56) References Cited

U.S. PATENT DOCUMENTS

| | | |
|---|---|---|
| 3,916,182 A | 10/1975 | Dabby |
| 3,928,253 A | 12/1975 | Thornton |
| 3,968,476 A | 7/1976 | McMahon |
| 4,011,435 A | 3/1977 | Phelps |
| 4,023,010 A | 5/1977 | Horst |
| 4,053,228 A | 10/1977 | Schiller |
| 4,053,433 A | 10/1977 | Lee |
| 4,112,037 A | 9/1978 | Parker |
| 4,131,337 A | 12/1978 | Moraw |
| 4,168,146 A | 9/1979 | Grubb |
| 4,301,139 A | 11/1981 | Feingers |
| 4,386,274 A | 5/1983 | Altshuler |
| 4,400,616 A | 8/1983 | Chevillat |
| 4,445,229 A | 4/1984 | Tasto |
| 4,447,546 A | 5/1984 | Hirschfeld |
| 4,537,504 A | 8/1985 | Baltes |
| 4,560,881 A | 12/1985 | Briggs |
| 4,562,157 A | 12/1985 | Lowe |
| 4,647,544 A | 3/1987 | Nicoli |
| 4,678,752 A | 7/1987 | Thorne |
| 4,685,480 A | 8/1987 | Eck |
| 4,688,240 A | 8/1987 | Hosemann |
| 4,690,907 A | 9/1987 | Hibino |
| 4,701,754 A | 10/1987 | Provonchee |
| 4,716,121 A | 12/1987 | Block |
| 4,725,110 A | 2/1988 | Glenn |
| 4,740,468 A | 4/1988 | Weng |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A | 9/1988 | Carveth et al. |
| 4,807,950 A | 2/1989 | Glenn |
| 4,815,027 A | 3/1989 | Tokumitsu |
| 4,816,659 A | 3/1989 | Bianco |
| 4,820,006 A | 4/1989 | Constant |
| 4,822,746 A | 4/1989 | Walt |
| 4,841,140 A | 6/1989 | Sullivan |
| 4,843,631 A | 6/1989 | Steinpichler |
| 4,877,747 A | 10/1989 | Stewart |
| 4,880,752 A | 11/1989 | Keck |
| 4,882,288 A | 11/1989 | North |
| 4,921,805 A | 5/1990 | Gebeyehu |
| 4,931,384 A | 6/1990 | Layton |
| 4,937,048 A | 6/1990 | Sakai |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason |
| RE33,581 E | 4/1991 | Nicoli |
| 5,028,545 A | 7/1991 | Soini |
| 5,030,558 A | 7/1991 | Litman |
| 5,033,826 A | 7/1991 | Kolner |
| 5,048,139 A | 9/1991 | Matsumi et al. |
| 5,065,008 A | 11/1991 | Hakamata |
| 5,067,155 A | 11/1991 | Bianco |
| 5,081,012 A | 1/1992 | Flanagan |
| 5,089,387 A | 2/1992 | Tsay |
| 5,090,807 A | 2/1992 | Tai |
| 5,091,636 A | 2/1992 | Takada |
| 5,095,194 A | 3/1992 | Barbanell |
| 5,100,238 A | 3/1992 | Nailor |
| 5,104,209 A | 4/1992 | Hill |
| 5,105,305 A | 4/1992 | Betzig |
| 5,114,864 A | 5/1992 | Walt |
| 5,115,121 A | 5/1992 | Bianco |
| 5,118,608 A | 6/1992 | Layton |
| 5,129,974 A | 7/1992 | Aurenius |
| 5,138,468 A | 8/1992 | Barbanell |
| 5,141,848 A | 8/1992 | Donovan |
| 5,143,853 A | 9/1992 | Walt |
| 5,144,461 A | 9/1992 | Horan |
| 5,160,701 A | 11/1992 | Brown, III |
| 5,166,813 A | 11/1992 | Metz |
| 5,192,980 A | 3/1993 | Dixon |
| 5,196,350 A | 3/1993 | Backman |
| 5,200,794 A | 4/1993 | Nishiguma |
| 5,218,594 A | 6/1993 | Tanno |
| 5,239,178 A | 8/1993 | Derndinger |
| 5,244,636 A | 9/1993 | Walt |
| 5,283,777 A | 2/1994 | Tanno |
| 5,291,006 A | 3/1994 | Nishiguma |
| 5,291,027 A | 3/1994 | Kita |
| 5,300,764 A | 4/1994 | Hoshino |
| 5,307,332 A | 4/1994 | Tinet |
| 5,310,686 A | 5/1994 | Sawyers |
| 5,329,352 A | 7/1994 | Jacobsen |
| 5,342,790 A | 8/1994 | Levine |
| 5,349,442 A | 9/1994 | Deason |
| 5,352,582 A | 10/1994 | Lichtenwalter |
| 5,364,797 A | 11/1994 | Olson |
| 5,367,588 A | 11/1994 | Hill |
| 5,372,783 A | 12/1994 | Lackie |
| 5,374,816 A | 12/1994 | Bianco |
| 5,374,818 A | 12/1994 | Bianco |
| 5,388,173 A | 2/1995 | Glenn |
| 5,394,234 A | 2/1995 | Bianco |
| 5,395,558 A | 3/1995 | Tsai |
| 5,410,147 A | 4/1995 | Riza |
| 5,426,297 A | 6/1995 | Dunphy |
| 5,432,329 A | 7/1995 | Colgate |
| 5,442,433 A | 8/1995 | Hoshino |
| 5,448,659 A | 9/1995 | Tsutsui |
| 5,451,528 A | 9/1995 | Raymoure |
| 5,455,178 A | 10/1995 | Fattinger |
| 5,461,475 A | 10/1995 | Lerner |
| 5,465,176 A | 11/1995 | Bianco |
| 5,468,649 A | 11/1995 | Shah |
| 5,472,515 A | 12/1995 | Roberts et al. |
| 5,479,515 A | 12/1995 | Longacre |
| 5,506,674 A | 4/1996 | Inoue |
| 5,514,785 A | 5/1996 | Van Ness |
| 5,528,045 A | 6/1996 | Hoffman |
| 5,547,849 A | 8/1996 | Baer |
| 5,559,613 A | 9/1996 | Deveaud-Pledran |
| 5,585,639 A | 12/1996 | Dorsel |
| 5,587,832 A | 12/1996 | Krause |
| 5,607,188 A | 3/1997 | Bahns |
| 5,610,287 A | 3/1997 | Nikiforov |
| 5,620,853 A | 4/1997 | Smethers |
| 5,621,515 A | 4/1997 | Hoshino |
| 5,624,850 A | 4/1997 | Kumar |
| 5,625,472 A | 4/1997 | Mizrahi |
| 5,627,040 A | 5/1997 | Bierre |
| 5,627,663 A | 5/1997 | Horan |
| 5,633,724 A | 5/1997 | King |
| 5,633,975 A | 5/1997 | Gary |
| 5,663,790 A | 9/1997 | Ekstrom |
| 5,667,976 A | 9/1997 | Van Ness |
| 5,671,308 A | 9/1997 | Inoue |
| 5,682,064 A | 10/1997 | Atkins |
| 5,700,037 A | 12/1997 | Keller |
| 5,712,912 A | 1/1998 | Tomko |
| 5,717,488 A * | 2/1998 | Watanabe ............. 356/499 |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins |
| 5,745,617 A | 4/1998 | Starodubov |
| 5,759,778 A | 6/1998 | Li |
| 5,760,961 A | 6/1998 | Tompkin |
| 5,766,956 A | 6/1998 | Groger |
| 5,771,251 A | 6/1998 | Kringlebotn |
| 5,776,694 A | 7/1998 | Sheiness |
| 5,793,502 A | 8/1998 | Bianco |
| 5,798,273 A | 8/1998 | Shuler |
| 5,799,231 A | 8/1998 | Gates |
| 5,801,857 A | 9/1998 | Heckenkamp |
| 5,804,384 A | 9/1998 | Muller |
| 5,812,272 A | 9/1998 | King |
| 5,822,472 A | 10/1998 | Danielzik |
| 5,824,478 A | 10/1998 | Muller |
| 5,824,557 A | 10/1998 | Burke |

(56) References Cited

U.S. PATENT DOCUMENTS

| | | |
|---|---|---|
| 5,830,622 A | 11/1998 | Canning |
| 5,831,698 A | 11/1998 | Depp |
| 5,837,475 A | 11/1998 | Dorsel |
| 5,837,552 A | 11/1998 | Cotton |
| 5,841,555 A | 11/1998 | Bianco |
| 5,846,737 A | 12/1998 | Kang |
| 5,861,113 A | 1/1999 | Choquette et al. |
| 5,874,187 A | 2/1999 | Colvin |
| 5,881,197 A | 3/1999 | Dong |
| 5,895,750 A | 4/1999 | Mushahwar |
| 5,922,550 A | 7/1999 | Everhart |
| 5,922,617 A | 7/1999 | Wang |
| 5,925,562 A | 7/1999 | Nova |
| 5,925,878 A | 7/1999 | Challener |
| 5,945,679 A | 8/1999 | Dorsel |
| 5,972,542 A | 10/1999 | Starodubov |
| 5,976,896 A | 11/1999 | Kumar |
| 5,981,166 A | 11/1999 | Mandecki |
| 5,986,838 A | 11/1999 | Thomas, III |
| 5,989,923 A | 11/1999 | Lowe |
| 5,992,742 A | 11/1999 | Sullivan |
| 5,998,796 A | 12/1999 | Liu |
| 6,001,510 A | 12/1999 | Meng |
| 6,005,691 A | 12/1999 | Grot |
| 6,017,754 A | 1/2000 | Chesnut |
| 6,025,129 A | 2/2000 | Nova |
| 6,025,283 A | 2/2000 | Robers |
| 6,027,694 A | 2/2000 | Boulton |
| 6,030,581 A | 2/2000 | Virtanen |
| 6,035,082 A | 3/2000 | Murphy |
| 6,035,083 A | 3/2000 | Brennan |
| 6,036,807 A | 3/2000 | Brongers |
| 6,043,880 A | 3/2000 | Andrews |
| 6,046,925 A | 4/2000 | Tsien |
| 6,049,727 A | 4/2000 | Crothall |
| 6,057,107 A | 5/2000 | Fulton |
| 6,060,256 A | 5/2000 | Everhart |
| 6,067,167 A | 5/2000 | Atkinson |
| 6,067,392 A | 5/2000 | Wakami |
| 6,078,048 A | 6/2000 | Stevens |
| 6,084,995 A | 7/2000 | Clements |
| 6,087,186 A | 7/2000 | Cargill |
| 6,088,503 A | 7/2000 | Chandler |
| 6,096,496 A | 8/2000 | Frankel |
| 6,096,596 A | 8/2000 | Gonzalez |
| 6,097,485 A | 8/2000 | Lievan |
| 6,103,535 A | 8/2000 | Pilevar |
| 6,118,127 A | 9/2000 | Liu |
| 6,128,077 A | 10/2000 | Jovin |
| 6,137,931 A | 10/2000 | Ishikawa |
| 6,143,247 A | 11/2000 | Sheppard, Jr. |
| 6,156,501 A | 12/2000 | McGall |
| 6,159,748 A | 12/2000 | Hechinger |
| 6,160,240 A | 12/2000 | Momma |
| 6,160,656 A | 12/2000 | Mossberg |
| 6,164,548 A | 12/2000 | Curiel |
| 6,165,592 A | 12/2000 | Berger |
| 6,165,648 A | 12/2000 | Covin |
| 6,174,648 B1 | 1/2001 | Terao |
| 6,194,563 B1 | 2/2001 | Cruickshank |
| 6,204,068 B1 | 3/2001 | Soini et al. |
| 6,204,969 B1 | 3/2001 | Jang |
| 6,214,560 B1 | 4/2001 | Yguerabide |
| 6,218,194 B1 | 4/2001 | Lyndin |
| 6,221,579 B1 | 4/2001 | Everhart |
| 6,229,635 B1 | 5/2001 | Wulf |
| 6,229,827 B1 | 5/2001 | Fernald |
| 6,229,941 B1 | 5/2001 | Yoon |
| 6,242,056 B1 | 6/2001 | Spencer |
| 6,259,450 B1 | 7/2001 | Chiabrera |
| 6,262,846 B1 | 7/2001 | Nakai |
| 6,268,128 B1 | 7/2001 | Collins |
| 6,277,628 B1 | 8/2001 | Johann |
| 6,284,437 B1 | 9/2001 | Kashyap |
| 6,284,459 B1 | 9/2001 | Nova |
| 6,285,806 B1 | 9/2001 | Kersey |
| 6,288,220 B1 | 9/2001 | Kambara |
| 6,292,282 B1 | 9/2001 | Mossberg |
| 6,292,319 B1 | 9/2001 | Thomas, III |
| 6,301,047 B1 | 10/2001 | Hoshino |
| 6,304,263 B1 | 10/2001 | Chiabrera |
| 6,306,587 B1 | 10/2001 | Royer |
| 6,309,601 B1 | 10/2001 | Juncosa |
| 6,312,961 B1 | 11/2001 | Voirin |
| 6,313,771 B1 | 11/2001 | Munroe |
| 6,314,220 B1 | 11/2001 | Mossberg |
| 6,319,668 B1 | 11/2001 | Nova |
| 6,321,007 B1 | 11/2001 | Sanders |
| 6,322,932 B1 | 11/2001 | Colvin |
| RE37,473 E | 12/2001 | Challener |
| 6,328,209 B1 | 12/2001 | O'Boyle |
| 6,329,963 B1 | 12/2001 | Chiabrera |
| 6,331,273 B1 | 12/2001 | Nova |
| 6,335,824 B1 | 1/2002 | Overbeck |
| 6,340,588 B1 | 1/2002 | Nova |
| 6,344,298 B1 | 2/2002 | Starodubov |
| 6,352,854 B1 | 3/2002 | Nova |
| 6,355,198 B1 | 3/2002 | Kim |
| 6,355,432 B1 | 3/2002 | Fodor |
| 6,356,681 B1 | 3/2002 | Chen |
| 6,359,734 B1 | 3/2002 | Staub |
| 6,361,958 B1 | 3/2002 | Shieh |
| 6,363,097 B1 | 3/2002 | Linke |
| 6,371,370 B2 | 4/2002 | Sadler |
| 6,372,428 B1 | 4/2002 | Nova |
| 6,383,754 B1 | 5/2002 | Kaufman |
| 6,391,562 B2 | 5/2002 | Kambara |
| 6,395,558 B1 | 5/2002 | Duveneck |
| 6,399,295 B1 | 6/2002 | Kaylor |
| 6,399,935 B1 | 6/2002 | Jovin |
| 6,403,320 B1 | 6/2002 | Read |
| 6,406,841 B1 | 6/2002 | Lee |
| 6,406,848 B1 | 6/2002 | Bridgham |
| 6,416,714 B1 | 7/2002 | Nova |
| 6,416,952 B1 | 7/2002 | Pirrung |
| 6,417,010 B1 | 7/2002 | Cargill |
| 6,424,056 B1 | 7/2002 | Irvin |
| 6,428,707 B1 | 8/2002 | Berger |
| 6,428,957 B1 | 8/2002 | Delenstarr |
| 6,429,022 B1 | 8/2002 | Kunz |
| 6,433,849 B1 | 8/2002 | Lowe |
| 6,436,651 B1 | 8/2002 | Everhart |
| 6,440,667 B1 | 8/2002 | Fodor |
| 6,456,762 B1 | 9/2002 | Nishiki |
| RE37,891 E | 10/2002 | Collins |
| 6,462,770 B1 | 10/2002 | Cline |
| 6,489,606 B1 | 12/2002 | Kersey |
| 6,496,287 B1 | 12/2002 | Seiberle |
| 6,506,342 B1 | 1/2003 | Frankel |
| 6,514,767 B1 | 2/2003 | Natan |
| 6,515,753 B2 | 2/2003 | Maher |
| 6,522,406 B1 | 2/2003 | Rovira |
| 6,522,809 B1 | 2/2003 | Takabayashi et al. |
| 6,524,793 B1 | 2/2003 | Chandler |
| 6,533,183 B2 | 3/2003 | Aasmul |
| 6,542,673 B1 | 4/2003 | Holter |
| 6,544,739 B1 | 4/2003 | Fodor |
| 6,545,758 B1 | 4/2003 | Sandstrom |
| 6,552,809 B1 | 4/2003 | Bergeron |
| 6,560,017 B1 | 5/2003 | Bianco |
| 6,565,770 B1 | 5/2003 | Mayer |
| 6,573,523 B1 | 6/2003 | Long |
| 6,576,424 B2 | 6/2003 | Fodor |
| 6,578,712 B2 | 6/2003 | Lawandy |
| 6,592,036 B2 | 7/2003 | Sadler |
| 6,594,421 B1 | 7/2003 | Johnson |
| 6,609,728 B1 | 8/2003 | Voermann |
| 6,613,581 B1 | 9/2003 | Wada |
| 6,618,342 B1 | 9/2003 | Johnson |
| 6,622,916 B1 | 9/2003 | Bianco |
| 6,628,439 B2 | 9/2003 | Shiozawa |
| 6,632,655 B1 | 10/2003 | Mehta |
| 6,635,470 B1 | 10/2003 | Vann |
| 6,635,863 B1 | 10/2003 | Nihommori |

(56) References Cited

U.S. PATENT DOCUMENTS

| | | |
|---|---|---|
| 6,646,243 B2 | 11/2003 | Pirrung |
| 6,657,758 B1 | 12/2003 | Garner |
| 6,660,147 B1 | 12/2003 | Woudenberg |
| 6,678,429 B2 | 1/2004 | Mossberg |
| RE38,430 E | 2/2004 | Rosenstein |
| 6,689,316 B1 | 2/2004 | Blyth |
| 6,692,031 B2 | 2/2004 | McGrew |
| 6,692,912 B1 | 2/2004 | Boles |
| 6,708,618 B1 | 3/2004 | Tsai |
| 6,750,941 B2 | 6/2004 | Satoh et al. |
| 6,762,061 B1 | 7/2004 | Borelli |
| 6,794,658 B2 | 9/2004 | MacAulay |
| 6,806,954 B2 | 10/2004 | Sandstrom |
| 6,858,184 B2 | 2/2005 | Pelrine |
| 6,874,639 B2 | 4/2005 | Lawandy |
| 6,881,789 B2 | 4/2005 | Bosse |
| 6,892,001 B2 | 5/2005 | Ohta |
| 6,905,885 B2 | 6/2005 | Colston |
| 6,908,737 B2 | 6/2005 | Ravkin |
| 6,919,009 B2 | 7/2005 | Stonas |
| 6,972,883 B2 | 12/2005 | Fujii |
| 6,982,996 B1 | 1/2006 | Putnam |
| 7,014,815 B1 | 3/2006 | Worthington |
| 7,045,049 B1 | 5/2006 | Natan |
| 7,065,032 B2 | 6/2006 | Horimai |
| 7,080,857 B2 | 7/2006 | Patton |
| 7,092,160 B2 * | 8/2006 | Putnam et al. ............ 359/566 |
| 7,106,513 B2 | 9/2006 | Moon |
| 7,122,384 B2 | 10/2006 | Prober |
| 7,126,755 B2 | 10/2006 | Moon |
| 7,164,533 B2 | 1/2007 | Moon |
| 7,190,522 B2 | 3/2007 | Moon |
| 7,215,628 B2 | 5/2007 | Horimai |
| 7,225,082 B1 | 5/2007 | Natan |
| 7,269,550 B2 * | 9/2007 | Tsushima et al. ........... 704/205 |
| 7,321,541 B2 | 1/2008 | Horimai |
| 7,339,148 B2 | 3/2008 | Kawano |
| 7,349,158 B2 | 3/2008 | Moon |
| 7,375,890 B2 * | 5/2008 | Putnam et al. ............ 359/566 |
| 7,399,643 B2 | 7/2008 | Moon et al. |
| 7,433,123 B2 | 10/2008 | Putnam et al. |
| 7,441,703 B2 | 10/2008 | Moon |
| 7,508,608 B2 | 3/2009 | Kersey et al. |
| 7,602,952 B2 | 10/2009 | Kersey |
| 7,604,173 B2 | 10/2009 | Kersey et al. |
| 7,619,819 B2 | 11/2009 | Moon et al. |
| 7,623,624 B2 | 11/2009 | Moon |
| 7,659,983 B2 | 2/2010 | Moon et al. |
| 7,791,802 B2 | 9/2010 | Putnam |
| 7,796,333 B2 | 9/2010 | Kersey |
| 2001/0007775 A1 | 7/2001 | Seul |
| 2001/0020375 A1 | 9/2001 | Novack |
| 2001/0029049 A1 | 10/2001 | Walt |
| 2002/0000471 A1 | 1/2002 | Aasmul |
| 2002/0006664 A1 | 1/2002 | Sabatini |
| 2002/0018430 A1 | 2/2002 | Heckenkamp |
| 2002/0021003 A1 | 2/2002 | McGrew |
| 2002/0022273 A1 | 2/2002 | Empedocles |
| 2002/0025534 A1 | 2/2002 | Goh |
| 2002/0031783 A1 | 3/2002 | Empedocles |
| 2002/0034747 A1 | 3/2002 | Bruchez |
| 2002/0039728 A1 | 4/2002 | Kain |
| 2002/0039732 A1 | 4/2002 | Bruchez |
| 2002/0074513 A1 | 6/2002 | Abel |
| 2002/0084329 A1 | 7/2002 | Kaye |
| 2002/0090650 A1 | 7/2002 | Empedocles |
| 2002/0094528 A1 | 7/2002 | Salafsky |
| 2002/0097658 A1 | 7/2002 | Worthington |
| 2002/0155490 A1 | 10/2002 | Skinner |
| 2002/0155507 A1 * | 10/2002 | Bruchez et al. ............ 435/7.2 |
| 2002/0174918 A1 | 11/2002 | Fujimura et al. |
| 2002/0197456 A1 | 12/2002 | Pope |
| 2003/0008323 A1 | 1/2003 | Ravkin |
| 2003/0021003 A1 | 1/2003 | Ono |
| 2003/0032203 A1 | 2/2003 | Sabatini |
| 2003/0077038 A1 | 4/2003 | Murashima |
| 2003/0082568 A1 | 5/2003 | Phan |
| 2003/0082587 A1 | 5/2003 | Seul |
| 2003/0129654 A1 | 7/2003 | Ravkin |
| 2003/0138208 A1 | 7/2003 | Pawlak |
| 2003/0142704 A1 | 7/2003 | Lawandy |
| 2003/0142713 A1 | 7/2003 | Lawandy |
| 2003/0153006 A1 | 8/2003 | Washizu |
| 2003/0162296 A1 | 8/2003 | Lawandy |
| 2003/0184730 A1 | 10/2003 | Price |
| 2003/0203390 A1 | 10/2003 | Kaye |
| 2003/0228610 A1 | 12/2003 | Seul |
| 2004/0002162 A1 * | 1/2004 | Leugers et al. ............ 436/171 |
| 2004/0027968 A1 | 2/2004 | Horimai |
| 2004/0032650 A1 * | 2/2004 | Lauer ............ 359/385 |
| 2004/0047030 A1 | 3/2004 | MacAulay |
| 2004/0062178 A1 | 4/2004 | Horimai |
| 2004/0075907 A1 * | 4/2004 | Moon et al. ............ 359/566 |
| 2004/0100636 A1 | 5/2004 | Somekh |
| 2004/0100892 A1 | 5/2004 | Horimai |
| 2004/0125370 A1 | 7/2004 | Montagu |
| 2004/0125424 A1 | 7/2004 | Moon |
| 2004/0126875 A1 * | 7/2004 | Putnam et al. ............ 435/287.2 |
| 2004/0130786 A1 * | 7/2004 | Putnam et al. ............ 359/566 |
| 2004/0132205 A1 * | 7/2004 | Moon et al. ............ 436/174 |
| 2004/0156471 A1 | 8/2004 | Sakata |
| 2004/0170356 A1 | 9/2004 | Iazikov |
| 2004/0175842 A1 | 9/2004 | Roitman |
| 2004/0175843 A1 * | 9/2004 | Roitman et al. ............ 436/531 |
| 2004/0179267 A1 | 9/2004 | Moon |
| 2004/0209376 A1 | 10/2004 | Natan |
| 2004/0233485 A1 | 11/2004 | Moon |
| 2004/0263923 A1 | 12/2004 | Moon |
| 2005/0042764 A1 | 2/2005 | Sailor |
| 2005/0054004 A1 | 3/2005 | Alivisatos |
| 2005/0056587 A1 | 3/2005 | Allen et al. |
| 2005/0220408 A1 | 10/2005 | Putnam |
| 2005/0227252 A1 | 10/2005 | Moon |
| 2005/0270603 A1 | 12/2005 | Putnam |
| 2006/0023310 A1 | 2/2006 | Putnam |
| 2006/0028727 A1 | 2/2006 | Moon |
| 2006/0050544 A1 | 3/2006 | Horimai |
| 2006/0057729 A1 | 3/2006 | Moon |
| 2006/0063271 A1 | 3/2006 | Putnam |
| 2006/0067179 A1 | 3/2006 | Matsumoto |
| 2006/0071075 A1 | 4/2006 | Moon |
| 2006/0072177 A1 | 4/2006 | Putnam |
| 2006/0118630 A1 | 6/2006 | Kersey |
| 2006/0119913 A1 | 6/2006 | Moon |
| 2006/0132877 A1 | 6/2006 | Kersey |
| 2006/0134324 A1 | 6/2006 | Putnam |
| 2006/0139635 A1 | 6/2006 | Kersey |
| 2006/0140074 A1 | 6/2006 | Horimai |
| 2006/0160208 A1 | 7/2006 | Putnam |
| 2007/0121181 A1 | 5/2007 | Moon |
| 2007/0146869 A1 * | 6/2007 | Lauer ............ 359/368 |
| 2007/0236789 A1 | 10/2007 | Moon |
| 2008/0085565 A1 | 4/2008 | Moon |
| 2008/0129990 A1 | 6/2008 | Moon |
| 2008/0165656 A1 | 7/2008 | Moon et al. |
| 2008/0170664 A1 | 7/2008 | Kalman |
| 2008/0192311 A1 | 8/2008 | Horimai |
| 2009/0034078 A1 | 2/2009 | Putnam et al. |
| 2009/0040885 A1 | 2/2009 | Horimai |
| 2009/0073520 A1 | 3/2009 | Kersey et al. |
| 2009/0194589 A1 | 8/2009 | Moon et al. |
| 2010/0025482 A1 | 2/2010 | Moon |
| 2010/0072278 A1 | 3/2010 | Putnam |
| 2010/0099574 A1 | 4/2010 | Moon |
| 2010/0246005 A1 | 9/2010 | Moon |
| 2010/0246007 A1 | 9/2010 | Moon |
| 2010/0255603 A9 | 10/2010 | Putnam |
| 2011/0003394 A1 | 1/2011 | Kersey |
| 2011/0033948 A9 | 2/2011 | Moon |

(56) References Cited

U.S. PATENT DOCUMENTS

| | | | |
|---|---|---|---|
| 2011/0058172 | A1 | 3/2011 | Moon |
| 2011/0114729 | A1 | 5/2011 | Moon |

FOREIGN PATENT DOCUMENTS

| | | | |
|---|---|---|---|
| EP | 0 395 300 | | 10/1990 |
| EP | 0 723 149 | | 7/1996 |
| EP | 0 798 573 | A1 | 10/1997 |
| EP | 0 911 667 | A1 | 4/1999 |
| EP | 916981 | | 5/1999 |
| EP | 0 972 817 | A1 | 1/2000 |
| EP | 1182054 | | 2/2002 |
| EP | 1219979 | | 7/2002 |
| GB | 2 118 189 | | 10/1983 |
| GB | 2129551 | | 5/1984 |
| GB | 2 138 821 | | 10/1984 |
| GB | 2289150 | A | 11/1995 |
| GB | 2 299 235 | | 9/1996 |
| GB | 2 306 484 | | 5/1997 |
| GB | 2 319 838 | | 6/1998 |
| GB | 2372100 | | 8/2002 |
| JE | 22182022 | A2 | 6/2002 |
| JP | 58143254 | | 8/1983 |
| JP | 08102544 | | 4/1986 |
| JP | 01047950 | | 2/1989 |
| JP | 05307119 | A2 | 11/1993 |
| JP | 06333102 | A2 | 2/1994 |
| JP | 08272923 | A2 | 10/1996 |
| JP | 10160705 | | 6/1998 |
| JP | 11119029 | | 4/1999 |
| JP | 20035521 | | 2/2000 |
| JP | 00249706 | | 9/2000 |
| JP | 2001091715 | A | 4/2001 |
| JP | 2002-513166 | | 5/2002 |
| JP | 2003004671 | | 8/2003 |
| WO | WO 91/06496 | | 5/1991 |
| WO | WO 93/09668 | | 5/1993 |
| WO | WO 94/28119 | | 12/1994 |
| WO | WO 96/24061 | | 8/1996 |
| WO | 9636436 | | 11/1996 |
| WO | WO 96/36436 | | 11/1996 |
| WO | WO 97/12680 | | 4/1997 |
| WO | WO 97/15390 | | 5/1997 |
| WO | WO 97/015690 | | 5/1997 |
| WO | WO 97/17258 | | 5/1997 |
| WO | WO 97/31282 | | 8/1997 |
| WO | WO 97/34171 | | 9/1997 |
| WO | WO 98/04740 | | 2/1998 |
| WO | WO 98/24549 | | 6/1998 |
| WO | WO 99/02266 | | 1/1999 |
| WO | WO 99/09042 | | 2/1999 |
| WO | WO 99/32654 | | 7/1999 |
| WO | WO 99/42209 | | 8/1999 |
| WO | WO 00/08443 | | 2/2000 |
| WO | 0016893 | | 3/2000 |
| WO | WO 00/19262 | | 6/2000 |
| WO | WO 00/37914 | | 6/2000 |
| WO | WO 00/37969 | | 6/2000 |
| WO | WO 00/39617 | | 7/2000 |
| WO | 0061198 | | 10/2000 |
| WO | WO 00/63419 | | 10/2000 |
| WO | 0158583 | | 8/2001 |
| WO | 0171322 | | 9/2001 |
| WO | 0178889 | | 10/2001 |
| WO | WO 01/78889 | | 10/2001 |
| WO | 02059306 | | 8/2002 |
| WO | WO 02/059603 | | 8/2002 |
| WO | WO 02/064829 | | 8/2002 |
| WO | 03061983 | | 7/2003 |
| WO | WO 2003/091731 | | 11/2003 |
| WO | WO 2004/011940 | | 2/2004 |
| WO | WO 2004/015418 | | 2/2004 |
| WO | 2004019276 | | 3/2004 |
| WO | 2004024328 | | 3/2004 |
| WO | 2004025562 | | 3/2004 |
| WO | WO 2004/019276 | | 3/2004 |
| WO | WO 2004/025561 | | 3/2004 |
| WO | WO 2004/025563 | | 3/2004 |
| WO | WO 2004/034012 | | 4/2004 |
| WO | WO 2004/046697 | | 6/2004 |
| WO | 2004066210 | | 8/2004 |
| WO | WO 2005/026729 | | 3/2005 |
| WO | WO 2005/027031 | | 3/2005 |
| WO | WO 2005/029047 | | 3/2005 |
| WO | WO 2005/033681 | | 4/2005 |
| WO | WO 2005/050207 | | 6/2005 |
| WO | WO 2005/079544 | | 9/2005 |
| WO | WO 2005/101487 | | 10/2005 |
| WO | WO 2006/020363 | | 2/2006 |
| WO | WO 2006/055735 | | 5/2006 |
| WO | WO 2006/055736 | | 5/2006 |
| WO | WO 2006/076053 | | 7/2006 |

OTHER PUBLICATIONS

"Electronically Scanned Confocal Imaging System"; IBM Technical Disclosure Bulletin; vol. 36; No. 06B; Jun. 1993; pp. 261-262.

"Ben Beune Patent Licensing Director of Philips IP&S"; Replication & Duplication—News Jan.-Feb. 2002; pp. 1-2.

Andrew Marshall; "DNA Chips: Array of Possibilities"; Nature Biotechnology vol. 16 Jan. 1998; pp. 27-31.

Burstein Technology, Inc.; "Angel Strategies Tombstone"; 1 pg.

de Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.

Fonjallaz et al., "Interferometric Side Diffraction Technique for the Characterisation of Fiber Gratings"; 1999 OSA Conference, Sep. 23-25; 3 pgs.

G. Kakarantzas et al.;"Transmission Filters Based on periodically Micro-tapered Fibre"; CLE0/2000/Friday Morning; 8:45 a.m.; pp. 574-575.

Hideki Kambara; Recent Progress in fluorescent DNA Analyzers and Methods; Current Topics in Analytical checmistry; vol. 1, (1998) pp. 21-36.

Ivan Oransky; "Sequencing on Compact Disc? Microgenomics of Breast Cancer; Better Binding Site Prediction"; vol. 17 / Issue 13 / 35 / Jun. 30, 2003; 13 pgs.

Kashyap R.; "Fiber Bragg Gratings"; Academic Press, Ch. 9; pp. 430-433; 1999.

Kogelnik H; "Coupled Wave Theory for Thick Hologram Gratings"; The Bell System Technical Journal, 48(9):2909-2947 (1969).

Krug P., "Measurement of Index Modulation Along an Optical Fiber Bragg Grating"; Optics Letters, 20(17):1767-1769.

Leith et al., "Holographic Data Storage in Three-Dimensional Media"; Applied Optics, vol. 5, No. 8, Aug. 1966; 21 pgs.

Mark O. Worthington; "Curriculum Vitae"; Jan. 5, 2004; 4 pgs.

Masato Mitsuhashi; "Gene Manipulation on Plastic Plates"; Nature, vol. 357, Jun. 11, 1992; pp. 519-520.

Michael C. Needels et al.; "Generation and Screening of an Oligonucleotide-Encoded Synthetic Peptide Library"; Proc Natl. Acad. Sci. USA, vol. 90;pp. 10700-10704, Nov. 1993.

Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.

Shelia R. Nicerwarner-Pena, "Submicrometer Metallic Barcodes"; Science, vol. 294; Oct. 5, 2001; 5 pgs.

Thomas Laurell; "Enhanced Enzyme Activity in Silicon Integrated Enzyme Reactors Utilizing Porous Silicon as the Coupling Matrix"; Sensor & Actuators B 31 (1996); pp. 161-166.

Vander Lugt; "Design Relationships for Holographic Memories"; Applied Optics, vol. 12, No. 7, Jul. 1973; pp. 1675-1685.

W.R. Rigby; "An Anodizing Process for the Production of Inorganic Microfiltration Membranes"; 2436Transactions of the Institute of Metal Finishing;68 Aug. 1990,Part 3 p. 95-98.

Yoshinobu Kohara; "DNA Probes on Beads Arrayed in a Capillary, 'Bead-Array',Exhibited High Hybridization Performance"; Nucleic Acids Research, 2002, vol. 30, No. 16 e87; 7 pgs.

(56) References Cited

OTHER PUBLICATIONS

Material Safety Data Sheet Aquaclean 900; Aquabond Technologies (ABT); 1 pg., revised May 2000.
U.S. Patent No. 6,780,301 to Natan et al., published Aug. 2004 (Patent was deleted after issuance so no longer part of PTO database).
Lawton et al. "Biomolecular Self-Assembly of Quantum-Dot Composites" Material Research Society Proceedings 330:283 (6 pages) (1994).
Jain KK, Nanodiagnostics: Application of Nanotechnology in Molecular Diagnostics, Expert Review of Molecular Diagnostics 3(2):153-161 (2003), XP008038849.
Lide (CRC Handbook of Chemistry and Physics, 71st ed.), 1991.
Othonos, X. Lee; Superimposed Multiple Bragg Gratings, Nov. 10, 1994, vol. 30, No. 23.
Patil et al. (AAPS PharmSciTech, Mar. 24, 2006, vol. 7, pp. E1-E7).
Po Ki Yuen, Microbarcode Sorting Device; Science & Technology, Corning Incorparated, Corning, New York 14831-0007, USA, 2003.
International Search Report and Written Opinion for International Application No. PCT/US2003/26315, 2004.
International Search Report and Written Opinion for International Application No. PCT/US2003/26316, 2004.
International Search Report for International Application No. PCT/US2003/28862, 2004.
International Search Report for International Application No. PCT/US2003/28874, 2004.
International Search Report for International Application No. PCT/US2003/28875, 2004.
International Search Report for International Application No. PCT/US2003/28887, 2004.
International Search Report for International Application No. PCT/US2003/28890, 2003.
International Search Report and Written Opinion for International Application No. PCT/US2003/29164, 2004.
International Search Report for International Application No. PCT/US2003/29244, 2004.
International Search Report and Written Opinion for International Application No. PCT/US2004/01685, 2004.
International Search Report and Written Opinion for International Application No. PCT/US2004/30037, 2005.
International Search Report and Written Opinion for International Application No. PCT/US2004/30038, 2005.
International Search Report and Written Opinion for International Application No. PCT/US2004/30300, 2005.
International Search Report and Written Opinion for International Application No. PCT/US2004/32084, 2005.
International Search Report and Written Opinion for International Application No. PCT/US2004/38416, 2005.
International Search Report and Written Opinion for International Application No. PCT/US2005/05743, 2006.
International Search Report and Written Opinion for International Application No. PCT/US2005/05745, 2006.
International Search Report and Written Opinion for International Application No. PCT/US2005/26289, 2006.
International Search Report and Written Opinion for International Application No. PCT/US2005/33694, 2006.
International Search Report and Written Opinion for International Application No. PCT/US2005/41730, 2006.
International Search Report and Written Opinion for International Application No. PCT/US2005/41731, 2006.
Introduction to Flow Cytometry: A Learning Guide. Manual Part No. 11-11032-01, Apr. 2000, 54 pgs.
Lawton et al. "Biomolecular Self-Assembly of Quantum-Dot Composites." Mat. Res. Soc. Symp. Proc. vol. 330, 1994, Materials Research Society.
US 6,780,301, 08/2004, Natan (withdrawn)

* cited by examiner

Range of angles for Bragg envelope measurement

96 Microtitre Plate (a)  
Top View of Well (b)  
Side View of Well Bottom (c)  
Top View of Well (d)

(A)

(B)

Gap - 0.2 mm

OPTICAL SYSTEM AND METHOD FOR READING ENCODED MICROBEADS

CROSS REFERENCES TO RELATED APPLICATIONS

The present application is a continuation of U.S. application Ser. No. 11/281,907 (the '907 Application) filed on Nov. 16, 2005, entitled "Fourier Scattering Methods for Encoding Microbeads and Methods and Apparatus for Reading the Same." The '907 application is a continuation-in-part of U.S. patent application Ser. No. 10/645,689, filed 20 Aug. 2003, entitled "Diffraction Grating-Based Optical Identification Element" and U.S. patent application Ser. No. 10/661,234 (U.S. Patent Appl. Publ. No. 2004/0233485), filed 12 Sep. 2003, similarly entitled "Diffraction Grating-Based Optical Identification Element." The '907 Application also claims benefit to U.S. provisional patent application No. 60/628,897, filed Nov. 16, 2004 Each of the above applications is hereby incorporated by reference in its entirety.

The following cases contain subject matter also related to that disclosed herein and are incorporated herein by reference in their entirety, as follows: U.S. patent application Ser. No. 10/645,686 (U.S. Patent Appl. Publ. No. 2004/0075907), filed Aug. 20, 2003, entitled "End Illuminated Bragg Grating based Optical Identification Element"; U.S. patent application Ser. No. 10/661,031 (U.S. Patent Appl. Publ. No. 2004/0125424), filed Sep. 12, 2003, entitled "DIFFRACTION GRATING-BASED ENCODED MICRO-PARTICLES FOR MULTIPLEXED EXPERIMENTS"; U.S. patent application Ser. No. 10/661,082 (U.S. Patent Appl. Publ. No. 2004/0179267), filed Sep. 12, 2003, entitled "Method and Apparatus for Labeling Using Diffraction Grating-based Encoded Optical Identification Elements"; U.S. patent application Ser. No. 10/661,115 (U.S. Patent Appl. Publ. No. 2004/0126875 ), filed Sep. 12, 2003, entitled "Assay Stick"; U.S. patent application Ser. No. 10/661,836 (U.S. Patent Appl. Publ. No. 2004/0132205 ), filed Sep. 12, 2003, entitled "Method and Apparatus for Aligning Microbeads in order to Interrogate the Same"; U.S. patent application Ser. No. 10/661,254 (U.S. Patent Appl. Publ. No. 2004/0130761 ), filed Sep. 12, 2003, entitled "Chemical Synthesis Using Diffraction Grating-based Encoded Optical Elements"; U.S. patent application Ser. No. 10/661,116 (U.S. Patent Appl. Publ. No. 2004/0130786 ), filed Sep. 12, 2003, entitled "Method of Manufacturing of a Diffraction grating-based identification Element"; and U.S. patent application Ser. No. 10/763,995 (U.S. Patent Appl. Publ. No. 2004/0263923 ), filed Jan. 22, 2004, entitled, "Hybrid Random bead/chip based microarray". Sections below reproduce subject matter from U.S. Provisional Application No. 60/441,678, filed Jan. 22, 2003, entitled "Hybrid Random Bead/Chip Microarray" and from U.S. Provisional Application No. 60/519,932, filed Nov. 14, 2003, entitled, "Diffraction Grating-Based Encoded Microparticles for Multiplexed Experiments".

BACKGROUND OF THE INVENTION

1. Field of Invention

The present invention relates to a method and apparatus for reading a code on an optical element; and more particularly, to a method and apparatus for reading a code on a microbead that is typically 1-1000 microns in size using a Fourier plane analysis technique.

2. Description of Related Art

Tiny microbeads that are individually identifiable have many applications in drug discovery, genomics, chemistry, and security. Microbeads are very small objects, typically 1-1000 microns (um) in feature size. They may be cylindrical, cubic, rectangular, or any other shape. Typically microbeads are composed of silica based glass. Coded microbeads are individually identifiable. There are many methods available to encode microbeads. Known methods for encoding microbeads include fluorescence intensity and/or color, chemical techniques, spatial marks on the particles and radio-frequency encoding. However, the known ways involve using expensive, high resolution, optical techniques for imaging and reading the code off the microbead.

For example, FIG. 1 shows such a spatial imaging technique generally indicated as 10' for reading encoded particles or microbeads that is known in the art, and includes an input light source 12' for passing input light through a microbead 14 and imaging optics, including an imaging lens 16, to project an image of the microbead 14 on an imaging plane 18 for reading the image using expensive, high resolution, imaging equipment 20. The imaging lens 16 is arranged between the microbead 14 and the image plane 18 at a distance of two focal lengths from each. The imaging optics are also expensive to provide the high resolution image needed to read or interpret the code on the microbead.

In view of this, there is a need in the industry for a less expensive way to encode and decode microbeads.

SUMMARY OF INVENTION

In its broadest sense, the present invention provides a new and unique method and apparatus for reading a microbead having a code thereon, wherein the code is projected on and read from a Fourier plane.

In operation, the code is projected on the Fourier plane by first scattering input light off (reflected or transmitted) the microbead. The light scattered from the microbead is directed through an optical arrangement having a transform lens for projecting the code on the Fourier plane, and read on the Fourier plane with a Fourier plane reading device, including a charge coupled device (CCD) or other suitable Fourier plane reading device and a processor for performing Fourier plane analysis. The transform lens is arranged between the microbead and the Fourier plane at a distance of one focal length from each, while the charge coupled device (CCD) or other suitable Fourier plane reading device is arranged on the Fourier plane. The whole thrust of the present invention is to analyze the spatial frequency of the light that is projected on the Fourier plane, after scattering from through the microbead and optical arrangement.

The microbead may be 1-1000 microns (um) or smaller in feature size.

The code may include periodic layers of material having different absorption, refractivities, or phase, including index of refraction differences; periodic spatial modulations having a different phase or amplitude; a periodic binary phase change used to code information in the Fourier plane; a photonic crystal used to encode the information on the microbead, wherein a pattern of holes causes interference between incident and scattered light to form spatial and spectral patterns in the far field that are unique to the pattern of holes; or may be formed in the microbead using a single photoactive inner region, a series of longitudinal holes, different fluorescence regions, or concentric rings of material in a preform. In effect, the present invention has applications in reading any unique and repeatable code formed in a microbead that can be projected on and read from a Fourier plane, including codes that are presently otherwise imaged on an image plane in the prior art in order to be read.

The present invention also provides new and unique Fourier scattering techniques for encoding microbeads, as well as providing one or more new and unique microbeads having a code thereon that may be projected on and read from a Fourier plane according to the method disclosed herein.

One important advantage of the present invention is that the Fourier plane analysis enables the use of a substantially less expensive code reader and code reading optics, such as a CCD array, since the code on the microbead does not have to be imaged in high order resolution in order to be interpreted.

Another advantage is that translationally invariant codes may be written over a large area when an optical filament is drawn from a preform and then cut into smaller sections in order to make the microbeads.

Still another advantage is that, because the code is projected and read in the Fourier plane or "far field", the reader does not require expensive or powerful imaging and magnifying optics to create a high resolution magnified image of the bead/particle to read the code. This is different from the prior art which actually image the bead itself to determine the code, e.g., for small particles that have bar codes printed on them.

BRIEF DESCRIPTION OF THE DRAWING

The drawing, not drawn to scale, includes the following Figures.

DETAILED DESCRIPTION OF INVENTION

Figure 2:
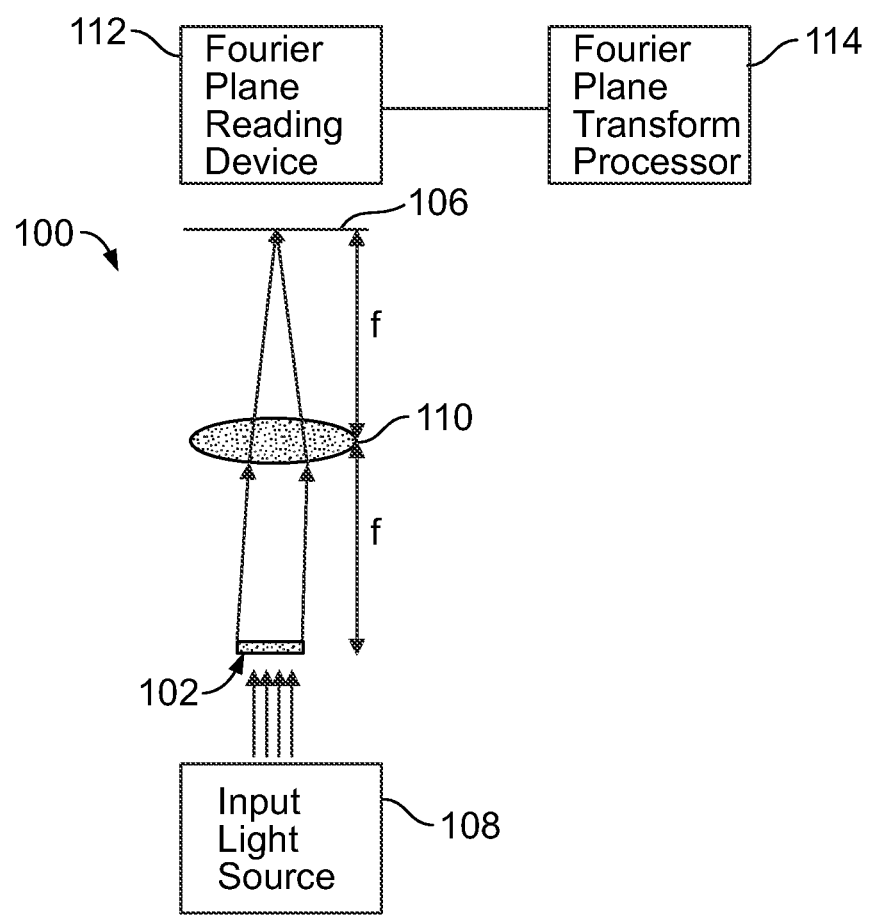
FIG. 2 shows a diagram of a new technique for reading encoded particles or microbeads according to the present invention.

FIG. 2 shows an optical arrangement using a Fourier transform technique generally indicated as 100 for reading a microbead or other suitable optical element generally indicated 102 having a code 104 (See, for example, FIG. 3) written thereon, wherein the code 104 is projected on and read from a Fourier plane 106.

In operation, the code 104 is projected on the Fourier plane 106 by passing input light from an input light source 108 through the microbead 102 and an optical arrangement having a transform lens 110 for focusing the code 104 on the Fourier plane 106, and read on the Fourier plane 106 with a Fourier plane reading device 112, including a charge coupled device (CCD) or other suitable Fourier plane reading device and a processor for performing Fourier plane analysis. The transform lens 110 is arranged between the microbead 102 and the Fourier plane 106 at a distance of about one focal length f from each, while the charge coupled device (CCD) or other suitable Fourier plane reading device is arranged on the Fourier plane. The light at the CCD device 112 is placed at the Fourier plane, and represents the Fourier transform of the resultant refractive index variation in the microbead 102. The whole thrust of the present invention is to analyze the spatial frequency of the light that is projected on the Fourier plane 106, after passing through or scattering off the microbead and optical arrangement.

The Fourier transform optics, including the transform lens 110, for focusing the code 104 (FIG. 3) on the Fourier plane 106 is known in the art, and the scope of the invention is not intended to be limited to any particular type or kind thereof. Moreover, the scope of the invention is intended to include using other optical arrangement, with or without such transform lens, now known or later developed in the future.

The charge coupled device (CCD) or other suitable Fourier plane reading device is an inexpensive optical device that are known in the art, and the scope of the invention is not intended to be limited to any particular type or kind thereof.

The optical arrangement 100 also includes a Fourier plane transform processor 114 for performing Fourier plane analysis to determine the code from the resultant refractive index variation. The Fourier plane transform processor 114 may be implemented using hardware, software, firmware, or some combination thereof. In a typical software implementation, the Fourier plane transform processor 114 may be one or more microprocessor-based architectures having a microprocessor, a random access memory (RAM), a read only memory (ROM), input/output devices and control, data and address buses connecting the same. A person skilled in the art of programming would be able to program such a microprocessor-based implementation to perform the functionality described herein without undue experimentation. The scope of the invention is not intended to be limited to any particular implementation using technology known or later developed in the future. Moreover, the processor 114 may form part of the Fourier plane reading device 112, or may be implemented as a separate module or processing unit. Finally, the scope of the present invention is also intended to include implementing one or more steps to carry out the invention via a computer program running in a Fourier plane transform processor, controller or other suitable module in an optical system, including but not limited to performing the Fourier plane analysis to determine the code from the resultant refractive index variation.

FIG. 2a

Figure 2A:
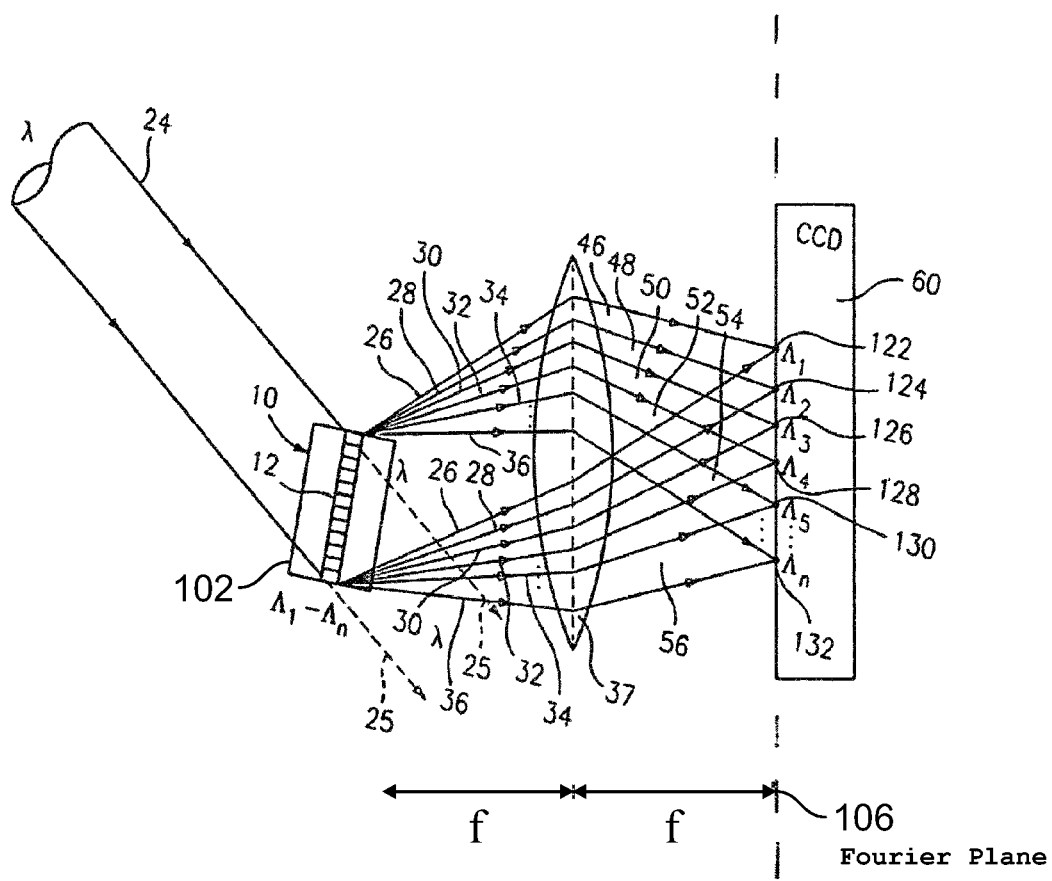
FIG. 2a shows another diagram of the new technique for reading encoded particles or microbeads according to the present invention.

FIG. 2a shows another example of the Fourier transform technique similar to the optical arrangement in FIG. 2, wherein an incident light 24 of a wavelength $\lambda$, e.g., 532 nm from a known frequency doubled Nd:YAG laser or 632 nm from a known Helium-Neon laser, is incident on a grating 12 in a substrate 10 of a microbead such as 102 in FIG. 2. Any other input wavelength $\lambda$ can be used if desired provided $\lambda$ is within the optical transmission range of the substrate (discussed more hereinafter). A portion of the input light 24 passes straight through the grating 12 as indicated by dashed lines 25. The remainder of the light 24 is reflected by the grating 12 and forms a plurality of beams 26-36, each having the same wavelength $\lambda$ as the input wavelength $\lambda$ and each having a different angle indicative of the pitches ($\Lambda_1$-$\Lambda_n$) existing in the grating 12. The reflected light 26-36 passes through a transform lens 37, which is arranged between the microbead 102 and the Fourier plane 106 at a distance of about one focal length f from each. The transform lens 37 provides focused light beams 46-56 which are imaged on the Fourier plane 106 at locations 122, 124, 126, 128, 130, 132 onto a CCD camera 60. Consistent with that discussed above, instead of or in addition to the lens 37, other imaging optics may be used to provide the desired characteristics of the optical image/signal onto the camera 60 (e.g., spots, lines, circles, ovals, etc.), depending on the shape of the substrate and input optical signals. Also, instead of a CCD camera other devices may be used to read/capture the output light.

Figure 3:
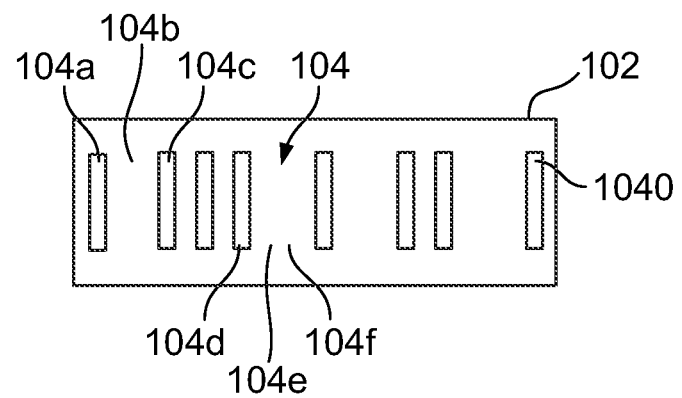
FIG. 3 shows a diagram of a microbead or optical element 102 as shown in FIG. 2.

FIG. 3: The Microbead or Optical Element 102

FIG. 3 shows, by way of example, the microbead 102 including the code 104 in the form of periodic layers of material with different reflectivity, which is known in the art. The material having different reflective spaces 104a, 104b, 104c, ..., 104o may include one reflectivity that may represent a logical "0" (indicated by blank spaces generally indicated by lead lines 104b, 104e, 104f, etc.), while the material having the other reflectivity may represent a logical "1" (indicated by elements 104a, 104c, 104d, etc.), or vice versa. As shown, the code 104 represents the binomial number "101 110 010 011 001", or "010 001 101 100 110" if the logical representation of the reflectivity is reversed. Consistent with that discussed above, the scope of the invention is not intended to be limited to any particular code or coding method or technique. Moreover, the scope of the invention is intended to be used in conjunction with known coding techniques, coding techniques that form part of the invention as described herein, as well as coding techniques later developed in the future.

Alternatively, the code 104 may include periodic layers of material having a different phase, including index of refraction differences; periodic spatial modulations having a different phase or amplitude; a periodic binary phase change used to code information in the Fourier plane; a photonic crystal used to encode the information on the microbead, wherein a pattern of holes causes interference between incident and scattered light to form spatial and spectral patterns in the far field that are unique to the pattern of holes; or may be formed in the microbead using a single photoactive inner region, a series of longitudinal holes, different fluorescence regions, or concentric rings of material in a preform. In effect, the present invention has applications in reading any code that is unique and repeatable, including codes that are otherwise imaged on an image plane in the prior art in order to be read.

The microbead or optical element 102 may be microscopic in size having a length in a range of 1-1,000 microns or smaller; or for larger applications may have a length of 1.0-1,000 millimeters or more. The outer diameter may be as small as less than 1,000 microns, as well as in a range of 1.0 to 1,000 millimeters for larger applications. Using manufacturing techniques developed in conjunction with the development of the present invention, one optical fiber or substrate can be drawn and processed to produce hundreds of thousands, as well as even a million or more of such unique microbeads. The microbead or optical element 102 may be used in which a substrate is used such as an optical substrate having the refractive index of the inner region is less than or equal to the outer region. By way of example, the reader is referred to the optical elements disclosed in provisional patent application Ser. Nos. 60/546,445 (CV-35), 60/546,435 (CV-53), 60/547,013 (CV-65), all filed on Feb. 19, 2004, U.S. patent application Ser. No. 10/661,836 (U.S. Patent Appl. Publ. No. 2004/0132205), filed Sep. 12, 2003, entitled "Method and Apparatus for Aligning Microbeads in order to Interrogate the Same". U.S. Patent Appl. Publ. No. 2004/0132205 is hereby incorporated by reference. Sections below reproduce subject matter from the 60/546,445; 60/546,435; and 60/547,013 applications. The scope of the invention is not intended to be limited to the type, kind, shape or size of the microbead or optical element 102. The scope of the invention is intended to include optical substrates both now known and later developed in the future.

Figure 4:
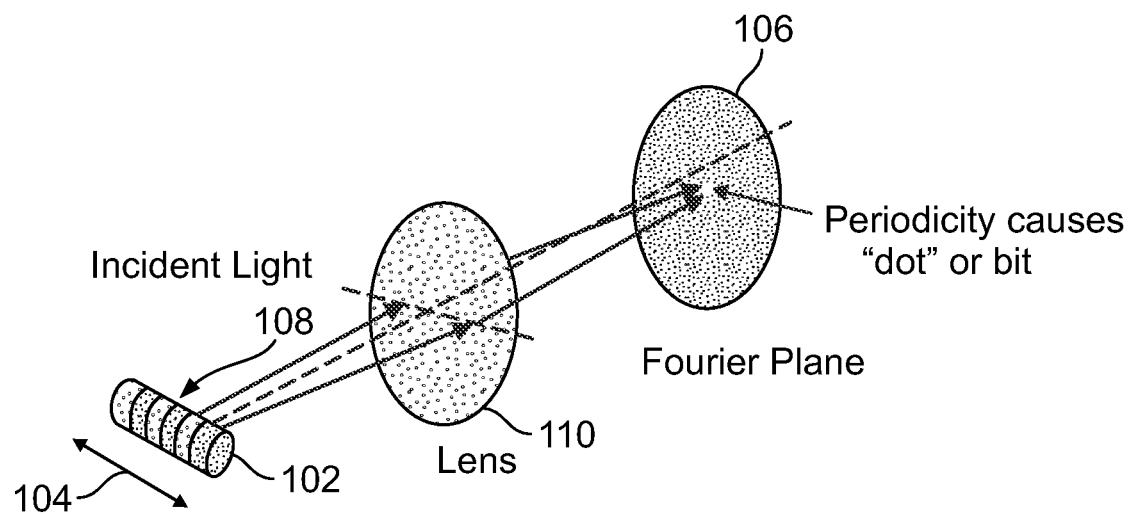
FIG. 4 shows an example of a Fourier plane readout of a multilayer metallic particle, which obviates the need for a high resolution imaging system.

FIG. 4:

FIG. 4 shows an example of a Fourier plane readout of a multilayer metallic particle, which obviates the need for a high resolution imaging system. Similar elements in FIGS. 2 and 4 are labelled with similar reference numeral. In this example, the microbead 102 has the code 104 in the form of a periodic spatial modulation (amplitude or phase) that reflects an incident light 108 through a transform lens 110 onto the Fourier plane, where the periodicity causes a "dot" or bit which may be read and interpreted accordingly.

It is important to note that, although in principle analog patterns can be used to encode in the Fourier plane, it is often advantageous to use only two "levels", where the levels can be either the phase (index) change and/or absorption change. For instance, the metallic layered particles of one known coding technique could be read out in a Fourier plane, thus obviating the necessity of a high resolution microscope. Periodic modulations of phase or amplitude can be "written" into an optical filament after it is drawn from a preform, allowing flexibility in the amount of particles that are encoded in a single batch.

Figure 5:
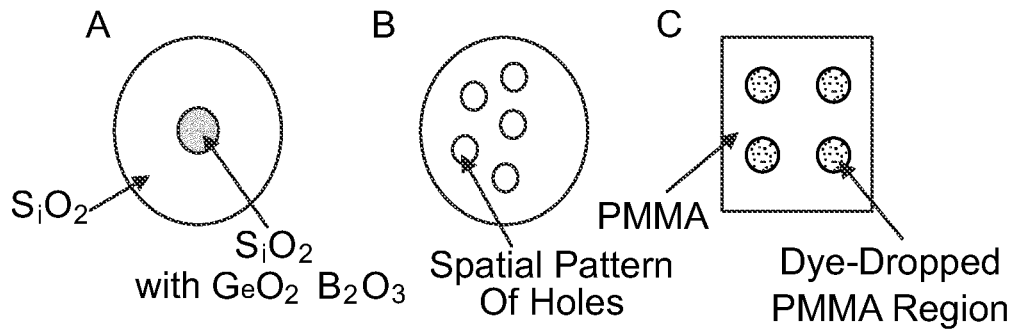
FIG. 5 shows examples of Fourier scattering techniques based on different inner region geometries in a filament drawn and cut from a preform to form microbeads according to the present invention.
Figure 5:
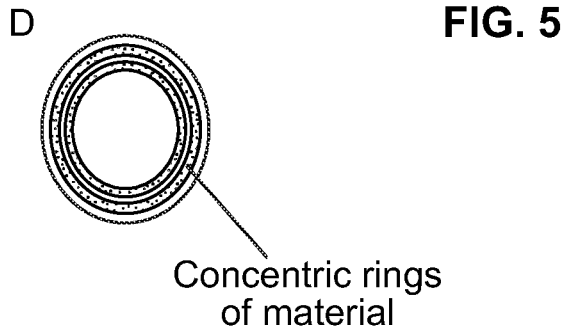
Figure 6:
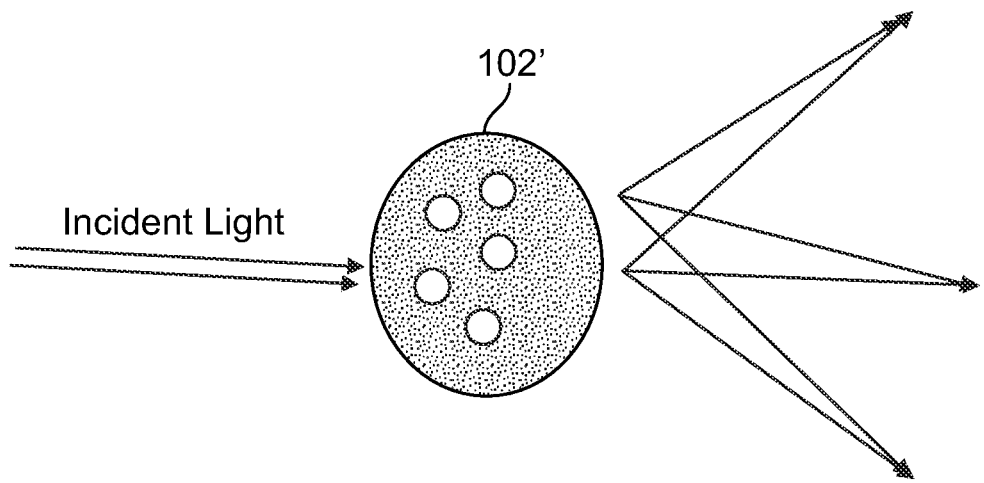
FIG. 6 shows another example of Fourier scattering techniques using photonic crystal microparticles which encode information according to the present invention.

FIGS. 5 and 6: Other Fourier Scattering Techniques for Encoding Microbeads

The present invention also provides many different types of Fourier scattering techniques for encoding microbeads that can be read using the Fourier plane analysis technique described herein. For example, many different geometries of the inner region and/or can be envisioned that can lead to a uniquely identifiable marking of the diced microbeads, including: a single photoactive inner region (FIG. 5A), a series of longitudinal holes (FIG. 5B), different fluorescence regions (FIG. 5C), or concentric rings (FIG. 5D) of material in the preform to name a few examples. These markings or patterns may be formed in the inner region and/or outer region of an optical filament drawn from a preform and cut to form the microbeads. These patterns on the microbeads are unique and repeatable and may be read using the Fourier plane analysis technique shown and described herein.

FIG. 6 shows still another examples of Fourier scattering techniques using photonic crystal microparticles which encode information according to the present invention. The pattern of the holes causes interferences between the incident and scattered light to form spatial and spectral patterns in the far field that are unique to the pattern of holes. In operation, incident light is provided to a microbead 102' having a photonic crystal therein causing a radiation pattern and spectrum that uniquely encodes information that can be read using the Fourier plane analysis technique described herein.

The scope of the invention is not intended to be limited to any particular pattern formed in the inner region and/or outer region of the filament being drawn from a preform using techniques now known or later developed in the future.

Figure 7:
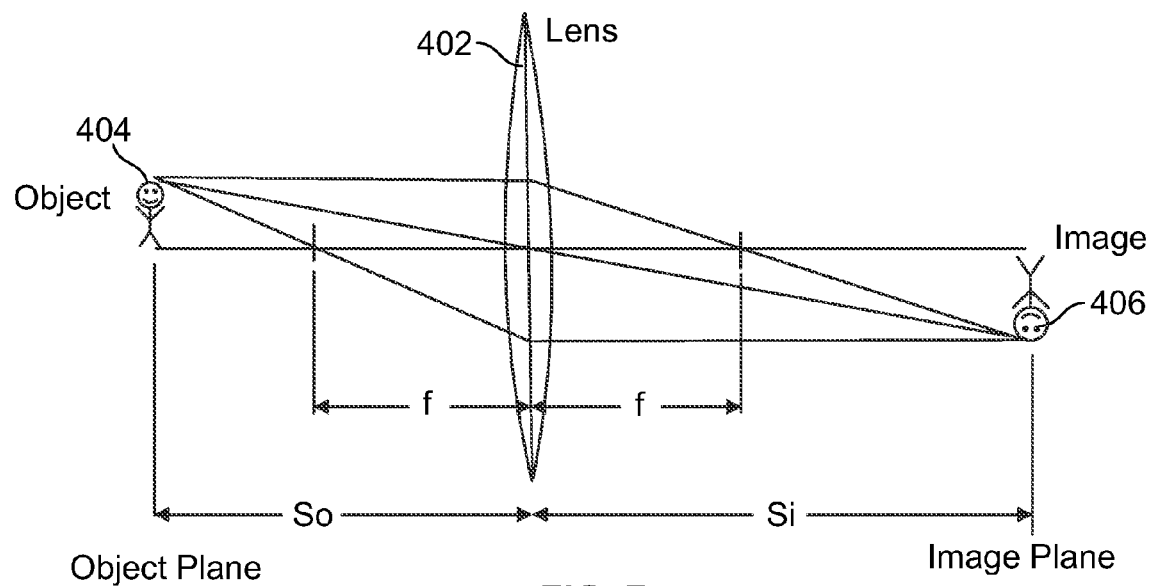
FIG. 7 illustrates the imaging properties of a known positive lens.

FIG. 7: the Imaging Properties

Referring to FIG. 7, the imaging properties of a known positive lens 402 may be described according to the following known principles. If an object 404 is located a distance $s_o$ away from the lens 402, i.e., in an "object plane", the lens 402 will form an image 406 in an "image plane" of the object 404 a distance $s_i$ away from the lens 402. The known relationship between $s_o$ and $s_i$ can be written as follows:

$$1/s_o + 1/s_i = 1/f$$

where f is the focal length of the lens 402 and $s_o$ is greater than the focal length of the lens 402. The size of the image relative to the object (or magnification M) has the known relationship:

$$M = s_i/s_o$$

where M is the size of the image 406 divided by the size of the object 404. Accordingly, if the lens 402 is placed a distance f away from the object 404, the image 405 is infinitely large at a distance of infinity away from the lens 402, as is known. For the purposes of this discussion, the lens 402 is presumed to be infinitely large, infinitely thin (i.e., a line) as located on a plane parallel to the plane of the lens, and with no aberrations.

Figure 8:
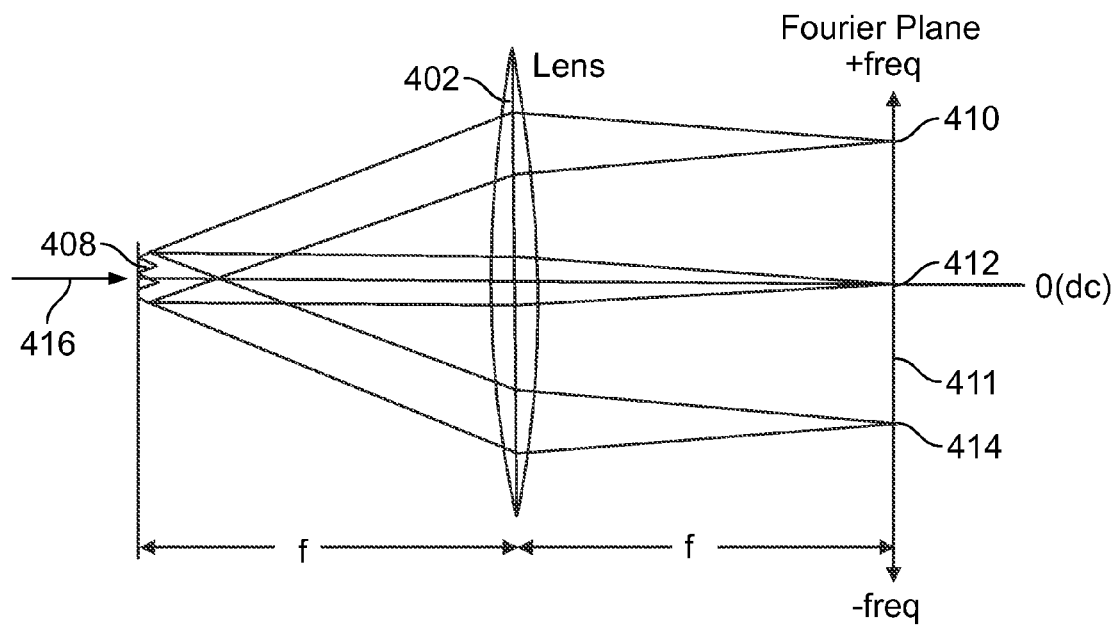
FIG. 8 illustrates the Fourier properties of a lens.

FIG. 8: the Fourier Properties

Referring to FIG. 8, the Fourier properties of a lens 402 may be described based on the following known principles. If the lens 402 is placed a distance f in front of an electric field distribution 408, the lens 402 will form an electric field distribution 410 that corresponds to the Fourier transform of the original electric field profile 408 at a distance f away from the lens 402 (i.e., at the "Fourier Plane" 411). The Fourier Plane image is also known as the "far field" image with a different scale, e.g., greater than about 20 Rayleigh ranges away. In particular, for the electric field sine wave 408 having a predetermined intensity or peak value and a DC offset, resulting Fourier transform intensity pattern in the Fourier Plane 411 provided by the lens 402 would be three delta functions (or points of light) 410, 412, 414, corresponding to the DC value at the point 412, the positive frequency value of the sign wave 408 at the point 410 and the negative value of the frequency of the sign wave 408 at the point 414. The intensity of the light at the point 412 corresponds to the DC value of the sine wave 408, and the intensity of the light at the points 410, 414 corresponds to the peak value of the sine wave 408.

Relating the Fourier Plane discussion above to a bar code printed on a bead or particle such as element 102 (FIG. 2) that is read by an optical reader such as element 112 (FIG. 2), the sine wave 408 could correspond to the bar code on the bead 102 having a single spatial period, an efficiency <100%, and where a light beam 412 is incident on the bead at an angle of 0 degrees to the normal of the grating vector (the longitudinal axis of the bead 8).

It should be further understood from FIGS. 7 and 8 that if the lens 402 is placed a distance $s_o$ away from the incident electric field 408, the lens would provide an image of the electric field 408 at a distance $s_i$ away with a magnification $s_o/s_i$ (not shown).

Accordingly, the present invention detects an image of the Fourier transform of the bar code on the bead 102 at the Fourier plane, which appears as lines on a CCD camera (or code camera) in the Fourier plane. As a result, the reader 112 does not require expensive imaging optics to obtain an image of the bead 102.

Figure 1:
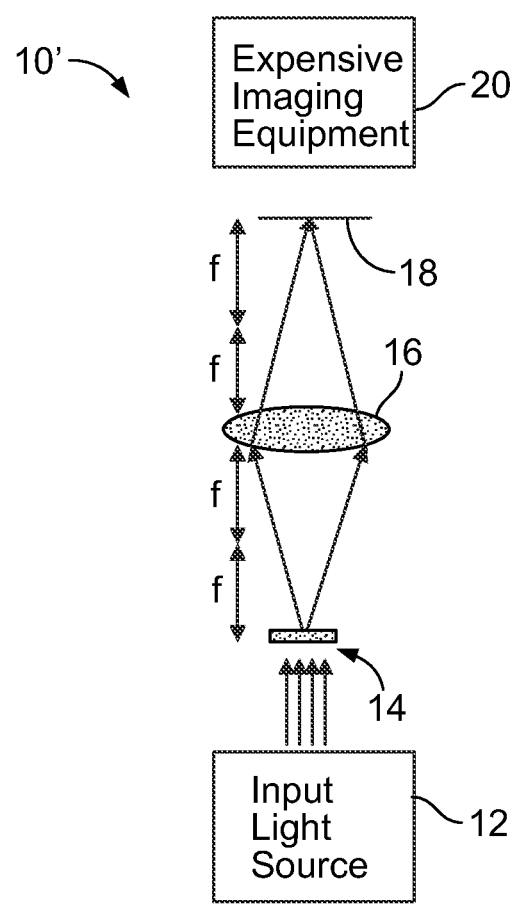
FIG. 1 shows a diagram of a spatial imaging technique for reading encoded particles or microbeads that is known in the art.

In contrast, as shown in FIG. 1, if the code on the bead 14 was detected by obtaining an image of the bead 14, e.g., if the code was simply as series of stripes printed on the bead 14, the reader/detector 20 would need to obtain a magnified image of the bead 14 with sufficient magnification to allow a code camera to read the stripes and thus obtain the code on the bead 14.

In this regard, if the appearance of the code on the bead looks like a bar code or digital code, the image in the Fourier plane will not look like the bar code or digital code, it will look like the Fourier transform of a bar code or digital code seen on the bead. Similarly, if the image of the code in the Fourier plane looks like a bar code or digital code, the appearance of the code on the bead will not likely look like a bar code or digital code because it will be the inverse Fourier transform of the bar code or digital code seen in the Fourier plane. Accordingly, it may be desirable to have the Fourier plane have a simple digital image that is easy to identify to keep the detector simple. In that case, the actual code on the bead itself will likely be unintelligible as a bar code or digital code.

Figure 9:
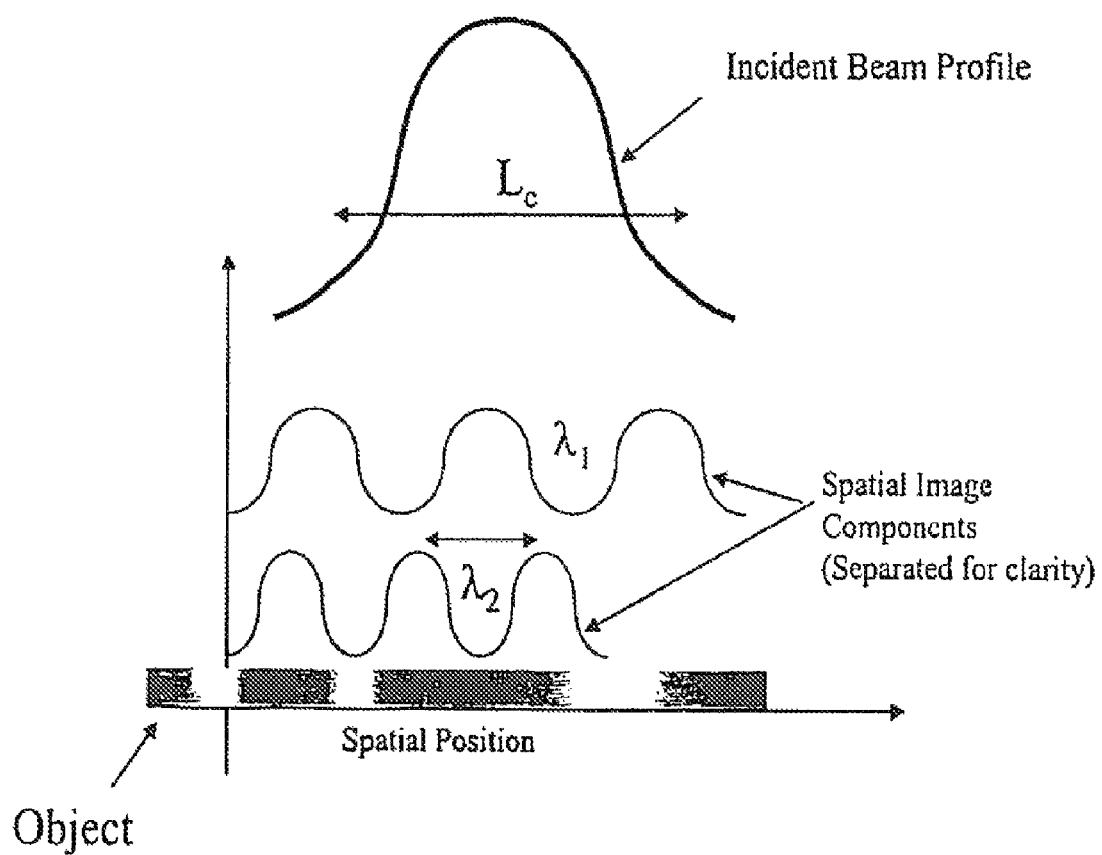
FIG. 9 shows a relationship between the spatial coherence length and two adjacent spatial frequencies.
Figure 10:
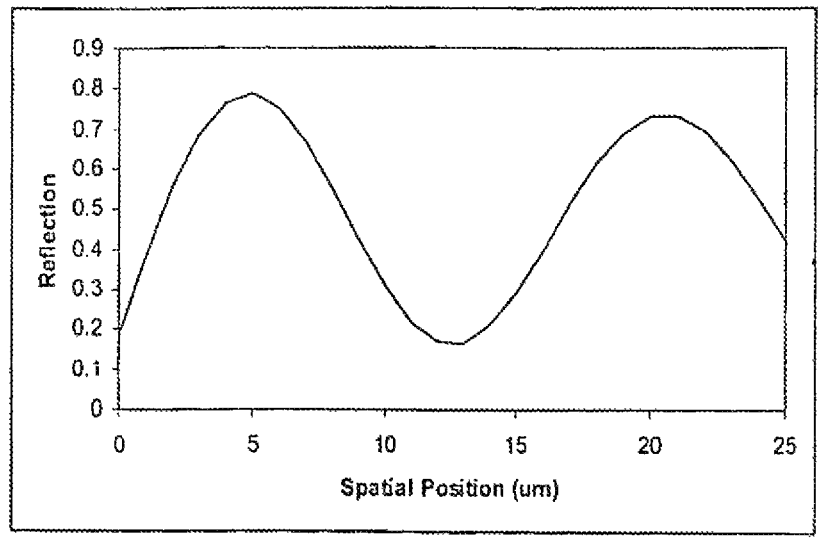
FIG. 10 shows an example of the reflectivity of an object composed of the spatial frequency components shown in FIG. 11.
Figure 11:
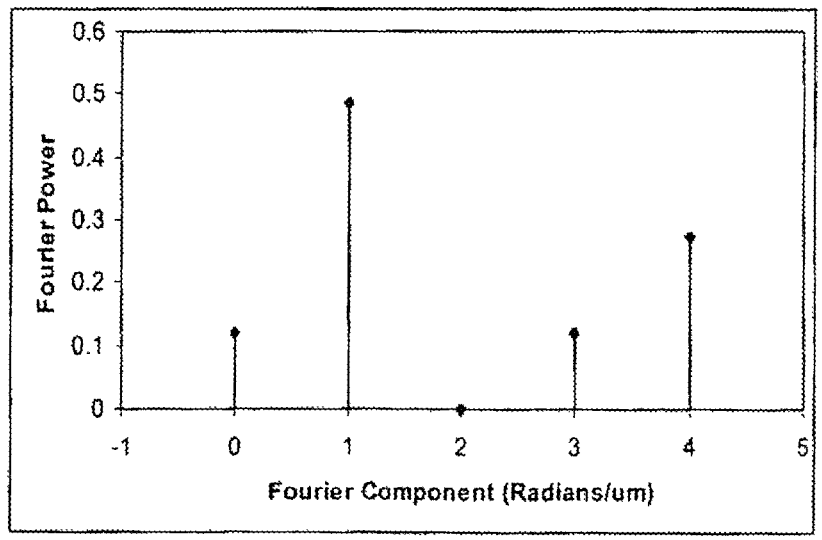
FIG. 11 is a graph showing Fourier components in relation to Fourier Power.

FIGS. 9-11: the Readout Beam

A technical requirement of the readout beam projected on the Fourier plane is that it must have a spatial coherence Lc large enough to resolve adjacent frequency components used to identify the object such as the microbead. FIG. 9 shows the relationship between the spatial coherence length and two adjacent spatial frequencies (shown schematically on FIG. 9.) The general requirement for the spatial coherence length is $1/L_c < 1/\lambda_1 - 1/\lambda_2$.

FIG. 10 shows an example of the reflectivity of an object composed of the spatial frequency components shown in FIG. 11. Information is contained in both the power amplitude and the spatial frequency of the Fourier components. A particularly robust method of identifying an object would be to look at the presence or absence of particular Fourier spatial frequencies, and choose a threshold to determine if a particular frequency corresponds to a logical "1" or a logical "0" (i.e. digital encoding.) If a threshold of 0.1 is chosen in the example of FIG. 11, then the corresponding digital code would be 11011 for the five spatial frequencies analyzed.

Figure 12:
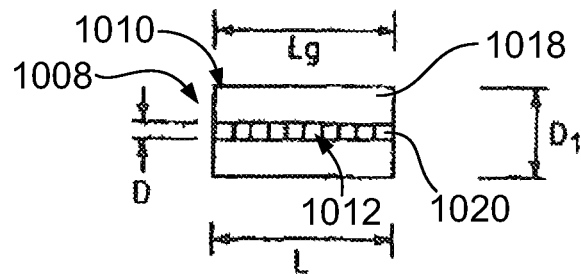
FIG. 12 is a side view of an optical identification element, in accordance with the present invention.

Referring to FIG. 12, a hybrid random bead/chip based microarray includes a diffraction grating-based optical identification element 1008 (or encoded element or coded element) which comprises a known optical substrate 1010, having an optical diffraction grating 1012 disposed (or written, impressed, embedded, imprinted, etched, grown, deposited or otherwise formed) in the volume of or on a surface of a substrate 1010. The grating 1012 is a periodic or a periodic variation in the effective refractive index and/or effective optical absorption of at least a portion of the substrate 1010.

The optical identification element 1008 described herein is similar to that described in Copending U.S. patent application Ser. No. 10/661,234 (U.S. Patent Appl. Publ. No. 2004/0233485), filed Sep. 12, 2003, entitled "Diffraction Grating-Based Optical Identification Element", which is incorporated herein by reference in its entirety.

In particular, the substrate 1010 has an inner region 1020 where the grating 1012 is located. The inner region 1020 may be photosensitive to allow the writing or impressing of the grating 1012. The substrate 1010 has an outer region 1018, which does not have the grating 1012 therein.

The grating 1012 is a combination of one or more individual spatial periodic sinusoidal variations (or components) in the refractive index that are collocated at substantially the same location on the substrate 1010 along the length of the grating region 1020, each having a spatial period (or pitch) Λ. The resultant combination of these individual pitches is the grating 1012, comprising spatial periods (Λ1-Λn) each representing a bit in the code. Thus, the grating 1012 represents a unique optically readable code, made up of bits, where a bit corresponds to a unique pitch Λ within the grating 1012. Accordingly, for a digital binary (0-1) code, the code is determined by which spatial periods (Λ1-Λn) exist (or do not exist) in a given composite grating 1012. The code or bits may also be determined by additional parameters (or additional degrees of multiplexing), and other numerical bases for the code may be used, as discussed herein and/or in the aforementioned patent application.

The grating 1012 may also be referred to herein as a composite or collocated grating. Also, the grating 1012 may be referred to as a "hologram", as the grating 1012 transforms, translates, or filters an input optical signal to a predetermined desired optical output pattern or signal.

The substrate 1010 has an outer diameter D1 and comprises silica glass (SiO2) having the appropriate chemical composition to allow the grating 1012 to be disposed therein or thereon. Other materials for the optical substrate 1010 may be used if desired. For example, the substrate 1010 may be made of any glass, e.g., silica, phosphate glass, borosilicate glass, or other glasses, or made of glass and plastic, or solely plastic. For high temperature or harsh chemical applications, the optical substrate 1010 made of a glass material is desirable. If a flexible substrate is needed, plastic, rubber or polymer-based substrate may be used. The optical substrate 1010 may be any material capable of having the grating 1012 disposed in the grating region 1020 and that allows light to pass through it to allow the code to be optically read.

The optical substrate 1010 with the grating 1012 has a length L and an outer diameter D1, and the inner region 1020 diameter D. The length L can range from very small "microbeads" (or microelements, micro-particles, or encoded particles), about 1-1000 microns or smaller, to larger "macroelements" for larger applications (about 1.0-1000 mm or greater). In addition, the outer dimension D1 can range from small (less than 1000 microns) to large (1.0-1000 mm and greater). Other dimensions and lengths for the substrate 1010 and the grating 1012 may be used.

The grating 1012 may have a length Lg of about the length L of the substrate 1010. Alternatively, the length Lg of the grating 1012 may be shorter than the total length L of the substrate 1010.

The outer region 1018 is made of pure silica (SiO2) and has a refractive index n2 of about 1.458 (at a wavelength of about 1553 nm), and the inner grating region 1020 of the substrate 1010 has dopants, such as germanium and/or boron, to provide a refractive index n1 of about 1.453, which is less than that of outer region 1018 by about 0.005. Other indices of refraction n1, n2 for the grating region 1020 and the outer region 1018, respectively, may be used, if desired, provided the grating 1012 can be impressed in the desired grating region 1020. For example, the grating region 1020 may have an index of refraction that is larger than that of the outer region 1018 or grating region 1020 may have the same index of refraction as the outer region 1018 if desired.

Figure 13:
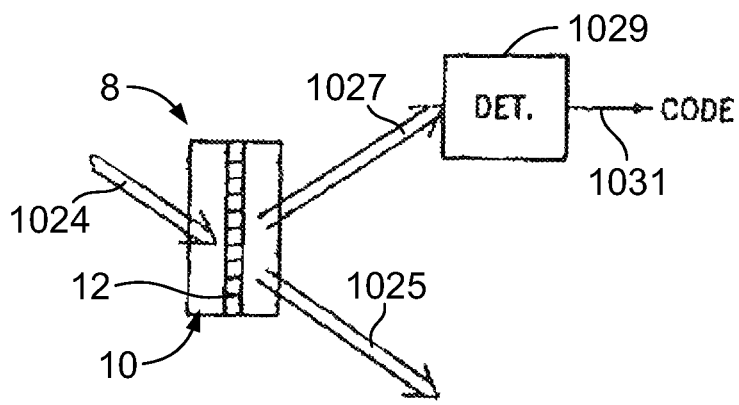
FIG. 13 is a top level optical schematic for reading a code in an optical identification element, in accordance with the present invention.

Referring to FIG. 13, an incident light 1024 of a wavelength λ, e.g., 532 nm from a known frequency doubled Nd:YAG laser or 632 nm from a known Helium-Neon laser, is incident on the grating 1012 in the substrate 1010. Any other input wavelength λ can be used if desired provided λ is within the optical transmission range of the substrate (discussed more herein and/or in the aforementioned patent application). A portion of the input light 1024 passes straight through the grating 1012, as indicated by a line 1025. The remainder of the input light 1024 is reflected by the grating 1012, as indicated by a line 1027 and provided to a detector 1029. The output light 1027 may be a plurality of beams, each having the same wavelength λ as the input wavelength λ and each having a different output angle indicative of the pitches (Λ1-Λn) existing in the grating 12. Alternatively, the input light 1024 may be a plurality of wavelengths and the output light 1027 may have a plurality of wavelengths indicative of the pitches (Λ1-Λn) existing in the grating 1012. Alternatively, the output light may be a combination of wavelengths and output angles. The above techniques are discussed in more detail herein and/or in the aforementioned patent application.

The detector 1029 has the necessary optics, electronics, software and/or firmware to perform the functions described herein. In particular, the detector reads the optical signal 1027 diffracted or reflected from the grating 1012 and determines the code based on the pitches present or the optical pattern, as discussed more herein or in the aforementioned patent application. An output signal indicative of the code is provided on a line 1031.

Figure 17:
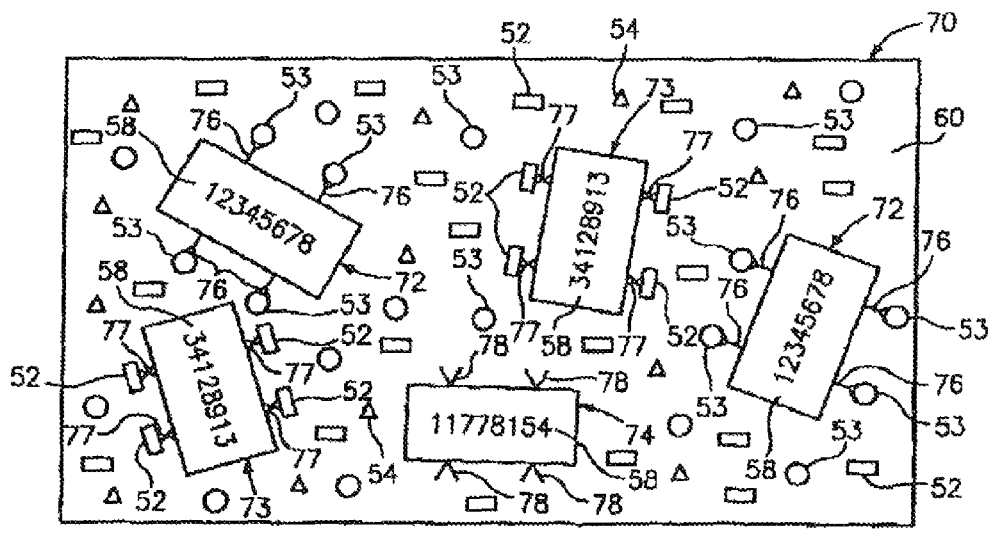
FIG. 17 is a schematic view of a plurality of optical identification elements having different identification or codes and coated with different probe substances disposed in a cell with a plurality of test substances, in accordance with the present invention.

Referring to FIGS. 14-19, and FIG. 14(*a*), the substrate 1010 of the optical identification element (or microbead) 1008 may be functionalized by coating or attaching a desired probe 1076, such as a compound, chemical or molecule, which is then used in an assay as an attractant for certain complimentary compounds, chemicals or molecules, otherwise known as a "target" analyte 1052-1054 (see FIG. 17). This capability to uniquely encode a large number of microbeads 1008 with a corresponding unique probe 1076 attached thereto enables these functionalized microbeads 1072 to be mixed with unknown "target" analytes 1052-1054 to perform a multiplexed experiment.

Figure 14:
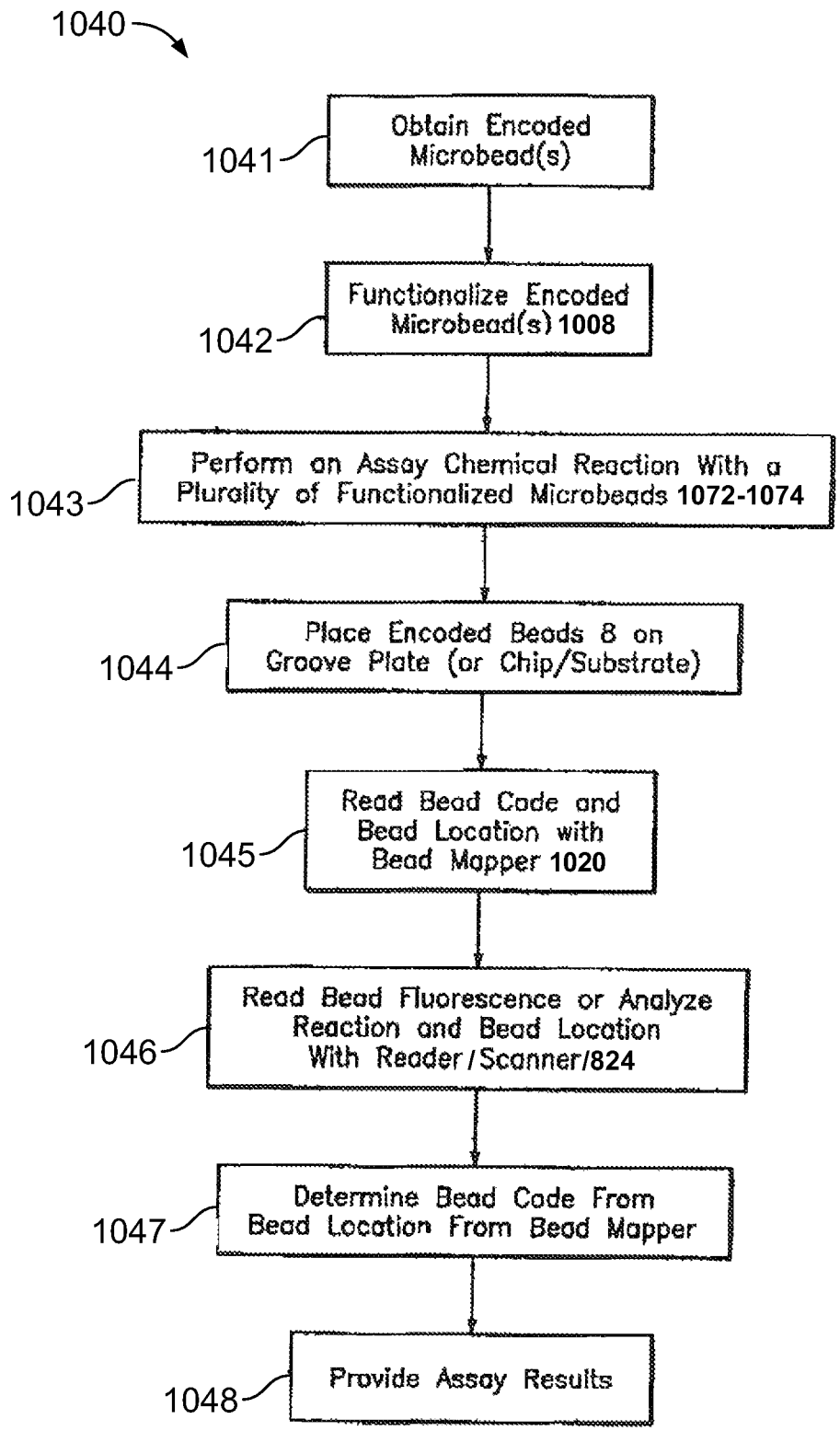
FIG. 14 is a flow chart of a method of using a hybrid random bead/ship based microarray, in accordance with the present invention.
Figure 14A:
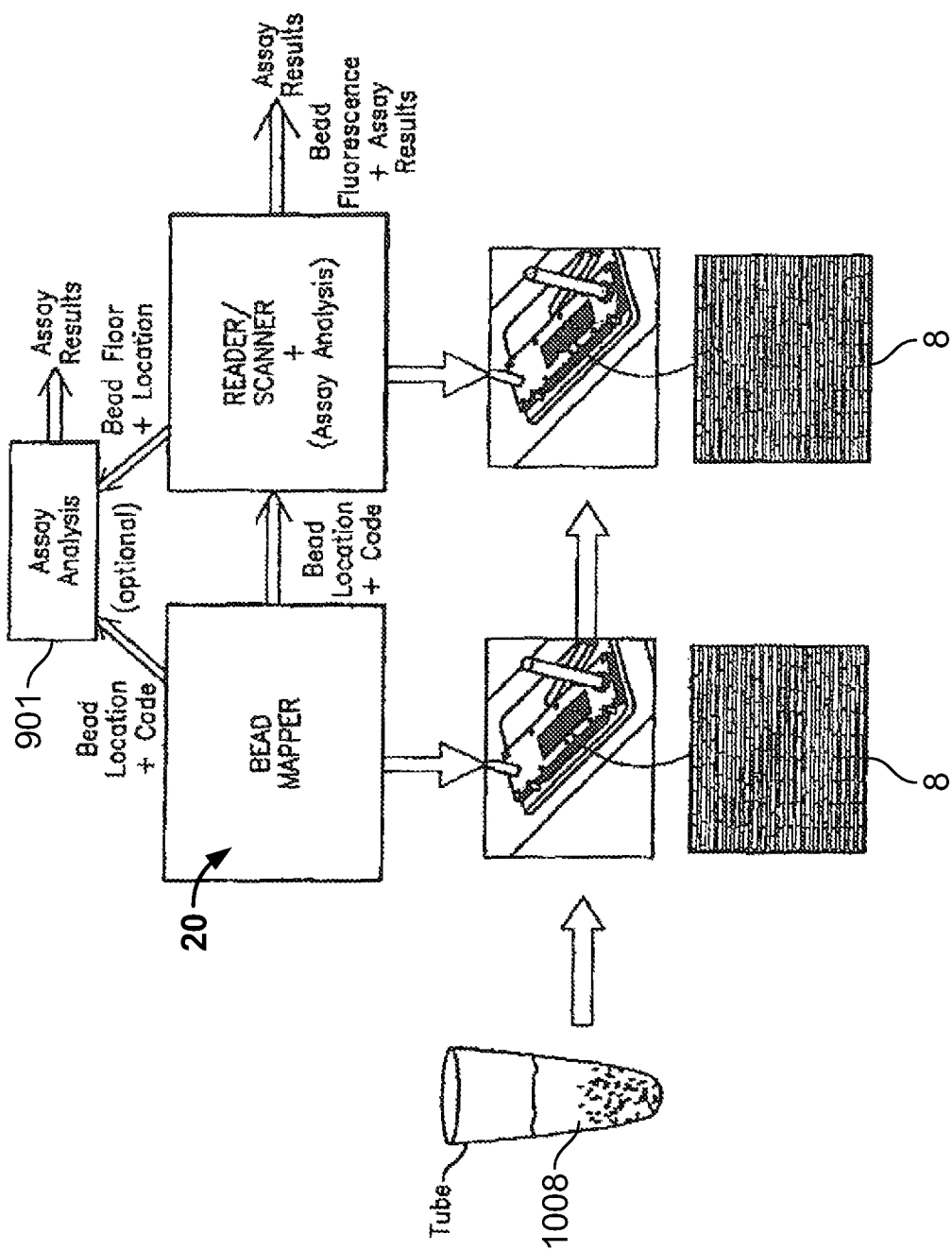
FIG. 14(a) is a schematic pictorial representation showing a way to use a hybrid random bead/ship based microarray, in accordance with the present invention.

Referring to FIGS. 14 and 14(*a*), a procedure 1040 for performing such a multiplexed assay or experiment using the hybrid random bead/chip based microarray includes the steps of obtaining (step 1041) the microbead 1008, as described herein, and functionalizing (step 1042) the substrate 1010 of the microbead 1008 by coating or depositing or growing it with a probe 1076 that will react in a predetermined way with "target" analytes 1052-1054. An assay is then performed (step 1043) with a plurality of functionalized microbeads 1072 with different identification codes 1058 at the same time, e.g., analyte reaction or hybridization, or other multiplexed chemical reaction or experiment. In step 1044, the microbeads 1008 are then placed on a plate, chip or other 2D substrate, which may be contained within a housing, chamber or the like. In step 1045, the chip is provided to a Bead Mapper which reads the bead codes and bead locations on the chip.

Next, in step 1046, the chip is provided to a Reader/Scanner 1824 (FIG. 14(*a*)) where the fluorescence of each of the functionalized/hybridized/reacted microbeads 1072 is analyzed to determine information about the analyte reaction or hybridization for each bead and location. Next a step 1047 determines the code 1058 of each of the beads 1072 from the information from the Bead Mapper, thereby determine which "target" analytes 1052-1054 are present in the solution 1060.

Accordingly, as discussed hereinabove, the assay utilizes the fact that each probe particle (or microbead) is individually identifiable. Once the bead identification code or tag is read, and the spatial position (or location) is known, the self-assembled "chip" can be inserted into a conventional known chip reader or scanner 1824 (FIG. 14(*a*)). The chip reader 1824 reads the fluorescent tags on the target molecules and determines the spatial location of these tags. The fluorescent tag location is then used to identify the bead code (and thus probe identification) at that location from the bead mapping information to complete the assay or chemical experiment.

Examples of known chip readers include the following: Axon Gene Pix Pro 4100 A, GSI/Lumonics/Perkin Elmer Scanner, Alpha Inatech, and others. Other commercial readers or scanners now known or later developed may be used provided it can detect the desired analyte reaction parameter, e.g., fluorescence, etc., and the it can provide the location of same on the substrate.

Alternatively, the reader/scanner 1824 may be similar to the analyte reaction reading and analysis portions of the microbead reader device described in Copending Provisional Patent Application Ser. No. 60/512,302 , entitled "Optical Reader for Diffraction Grating Based Encoded Microbeads", filed Oct. 17, 2003; Ser. No. 60/513,053 , filed Oct. 21, 2003, "Optical Reader for Diffraction Grating Based Encoded Microbeads"; Ser. No. 60/508,038 , "Optical Reader for Diffraction Grating Based Encoded Microbeads", filed Oct. 1, 2003.

Similarly, the Bead Mapper 1020 may be similar to the bead reading/mapping portions of the microbead reader described in Copending Provisional Patent Application Ser. No. 60/512,302 , entitled "Optical Reader for Diffraction Grating Based Encoded Microbeads", filed Oct. 17, 2003; Ser. No. 60/513,053 , filed Oct. 21, 2003, "Optical Reader for Diffraction Grating Based Encoded Microbeads"; Ser. No. 60/508,038 , "Optical Reader for Diffraction Grating Based Encoded Microbeads".

Figures 15, 16:
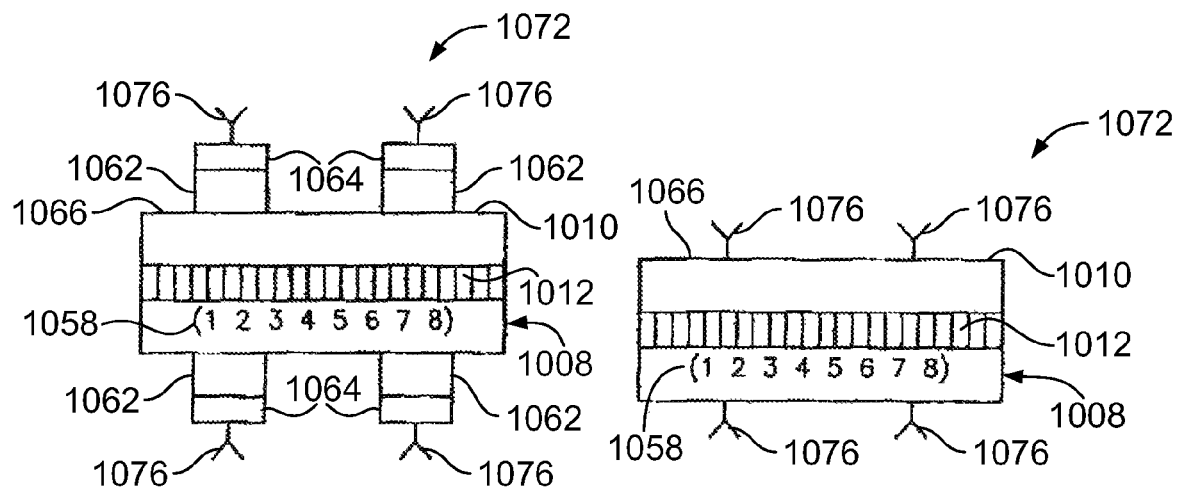
FIG. 15 is a side view of an optical identification element having a substance attached to the outer surface thereof, in accordance with the present invention.
FIG. 16 is a side view of an optical identification element having a substance attached to the outer surface thereof, in accordance with the present invention.

In FIGS. 15 and 16, a functionalized microbead 1072 is shown, wherein the substrate 1010 of the microbead 1008 is coated with a probe 1076 and used in an assay or as an attractant for certain "target" analytes 1052-1054 (see FIG. 17). In one embodiment shown in FIG. 15, the microbead 1008 is coated with a linker molecule or complex 1062 as is known in the art. A molecular group 1064 is attached to the probe 1076 to enable the probe to be bonded to the linker molecule or complex 1062, and thus to the microbead 1008 to form the functionalized microbead 1072. The probe 1076 may include one of an Oligonucleitides (oligos), antibodies, peptides, amino acid strings, cDNA, RNA, chemicals, nucleic acid oligomers, polymers, biological cells, or proteins. For example, the probe 1076 may comprise a single strand of DNA (or portion thereof) and the "target" analyte 1052-1054 comprises at least one unknown single strand of DNA, wherein each different "target" analyte has a different DNA sequence.

Referring to FIG. 16, in some instances, the probe 1076 may be attached directly to the substrate 1010 of the microbead 1008, or directly synthesized (or grown) thereon, such as via phosphoramidite chemistry. Examples of surface chemistry for the functionalized microbeads 1072 include Streptavidin/biotinylated oligos and Aldehyde/amine modified oligos. Other chemistry may be used if desired. Some examples of chemistry are described in Copending Provisional U.S. Patent Application Ser. No. 60/519,932, filed Nov. 14, 2003, entitled, "Diffraction Grating-Based Encoded Microparticles for Multiplexed Experiments". Further, the microbead may be coated with a blocker of non-specific binding (e.g., salmon sperm DNA) to prevent bonding of analytes 1052-1054 (e.g. DNA) to the non-functionalized surface 1066 of the functionalized microbeads 1072.

For example, DNA probe molecules may be directly synthesized on the beads using standard phosphoramidite chemistry with no post synthetic purification, and the beads used as the solid support. The attachment to the bead may be done by preparing the beads using standard linker chemistry coated on the beads that allows the probe to attach to the bead. Then, the oligo probe may be grown base-by-base to create the oligo sequence. Alternatively, the entire desired oligo sequence may be pre-fabricated and then attached to the bead after fabrication. In that case, the linker chemistry used on the bead would likely be different and possibly more complex than the linker chemistry used in direct synthesis. Also, the beads may functionalized as discussed hereinbefore and then placed in a blocker solution of BSA Bovine Serum Albumin (or any other suitable blocker to prevent non-specific binding of the target molecule). The beads may then be hybridized by placing the beads in a hybridization solution. Any desirable hybridization solution may be used. One example is: 5× concentration of SSC (Standard Saline Citrate), 25% formamide, 0.1% SDS (Sodium Dodecyl Sulfate-soap—used to help the beads not stick to the walls of tube), a predetermined amount of complementary DNA (cDNA) to the sequence of a given Probe tagged with Cy3 fluorescent molecules, and a predetermined amount of complementary DNA (cDNA) to the sequence of that Probe tagged with Cy5 fluorescent molecules. Any other hybridization or analyte reaction technique may be used if desired.

Referring to FIG. 17, for illustrative purposes reference numerals 1052, 1053, 1054, 1060, 1070, 1072, 1073, and 1074 are shown in FIG. 17 as '52, '53, '54, '60, '70, '72, '73, and '74, respectively. An assay is performed by adding a solution '60 of different types of "target" analytes '52-'54 into a cell or container '70 having a plurality of functionalized microbeads '72-'74 disposed therein. As discussed in step 1046 of FIG. 14, the functionalized microbeads '72-'74 placed in the cell '70 have different identification codes '58 that correspond to unique probes '76-'78 bonded thereto. For example, all functionalized microbeads '72 disposed within the cell '70 having an identification code of 12345678 is coated with a unique probe '76. All functionalized microbeads '73 disposed within the cell '70 having an identification code of 34128913 is coated with a unique probe '77. All functionalized microbeads '74 disposed within the cell '70 having an identification code of 11778154 is coated with a unique probe '78.

The "target" analytes '52-'54 within the solution '60 are then mixed with the functionalized microbeads '72-'74. During the mixing of the "target" analytes '52-'54 and the functionalized microbeads '72-'74, the "target" analytes attach to the complementary probes '76-'78, as shown for functionalized microbeads '72,'73 having codes 12345678 and 34128913. Specifically, as shown in FIG. 17, "target" analytes '53 bonded with probes '76 of the functionalized microbeads '72 having the code 12345678, and "target" analytes '52 bonded with probes '77 of the functionalized microbeads '73 having the code 34128913. On the other hand, "target" analytes '54 did not bond with any probes, and not "target" analytes '52-'54 in the solution '60 bonded with probes '78 of the functionalized microbeads '74 having the code 11778154. Consequently, knowing which "target" analytes attach to which probes along with the capability of identifying each probe by the encoded microbead, the results of the assay would show that the unknown "target" analytes in the solution '60 includes "target" analytes '53, '54, as will be described in further detail.

For example as discussed hereinbefore, each coded functionalized microbead '72-'74 has a unique probe '76-'78, respectively bonded thereto, such as a portion of a single strand of DNA. Similarly, the "target" analytes '52-'54 comprise a plurality of unknown and unique single strands of DNA. These "target" analytes '52-'54 are also processed with a fluorescent, such as dyeing, such that the test molecules illuminate. As will be discussed hereinafter, the fluorescence of the "target" analytes provide the means to identify, which functionalized microbeads '72-'74 have a "target" analyte attached thereto.

Once the reaction or combining or hybridization is complete, the functionalized (or reacted or hybridized) microbeads '72-'74 are rinsed off with a saline solution to clean off the uncombined "target" analytes '52-'54.

Figure 18:
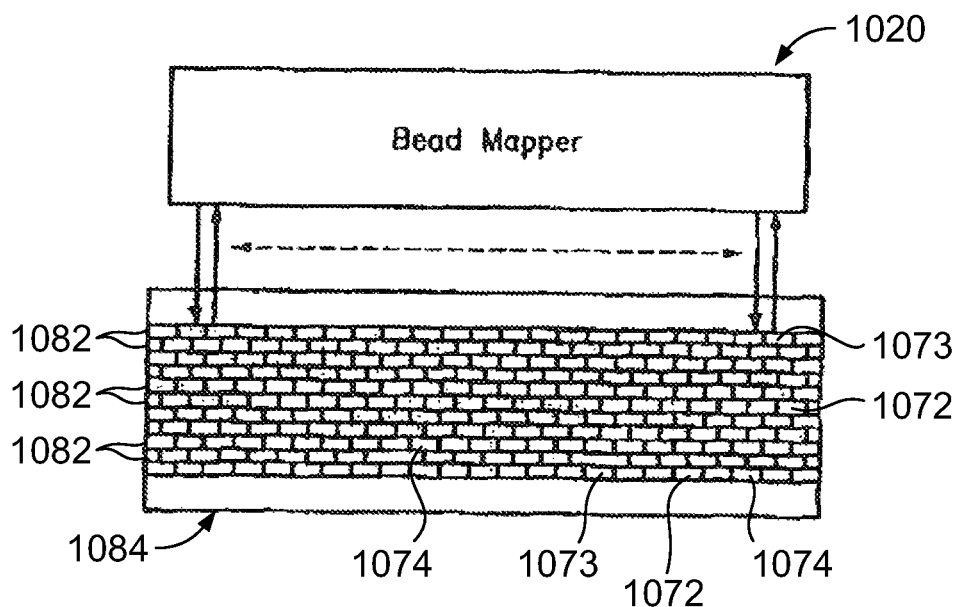
FIG. 18 is a schematic view of plurality of optical identification elements, aligned in a plurality of grooves, disposed on a substrate, and a Bead Mapper that scans each optical identification element for determining the code and location of each optical identification element, in accordance with the present invention.

Referring to FIG. 18, as discussed herein, the functionalized microbeads 1072-1074 may be placed on a tray, plate, or substrate (or "chip") 1084 with grooves 1082 to allow the microbeads to be aligned in a predetermined direction, such as that described in U.S. Patent Appl. Publ. No. 2004/0233485, filed Sep. 12, 2003, and U.S. patent application Ser. No. 10/661,836 (U.S. Patent Appl. Publ. No. 2004/0132205), filed Sep. 12, 2003, which are both incorporated herein by reference. The grooves 1082 may have holes (not shown) that provide suction to keep the functionalized microbeads in position. Once aligned in the tray 1084, the functionalized microbeads 1052-1054 are individually scanned and analyzed by the bead detector 1020.

Figure 19:
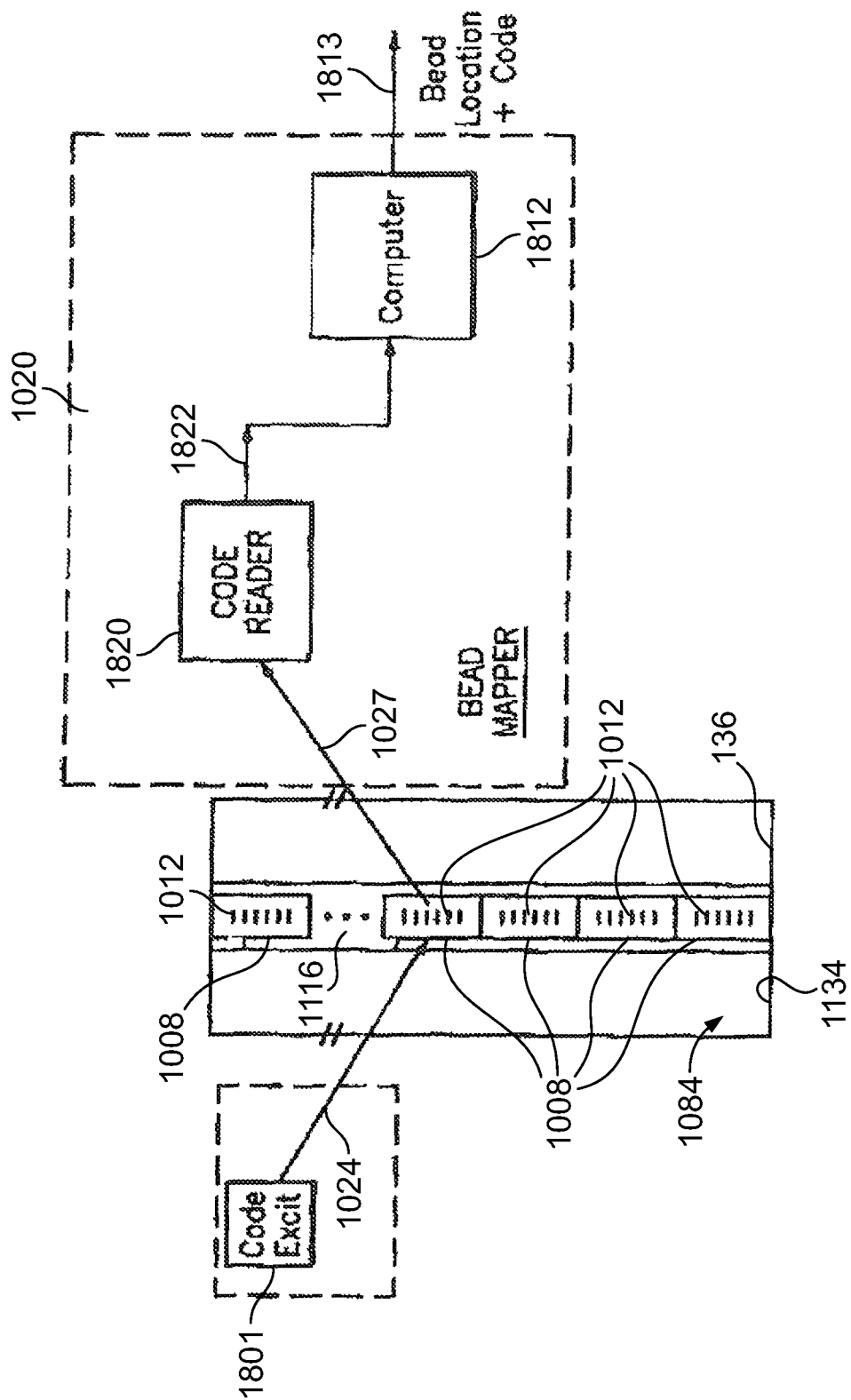
FIG. 19 is a side view of an optical identification element, and a more detailed view of a Bead Mapper that determines the code and location of the optical identification element, in accordance with the present invention.

Referring to FIGS. 18 and 19, then, each functionalized microbead 1072-1074 is read by a Bead Mapper 1020 to determine the identification code 1058 of each of the functionalized microbeads and the location of each bead.

Referring to FIG. 19, more specifically, as discussed herein and in the aforementioned patent applications, the codes in the microbeads 1008 are detected when illuminated by incident light 1024 which produces a diffracted or output light signal 1027 to a reader 1820, which includes the optics and electronics necessary to read the codes in each bead 1008, as described herein and/or in the aforementioned copending patent application. The reader 1820 provides a signal on a line 1822 indicative of the code in each of the bead 1008 to a known computer 1811. The incident light 1024 may be directed transversely from the side of the tray 1084 (or from an end or any other angle) with a narrow band (single wavelength) and/or multiple wavelength source, in which case the code is represented by a spatial distribution of light and/or a wavelength spectrum, respectively, as described hereinafter and in the aforementioned copending patent application. Other illumination, readout techniques, types of gratings, geometries, materials, etc. may be used for the microbeads 1008, as discussed hereinafter and in the aforementioned patent application. The computer 1811 provides an output signal on a line 1813 indicative of the bead location and code.

Figure 20:
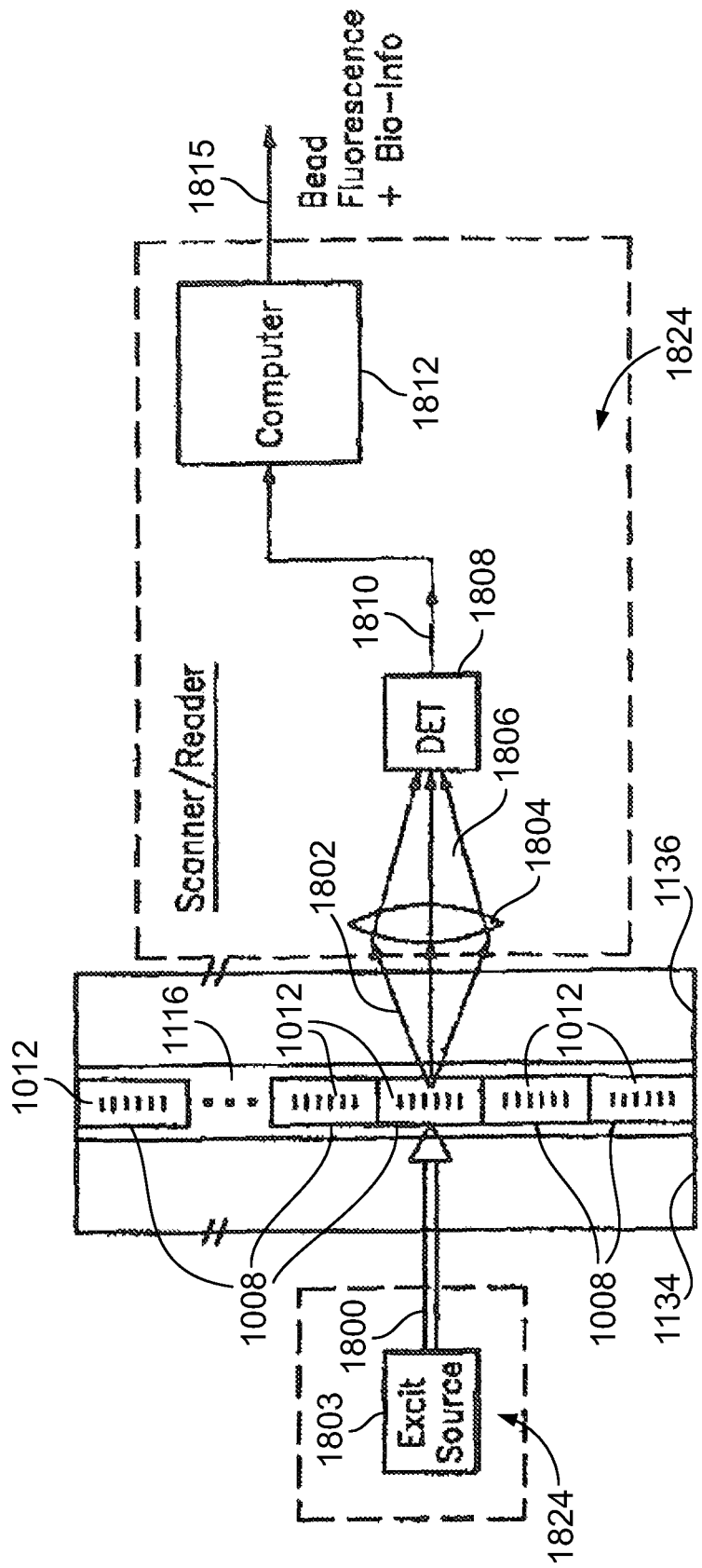
FIG. 20 is a side view of an optical identification element after the performance of an assay, and a more detailed view of a Reader/Scanner that reads the fluorescence and location of the optical identification element, in accordance with the present invention.
Figure 21:
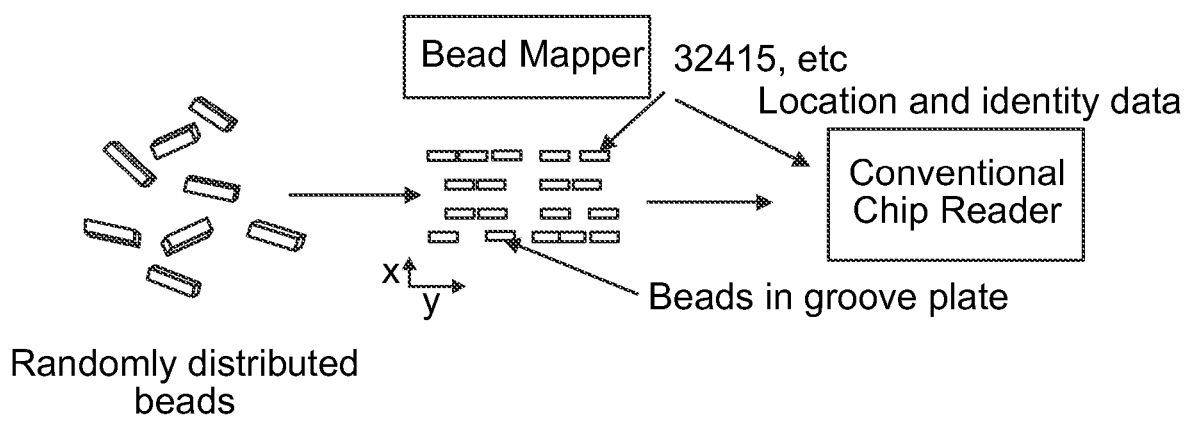
FIG. 21 illustrates a hybrid random bead/chip approach in which the beads are randomly distributed.

Referring to FIG. 20, the slide, tray or chip 1084 is then placed in a reader or scanner 1824 (also see FIG. 14(*a*)). The reader 1824 reads each functionalized microbead 1072-1074 for fluorescence or other indicator of the analyte reaction.

A light source (not shown) may be provided to illuminate the microbeads 1072-1074. Once the fluorescent microbeads 1072-1074 are identified and knowing which probe 1076-1078 (or single strand of DNA) was attached to each coded, functionalized microbead 1072-1074, the bead detector 1020 determines which "target" analytes 1052-1054 were present in the solution 1060. As described hereinbefore, the bead detector 1020 illuminates the functionalized microbeads 1072-1074 and focuses light 1026 reflected by the diffraction grating 1012 onto a CCD array or camera 1032, whereby the code 1058 of the functionalized microbead 1072-1074 is determined. Secondly, the reader 1824 includes a fluorescence detector 1086 for measuring the fluorescence emanating from "target" analytes 1052-1054 attached to the probes 1076-1078. The fluorescence meter 1086 includes a lens 1088 and optical fiber 1090 for receiving and providing the fluorescence from the "target" analyte 1052-1054 to the fluorescence meter.

Referring to FIG. 20, for assays that use fluorescent molecule markers to label or tag chemicals, an optical excitation signal 1800 is incident on the microbeads 1008 through the tray 1084 and a fluorescent optical output signal 1802 emanates from the beads 1008 that have the fluorescent molecule attached. The fluorescent optical output signal 1802 passes through a lens 1804, which provides focused light 1802 to a known optical fluorescence detector 1808. Instead of or in addition to the lens 1802, other imaging optics may be used to provide the desired characteristics of the optical image/signal onto the fluorescence detector 1808. The detector 1808 provides an output signal on a line 1810 indicative of the amount of fluorescence on a given bead 1008, which can then be interpreted to determine what type of chemical is attached to the bead 1010.

The tray 1084 is made of glass or plastic or any material that is transparent to the code reading incident beam 1024 and code reading output light beams 1027 as well as the fluorescent excitation beam 1800 and the output fluorescent optical signal 1802, and is properly suited for the desired application or experiment, e.g., temperature range, harsh chemicals, or other application specific requirements.

The code signal 1822 from the bead code reader 1820 and the fluorescent signal 810 from the fluorescence detector are provided to a known computer 1812. The computer reads the code associated with each bead and determines the chemical probe that was attached thereto from a predetermined table that correlates a predetermined relationship between the bead code and the attached probed. In addition, the computer 1812 reads the fluorescence associated with each bead and determines the sample or analyte that is attached to the bead from a predetermined data that correlates a predetermined relationship between the fluorescence tag and the analyte attached thereto. The computer 1812 then determines information about the analyte and/or the probe as well as about the bonding of the analyte to the probe, and provides such information on a display, printout, storage medium or other interface to an operator, scientist or database for review and/or analysis, as indicated by a line 1815.

Generally, the assay of the present invention may be used to carry out any binding assay or screen involving immobilization of one of the binding agents. Such solid-phase assays or screens are well known in the chemical and biochemical arts. For example, such screening may involve specific binding of cells to a molecule (e.g. an antibody or antigen) immobilized on a microbead in the assay followed by analysis to detect whether or to what extent binding occurs. Alternatively, the beads may subsequently removed from the groove plate for sorting and analysis via flow cytometry (see e.g. by Needels et al. (1993). Examples of biological compounds that may be assayed or screened using the assay of the present invention include, e.g. agonists and antagonists for cell membrane receptors, toxins, venoms, viral epitopes, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles. In addition, the present invention may be used in any of a large number of well-known hybridization assays where nucleic acids are immobilized on a surface of a substrate, e.g. genotyping, polymorphism detection, gene expression analysis, fingerprinting, and other methods of DNA- or RNA-based sample analysis or diagnosis.

Any of the great number of isotopic and non-isotopic labeling and detection methods well-known in the chemical and biochemical assay art may be used to detect binding with the present invention. Alternatively, spectroscopic methods well-known in the art may be used to determine directly whether a molecule is bound to a surface coating in a desired configuration. Spectroscopic methods include e.g., UV-VIS, NMR, EPR, IR, Raman, mass spectrometry and other methods well-known in the art. For example, mass spectrometry also is now widely employed for the analysis of biological macromolecules. The method typically involves immobilization of a protein on a surface of substrate where it is then exposed to a ligand binding interaction. Following ligand binding (or non-binding) the molecule is desorbed from the surface and into a spectrometer using a laser (see, e.g. Merchant and Weinberger, "Recent advancements in surface-enhanced laser desorption/ionization-time of flight-mass spectrometry," Electrophoresis 21: 1164-1177 (2000)). The microbeads in the assay of the present invention may be used as substrates in the mass spectrometry detection methods described above.

Various aspects of the present invention may be conducted in an automated or semi-automated manner, generally with the assistance of well-known data processing methods. Computer programs and other data processing methods well known in the art may be used to store information including e.g. microbead identifiers, probe sequence information, sample information, and binding signal intensities. Data processing methods well known in the art may be used to read input data covering the desired characteristics.

The invention may be used in many areas such as drug discovery, functionalized substrates, biology, proteomics, combinatorial chemistry, DNA analysis/tracking/sorting/tagging, as well as tagging of molecules, biological particles, matrix support materials, immunoassays, receptor binding assays, scintillation proximity assays, radioactive or non-radioactive proximity assays, and other assays, (including fluorescent, mass spectroscopy), high throughput drug/genome screening, and/or massively parallel assay applications. The invention provides uniquely identifiable beads with reaction supports by active coatings for reaction tracking to perform multiplexed experiments.

Some current techniques used in combinatorial chemistry or biochemistry are described in U.S. Pat. No. 6,294,327, entitled "Apparatus and Method for Detecting Samples Labeled With Material Having Strong Light Scattering Properties, Using Reflection Mode Light and Diffuse Scattering", issued Sep. 23, 2001 to Walton et al.; U.S. Pat. No. 6,242,180, entitled "Computer Aided Visualization and Analysis System for Sequence Evaluation", issued Jun. 5, 2001, to Chee; U.S. Pat. No. 6,309,823 entitled "Arrays of Nucleic Acid Probes for Analyzing Biotransformation of Genes and Methods of Using the Same", Oct. 30, 2001, to Cronin et al.; U.S. Pat. No. 6,440,667, entitled "Analysis of Target Molecules Using an Encoding System"; U.S. Pat. No. 6,355,432, entitled "Products for Detecting Nucleic Acids"; U.S. Pat. No. 6,197,506, entitled "Method of Detecting Nucleic Acids"; U.S. Pat. No. 6,309,822, entitled "Method for comparing copy number of nucleic acid sequences"; U.S. Pat. No. 5,547,839, entitled "Sequencing of surface immobilized polymers utilizing micro-fluorescence detection", U.S. Pat. No. 6,383,754, entitled "Binary Encoded Sequence Tags", and U.S. Pat. No. 6,383,754, entitled "Fixed Address Analysis of Sequence Tags", which are all incorporated herein by reference to the extent needed to understand the present invention.

The invention can be used in combinatorial chemistry, active coating and functionalized polymers, as well as immunoassays, and hybridization reactions. The invention enables millions of parallel chemical reactions, enable large-scale repeated chemical reactions, increase productivity and reduce time-to-market for drug and other material development industries.

As discussed hereinbefore, although a fluorescent label is probably most convenient, other sorts of labels, e.g., radioactive, enzyme linked, optically detectable, or spectroscopic labels may be used. An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemilumenescence would be preferred but is not required. Other detection systems may be adapted to the purpose, e.g., electron microscopy, scanning electron microscopy (SEM), scanning tunneling electron microscopy (STEM), infrared microscopy, atomic force microscopy (AFM), electrical conductance, and image plate transfer.

Scope of the Invention

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

Moreover, the invention also comprises features of construction, combination of elements, and arrangement of parts which will be exemplified in the construction hereinafter set forth.

It will thus be seen that the objects set forth above, and those made apparent from the preceding description, are efficiently attained and, since certain changes may be made in the above construction without departing from the scope of the invention, it is intended that all matter contained in the above description or shown in the accompanying drawing shall be interpreted as illustrative and not in a limiting sense.

Subject Matter from U.S. Provisional App. No. 60/441,678:

We describe here a hybrid approach to the random bead assay and the traditional fixed chip approach.

The basic idea is to have the probes freely movable during the analyte reaction process. The reacted probes are then placed onto a substrate (or slide) and are mapped and identified by a separate Bead Mapper device. This map can then be used in a conventional chip reader.

This assay relies on the fact that each probe particle is individually identifiable. Once the identification code or tag is read, and the spatial position (or location) is known, the self-assembled "chip" can be inserted into a conventional known chip reader. The chip reader reads the fluorescent tags on the target molecules and determines the spatial location of these tags. The tag location is then used to identify the bead code (and thus probe identification) at that location from the bead mapping information to complete the assay or chemical experiment. After reading the chip, the beads may be removed from the chip for further or alternative processing or experiments. If desired, the chip substrate and/or the beads may be reused in other experiments or assays.

Alternatively, the beads (or probe particles) can be assembled into a 2-D (chip) format before the analyte reaction process. In that case, the analyte can be applied to the chip with the beads disposed thereon.

One specific embodiment of interest is when the particles have a cylindrical shape and are 10-100's of microns in feature size. These beads can be ordered and oriented by using a microscope slide with mechanical grooves cut into the surface.

Such a bead-based system is described in the aforementioned patent applications, U.S. Provisional Patent Application Ser. No. 60/405,087 and U.S. Provisional Patent Application Ser. No. 60/410,541 . In that case, an optical identification element (or bead or microbead) comprises a known optical bead substrate, having a Bragg grating impressed (or embedded or imprinted) in the bead substrate. The microbead has an outer diameter of about 125 microns and comprises silica glass (SiO2) having the appropriate chemical/material composition to allow a Bragg grating to be disposed therein or thereon. The bead may be made from any material capable of having a Bragg grating disposed therein. Other materials and dimensions for the bead may be used if desired. For example, it may be made of any glass, e.g., silica, phosphate glass, or other glasses, or made of glass and plastic, or solely plastic. For high temperature or harsh chemical applications, a bead made of a glass material is desirable.

The bead may also be made from an optical waveguide, e.g., a standard telecommunication single mode optical fiber (125 micron diameter or 80 micron diameter fiber), or a large diameter (greater than 0.3 mm outer diameter) single mode waveguide. In that case, any type of optical waveguide may be used for the bead, such as, a multi-mode, birefringent, polarization maintaining, polarizing, multi-core, or multi-cladding optical waveguide, or a flat or planar waveguide (where the waveguide is rectangular shaped), or other waveguides. Also, it is not required that the bead be an optical waveguide (i.e., capable of guiding light along its length) as long as it has a Bragg grating disposed therein.

The Bragg grating, as is known, is a periodic or aperiodic variation in the effective refractive index and/or effective optical absorption coefficient of an optical waveguide, such as that described in U.S. Pat. Nos. 4,725,110 and 4,807,950, entitled "Method for Impressing Gratings Within Fiber Optics", to Glenn et al; and U.S. Pat. No. 5,388,173, entitled "Method and Apparatus for Forming Aperiodic Gratings in Optical Fibers", to Glenn, which are hereby incorporated by reference to the extent necessary to understand the present invention. However, any grating or reflective element embedded, etched, imprinted, or otherwise formed in the bead may be used if desired.

The bead with the grating has a length L and an outer diameter D1. The length L can range from small (about 100-300 microns or smaller) to large (greater than 1.0-100 mm or greater). In addition, the diameter D1 can range from small (less than 80 microns) to large (greater than 1.0-100 mm). Other lengths L and diameters D1 may be used if desired. The invention is not limited by the dimensions. Also, geometries other than a cylinder may be used, e.g., rectangular, square, D-shaped, spherical, and others, such as is described in the aforementioned patent applications. The dimensions L and D1, materials, and material properties of the bead are selected such that the desired optical and material properties are met for a given application. The resolution and range for the optical codes are scalable by controlling these parameters. Also, the axial end faces of the bead may be coated with a material that reduces optical scatter if desired. Also, the end faces need not be perfectly straight and perpendicular to the sides for side illumination. The grating may have a length of about the length of the bead. Alternatively, the length L of the bead may be longer than the length of the grating. Other dimensions and lengths for the bead and the grating may be used.

Ultimately, this technique could be viewed as a "chip" or "microchip" approach where the probes (or beads) are assembled from many individually fabricated parts. The beads may be ordered in one dimension along the grooves, but are randomly distributed (but oriented) along each groove. However, any technique may be used that allows the bead location to be identified.

This self-assembled "chip" approach has many advantages over conventional bead based assays. In particular, since the beads are fixed on a chip substrate, they may be examined at any time. Also, beads of interest can be easily removed and sorted from the plate/chip after an experiment is performed. Further, a fixed plate format is easier to use in experiments that vary the temperature. Still further, a fixed plate format allows convenient use of a standard chip reader to examine the beads. Also, the beads do not need to be examined using a flow cytometer.

The dimensions and geometries for any of the embodiments described herein are merely for illustrative purposes and, as such, any other dimensions may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

Figure 22:
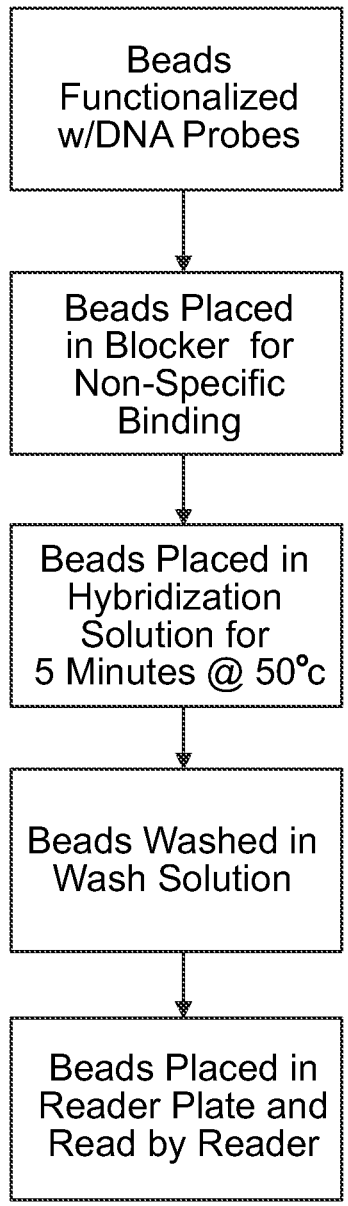
FIG. 22 shows a flow chart for an assay that may be performed with the beads discussed herein.

Subject Matter from U.S. Provisional App. No. 60/519,932:

Referring to FIG. 22, a flow chart for an assay that may be performed with the beads discussed herein is shown. In particular, an assay was performed with cylindrically shaped glass beads as discussed herein, having dimensions of about 400 microns by 65 microns, using 9 different bead codes (1106, 2090, 8740, 4424, 682, 2470, 2389, 2454, and 618) and about 20 to 30 beads of each code. In addition, there were four different oligonucleotide (or DNA or oligo) probes, Probe #1, Probe #2, Probe #3, Probe #4, attached to a corresponding four different beads each having unique codes, 1106, 2090, 8740, 4424, respectively. The five remaining bead codes, 682, 2470, 2389, 2454, 618, were did not have a DNA probe attached thereto and were used as a control in the assay. Table 1 below shows the bead codes, the DNA probe sequence and Probe # attached to the bead and the melt temperature (Tm) of each DNA probe as it relates to binding affinity strength with respect to Probe #1. Probes #1-4 were randomly selected to provide a variety of different melt temperatures, and thus varying amounts of binding affinity strength difference between the four DNA Probes.

TABLE 1

| Bead Code | DNA Probe Sequence (26-mer; 26 bases long) | Probe # | Tm(C) |
|---|---|---|---|
| 1106 | 5'-GCGTTTTACAATAACTTCTCGTGCCA-Spacer18-3'-Bead | 1 | 66.05 |
| 8740 | 5'-GCGTTATAGATTAACCTCTCCTGCCA-Spacer18-3'-Bead | 2 | 34.55 |
| 4424 | 5'-TCAAAATACCATTGCAGCTACCATTT-Spacer18-3'-Bead | 3 | -1.85 |
| 2090 | 5'-GTGCGTTTTACAATAACTTCCGTGCG-Spacer18-3'-Bead | 4 | 55.35 |
| 682 | None (Control) | N/a | N/a |
| 2470 | None (Control) | N/a | N/a |
| 2389 | None (Control) | N/a | N/a |
| 6454 | None (Control) | N/a | N/a |
| 618 | None (Control) | N/a | N/a |

More specifically, four 26 mer (26 base long) DNA probe molecules were directly synthesized on the respective beads shown in Table 1 using standard phosphoramidite chemistry with no post synthetic purification, and the beads were used as the solid support. The 3' and 5' refer to the ends of the DNA probe strands (or oligo strands). The 3' end of the oligo strand was attached to the bead, followed by a carbon spacer molecule (Spacer18) between the 3' end and the oligo sequence, as shown in Table 1. The attachment to the bead was done by preparing the beads using standard linker chemistry coated on the beads that allows the probe to attach to the bead. Then, the oligo probe is grown base-by-base to create the oligo sequence shown in Table 1. Alternatively, the entire desired oligo sequence may be pre-fabricated and then attached to the bead after fabrication. In that case, the linker chemistry used on the bead would likely be different and possibly more complex than the linker chemistry used in direct synthesis.

In an experiment, the beads were functionalized as discussed hereinbefore and then the beads were placed in a blocker solution of BSA Bovine Serum Albumin (or any other suitable blocker to prevent non-specific binding of the target molecule The beads are then hybridized by placing the beads in a hybridization solution comprising: 5× concentration of SSC (Standard Saline Citrate), 25% formamide, 0.1% SDS (Sodium Dodecyl Sulfate-soap—used to help the beads not stick to the walls of tube), 20 nanomoles (nm) of complementary DNA (cDNA) to the sequence of Probe #1 tagged with Cy3 fluorescent molecules, and 20 nanomoles (nm) of complementary DNA (cDNA) to the sequence of Probe #1 tagged with Cy5 fluorescent molecules.

The Cy3 and Cy5 labeled molecules are the target molecules for the assay and are designed to be the complement to the sequence of Probe #1. The other Probes #2,#3,#4 are designed to provide varying levels of binding affinity to a target that would bind strongly to Probe #1. In particular, Probe #4 (code 2090) was designed to be only slightly different from Probe #1 (close melt temperature 55.35 deg. C. to that of Probe #1), Probe #2 (code 8740) was designed to be even more different from Probe #1 and thus have a melt temp. lower than Probe #2, 34.55 deg. C., and Probe #3 (code 4424) was designed to have a sequence much different from Probe #1, and thus a very low melt temp. −1.85 deg. C.

The hybridization was then performed at 50 deg. C. for a period of about 5 minutes. Other shorter or longer times may be used if desired. Then, the beads were washed first in a solution of 1×SSC and then in a reduced concentration 0.2× SSC. No centrifugation is required to remove water from the beads, as they sink to the bottom of the solution.

Figure 23:
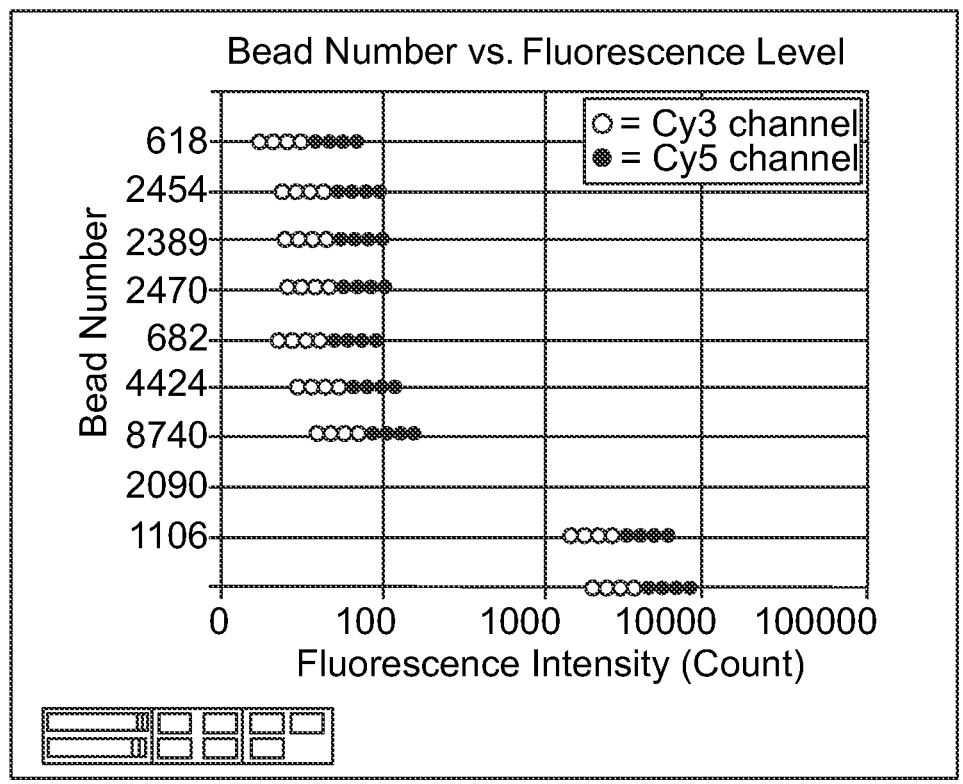
FIG. 23 is a graph illustrating an amount of Cy3 and Cy5 molecules attached to each bead code by showing the intensity of the Cy3 and Cy5 fluorescence (in counts).

Referring to FIG. 23, the amount of Cy3 and Cy5 molecules attached to each bead code is shown by showing the intensity of the Cy3 and Cy5 fluorescence (in counts). The graph shows that bead number 1106, which had Probe #1 attached, had the highest level of fluorescence, because the target molecules were designed to be the complementary to and thus have a strong affinity to Probe #1. Bead number 2090 had Probe #4 attached thereto and exhibited slightly lower fluorescence level than for Probe #1, as it had a slight mismatch from Probe #1. Bead number 8740 had Probe #2 attached thereto and exhibited a significantly lower fluorescence level than for Probe #1, as the it had a significant mismatch from Probe #1. Bead number 4424 had Probe #3 attached thereto and exhibited an even lower fluorescence level than Probe #2 from the level of Probe #1, as the it had a very significant mismatch from Probe #1. Finally, the control beads having codes 682, 2470, 2389, 2454, 618, all show a background fluorescence level below all the beads having probes attached. Thus, the codes can be read with the chemistry and fluorescent molecules being attached to the beads. For each bead, there will be a Cy3 (green) and a Cy5 (red) fluorescence (i.e., a red-green fluorescent data pair).

In addition, the data shows that each bead may have slightly different fluorescence intensity or count level. Because the beads allow for a high number (greater than 50 million) codes, if desired, each bead may be labeled, even ones that have the same probe sequence. This would allow for evaluation of signals from each bead, thereby allowing better quality control of the data provided. For example, the graph for code 1106 has a red-green pair of points (probably from the same bead) that is much lower level than the other points on the graph. If each bead was labeled with a separate unique code, one could know exactly which bead exhibited this characteristic, and the bead could then be re-analyzed to determine if there was a problem with the chemistry on the bead, e.g., that the bead did not have the correct Probe put on it. This allows for quality control to be performed on the beads to enhance data credibility and accountability.

Figure 24:
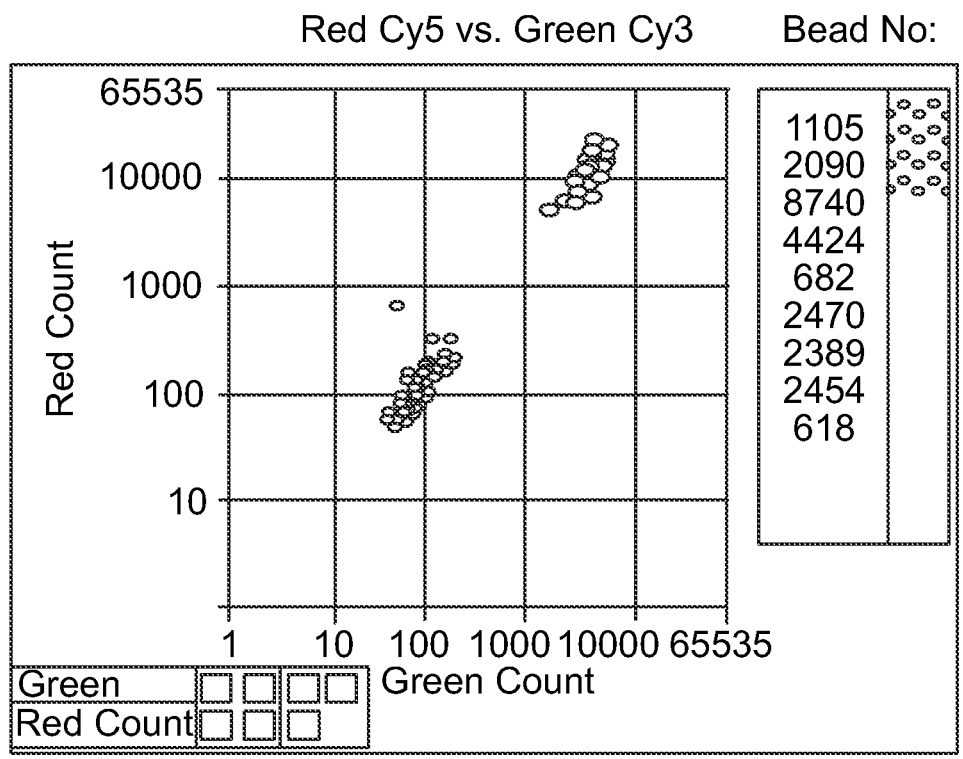
FIG. 24 shows the data of FIG. 23 plotted as the red Cy5 intensity against the green Cy3 intensity.

Referring to FIG. 24, the data in FIG. 23 is plotted as the red Cy5 intensity against the green Cy3 intensity. The Yellow dots represent the beads having the four Probes #1-#4 and the Red points represent the beads having no Probes on them. This plot shows the relative level of green and red fluorescence on a given bead, and thus the uniformity of distribution of red and green tagged molecules on the beads. When the point fall along a straight line, the distribution of red and green molecules on each of the beads is substantially uniform, as is shown substantially in FIG. 40. The more like a straight line, the better the quality of the data with respect to uniformity. Accordingly, the assay of the present invention show high uniformity. Further, as discussed before, if there are points that fall outside the desired field for quality data, if each of the beads are labeled with a unique code, those beads can be re-examined to further evaluate the anomaly.

Subject Matter from U.S. Provisional App. No. 60/546,445:

In its broadest sense, the present invention provides a new and unique optical identification element (also known herein as a microbead) made from pieces of an optical fiber or substrate that includes an inner core or region being surrounded by an outer cladding region, the optical fiber or substrate having an identification code imparted therein containing coded information. The identification code may be in the form of a Bragg grating inscribed or written in either the inner core or outer cladding.

The optical identification element may be microscopic in size having a length in a range of 1-1,000 microns or smaller; or for larger applications may have a length of 1.0-1,000 millimeters or more. The outer diameter may be as small as less than 1,000 microns, as well as in a range of 1.0 to 1,000 millimeters for larger applications. Using manufacturing techniques developed in conjunction with the development of the present invention, one optical fiber or substrate can be drawn and processed to produce hundreds of thousands, as well as even a million or more of such unique microbeads.

Microbead Using Conventional Waveguide Technology

In one embodiment, the optical identification element may be manufactured from a conventional waveguide used in the telecommunications industry in which the refractive index of the core is higher than the cladding using, for example, the technique shown and described in U.S. Patent Appl. Publ. No. 2004/0233485, which is hereby incorporated by reference, as well as other techniques described below. In this case, the Bragg grating is written in the core of the conventional waveguide.

In this embodiment, conventional waveguides are used that are known in the art and used in the telecommunications industry, which are made from optical fiber (e.g. 125 micron optical fiber). Conventional fiber Bragg gratings are primarily formed in single mode fibers and are used for coupling forward propagating modes into backward propagating modes. The coupled modes are confined to propagate in the core region of the fiber along its axis; such a constraint defines a waveguide. If only one mode is allowed to propagate then the fiber is called a single mode waveguide, if two or more modes are permitted to propagate the fiber is referred to as a multi-mode waveguide. Key to the function of guiding any number of modes in a fiber is the existence of both a core region and a cladding region, where the refractive index of the core is higher than the cladding. Conditions for single mode propagation are met when the V number of the fiber is less than 2.405, larger values will result in more than one mode. The V number is related to the geometry and refractive indices of the core and clad by the following relationship:

$$V := \frac{2\pi \cdot a \cdot NA}{\lambda c}$$

$$NA := \sqrt{n1^2 - n2^2}$$

where n1 and n2 are the refractive indices of the core and clad respectively. Practical single mode fibers are restricted to NA's in the range of 0.05 to 0.3. Fibers on the high end of the NA range have extremely small core diameters, ranging from 1 to 3 microns, while fibers on the low end of the range have larger cores, but their sensitivity to bend loss increases substantially. As the NA approaches zero, the fiber behaves less and less like a waveguide, which is inconsistent with the stringent demands of the telecommunications industry.

The broad list of devices and applications of fiber Bragg gratings has thus far been restricted to operation in single or few moded fibers; these include band pass optical filters, strain sensors, dispersion compensators, and gain flattening filters. In addition to the technique shown and described in U.S. Patent Appl. Publ. No. 2004/0233485, the following list includes United States patents relate to techniques for forming Bragg gratings in a conventional telecommunications waveguides:
1. U.S. Pat. No. 5,367,588—Method of fabricating Bragg gratings using a silica glass phase grating mask and mask used by same, Ken Hill;
2. U.S. Pat. No. 5,327,515—Method for forming a Bragg grating in an optical medium, Dana Anderson; and
3. U.S. Pat. No. 5,351,321—Bragg grating made in optical waveguide, Elias Snitzer, which are all hereby incorporated by reference.

Microbead Using a New and Unique Optical Substrate

However, using such a conventional telecommunications waveguide to make such optical identification elements may be expensive to manufacture because the manufacturing techniques for making conventional telecommunications waveguides involve drawing optical fiber from a preform under strict predefined optical conditions so as to produce optical fiber having strict predetermined optical characteristics. Moreover, using such a conventional telecommunications waveguide to make such optical identification elements may also be expensive to manufacture because the manufacturing techniques for making such conventional telecommunications waveguides involving writing strong gratings in the optical fiber with grating writing techniques requiring very precise and expensive lasers in order to meet the demands of the telecommunications industry. In view of this, the inventors have also developed an alternative optical identification element in which a substrate is used such as an optical substrate having the refractive index of the core is less than or equal to the cladding, that has important advantages in that it is less expensive to manufacture than when using the conventional waveguide technology otherwise used in the telecommunications industry.

In this alternative embodiment, the optical identification element is manufactured using, for example, the technique shown and described in U.S. Patent Appl. Publ. No. 2004/0233485, as well as other techniques described herein. Since in typical usage, the optical identification element are interrogated from the side in order to read the coded information contain in the Bragg grating, the Bragg grating may be written not only in the core, but also in the cladding.

The microbeads in the alternative embodiment can be manufactured using the same process for inscribing Bragg gratings as those described in some of the above patents. Moreover, due to fact that the beads are interrogated from the side, it is not necessary that the optical substrate be manufactured to perform as a conventional waveguide. It is also well known that the incorporation of Boron as a dopant enhances the photosensitivity of the optical substrate to UV radiation. Boron is also known as an index depressor when it is incorporated into silica glass. When designing a single mode waveguide the amount of Boron is usually very carefully balanced with Germanium to provide the correct index profile in conjunction with enhanced photosensitivity. Again, because the requirement for waveguiding is removed for the microbead applications, excess amounts of Boron can be incorporated into the glass to increase its photosensitivity without regard to its optical guiding properties. This has the benefit of reducing the cost of manufacturing the optical substrate when compared to manufacturing the conventional waveguide, and increasing the photosensitivity without concern for tradeoffs involving other waveguiding issues.

When optical substrate does not have to perform as a conventional waveguide, the core index of the optical substrate may be made lower than the cladding index. Under these conditions, the above equation demonstrate that the NA is imaginary, and thus the optical substrate is not considered a waveguide.

In the alternative embodiment, the optical identification element is a non-waveguide optical substrate having the Bragg grating inscribed therein. The optical identification element structure consists of a photosensitive region in the geometric center of the element surrounded by a non-photosensitive and non-absorbing region. The photosensitive region has an index of refraction less than or equal to the surrounding region, thus preventing the element from supporting any modes. The photosensitive region is also designed to produce the appropriate Bragg envelope when interrogated from the side. Bragg envelopes in the range of 1 to 10 degrees are desirable for most microbead applications. In order to achieve such an envelop with visible light, the diameter of the photosensitive region must be no larger than 30 μm, and for most applications the ideal size is approximately 12 μm. Due to this small size and the practical issues that would arise from fabricating and handing such a small optical identification element, it is convenient to include an outer region, which is neither photosensitive nor absorbing, which has an outer diameter between 50-130 μm. The optical identification element had a core diameter of 24 μm when the outer diameter was 125 μm, and a core diameter of 12 μm when it was drawn to 65 μm in diameter. The index of the core region was −0.003, thus ensuring the optical identification element would not guide a mode.

The New and Unique Optical Substrate Specification

The new and unique optical substrate may take the form of a photosensitive non-waveguide optical fiber consisting of two sections, an outer section and at least one inner section. The outer section (or cladding) is made entirely of fused silica, without any dopants; however, trace amounts of impurities commonly found in fused silica or natural fused quartz are acceptable. The inner section (or core) is made of Germanium and Boron doped fused silica. The exact constituents of Boron and Germanium are determined based on the desired refractive index profile (RIP). In one example, the photosensitive non-waveguide optical fiber may have an outer diameter of 28 μm+/−1 μm, and the inner section diameter of 8 μm+/−0.5 μm. The scope of the invention is intended to include using other dimensions as well.

The photosensitive non-waveguide optical fiber may be made by drawing a glass preform on a known fiber draw tower. Also, the photosensitive non-waveguide optical fiber may be drawn with an outer coating or buffer layer to protect the fiber during handling, e.g., a polymer based coating or other coating.

The RIP of the preform is used to calculate the following parameters of the photosensitive non-waveguide optical fiber as follows:

Fiber Core Diameter=(Fiber Outer Diameter)/Ratio, where Ratio=(Preform Outer Diameter)/(Preform Core Diameter); the Ratio stays the same for the Preform and the Fiber.

Measurements are typically taken along the length of the preform in intervals of about 1 cm; however, other intervals may be used if desired. Referring to FIG. 11, the Delta refractive index (or Delta Index) between the outer cladding and the inner core is defined as the difference: Clad index−Core index. In one example, the Delta Index may be greater than 0.001 as measured from the preform RIP (and as will also exist in the fiber). Other values for the Delta Index may be used if desired.

The elemental (or dopant) constituents (Germanium and Boron dopants) in the core may be about 20 mole % Germanium (Ge) and about 10 mole % Boron (B). Other percentages of the dopants may be used if desired. The Germanium helps increase photosensitivity and the Boron reduces the refractive index to create the depressed core shape of the fiber refractive index profile. Other values of Ge, B may be used provided the inner core region has a refractive index that is less than the outer cladding region ("depressed core"). Also, other dopant(s) now known or later developed may be used to create the depressed core substrate. Also, instead of depressing the refractive index of the core, the refractive index of the cladding may be increased to create the desired depressed core condition. In such a depressed core condition, light will not be guided along the inner core region because it does not satisfy the well known waveguide condition; thus, the substrate does not act as a waveguide. Furthermore, the substrate will not propagate light along the core that could be reflected or diffracted by a diffraction grating located in the substrate.

As discussed herein, the substrate may be photosensitive to impress the diffraction grating therein. In that case, the fiber inner region (or core) has a photosensitivity that allows for a refractive index modulation of greater than about $5\times10^{-4}$, using approximately 248 nm light, and about 0.5 Joules/cm². Other levels of photosensitivity may be used, provided it is sufficient to give the desired grating profile. The photosensitivity may be achieved by any technique now known or later developed that allows the region of the substrate where the diffraction grating is to be written to experience a change in the refractive index of the substrate material when exposed to incident radiation of a desired wavelength, e.g., Ultra Violet exposure or actinic radiation or other wavelength radiation. For example, the fiber may be loaded with Hydrogen ($H_2$) or Deuterium ($D_2$), or doped with lead, boron germanium, flame brushing, tin-germanium or other dopants, such as is described in U.S. Pat. No. 5,287,427 to Atkins, Feb. 25, 1994; or U.S. Pat. No. 5,325,659 to Atkins et al, Aug. 10, 1993; U.S. Pat. No. 5,157,747 to Atkins et al, Oct. 20, 1992; or U.S. Pat. No. 6,221,566, to Kohnke et al, Apr. 24, 2001, or U.S. Pat. No. 6,327,406 to Cullen et al, Dec. 4, 2001; or U.S. Pat. No. 6,097,512 to Ainsle et al, Aug. 1, 2000; or U.S. Pat. No. 6,075,625, to Ainslie et al, Jun. 13, 2000; U.S. Pat. No. 5,495,548 to Hill, Feb. 12, 1996; U.S. Pat. No. 6,436,857 to Brubeck et al, Aug. 20, 2002; X-C Long et al, "Large Photosensitivity in Lead Silicate Glasses", FE3-1/219 to FE3-3/221; F. Ouellette et al, Applied Physics Letters, Vol. 58(17), p 1813; G. Meltz et al, SPIE, Vol. 1516, "Int'l Workshop on Photoinduced Self-Organization in Optical Fiber", May 10-11, 1991, Quebec City, Canada, pp 1516-1518; D. McStay, SPIE, Vol. 1314, "Fibre Optics '90", pp. 223-233; and also as discussed in the book Kashyap, "Fiber Bragg Gratings", Ch. 2, pp 13-54, Academic Press 1999; each of the above U.S. patents are incorporated herein by reference.

While the substrate has been described as being used with a cylindrical fiber geometry, it should be understood that other geometries may be used, such as planar, D-shaped, or any other shape, such as is described in the aforementioned co-pending co-owned patent applications. Also, when the material is referred to as a photosensitive material it means any material whose index of refraction can be changed by exposing the material to light of a predetermined intensity at a wavelength in a predetermined range.

The foregoing and other objects, features and advantages of the present invention will become more apparent in light of the following detailed description of exemplary embodiments thereof, as illustrated in the accompanying drawing.

Figure 25:
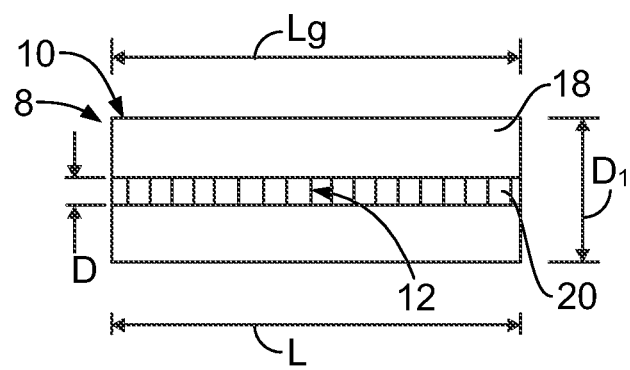
FIG. 25 is a side view of an optical identification element.

FIG. 25: the Basic Invention

Referring to FIG. 25, a diffraction grating-based optical identification element 8 (or encoded element or coded element) comprises a known optical substrate 10, having an optical diffraction grating 12 disposed (or written, impressed, embedded, imprinted, etched, grown, deposited or otherwise formed) in the volume of or on a surface of a substrate 10. The grating 12 is a periodic or aperiodic variation in the effective refractive index and/or effective optical absorption of at least a portion of the substrate 10.

The optical identification element 8 described herein is the same as that described in Copending patent application Ser. No. 10/661,234 (U.S. Patent Appl. Publ. No. 2004/0233485), filed Sep. 12, 2003, which is incorporated herein by reference in its entirety.

In particular, the substrate 10 has an inner region 20 where the grating 12 is located. The inner region 20 may be photosensitive to allow the writing or impressing of the grating 12. The substrate 10 has an outer region 18, which does not have the grating 12 therein.

The grating 12 is a combination of one or more individual spatial periodic sinusoidal variations (or components) in the refractive index that are collocated at substantially the same location on the substrate 10 along the length of the grating region 20, each having a spatial period (or pitch) λ. The resultant combination of these individual pitches is the grating 12, comprising spatial periods ($\lambda_1$-$\lambda_n$) each representing a bit in the code. Thus, the grating 12 represents a unique optically readable code, made up of bits, where a bit corresponds to a unique pitch λ within the grating 12. Accordingly, for a digital binary (0-1) code, the code is determined by which spatial periods ($\lambda_1$-$\lambda_n$) exist (or do not exist) in a given composite grating 12. The code or bits may also be determined by additional parameters (or additional degrees of multiplexing), and other numerical bases for the code may be used, as discussed herein and/or in the aforementioned patent application.

The grating 12 may also be referred to herein as a composite or collocated grating. Also, the grating 12 may be referred to as a "hologram", as the grating 12 transforms, translates, or filters an input optical signal to a predetermined desired optical output pattern or signal.

The substrate 10 has an outer diameter D1 and comprises silica glass ($SiO_2$) having the appropriate chemical composition to allow the grating 12 to be disposed therein or thereon. Other materials for the optical substrate 10 may be used if desired, including materials now known or later developed in the future. For example, the substrate 10 may be made of any glass, e.g., silica, phosphate glass, borosilicate glass, or other glasses, or made of glass and plastic, or solely plastic. For high temperature or harsh chemical applications, the optical substrate 10 made of a glass material is desirable. If a flexible substrate is needed, plastic, rubber or polymer-based substrate may be used. The optical substrate 10 may be any material capable of having the grating 12 disposed in the grating region 20 and that allows light to pass through it to allow the code to be optically read.

The optical substrate 10 with the grating 12 has a length L and an outer diameter D1, and the inner region 20 diameter D. The length L can range from very small "microbeads" (or microelements, micro-particles, or encoded particles), about 1-1,000 microns or smaller, to larger "macrobeads" or "macroelements" for larger applications (about 1.0-1,000 mm or greater). In addition, the outer dimension D1 can range from small (less than 1,000 microns) to large (1.0-1,000 mm and greater). Other dimensions and lengths for the substrate 10 and the grating 12 may be used.

The grating 12 may have a length Lg of about the length L of the substrate 10. Alternatively, the length Lg of the grating 12 may be shorter than the total length L of the substrate 10.

The outer region 18 is made of pure silica ($SiO_2$) and has a refractive index n2 of about 1.458 (at a wavelength of about 1553 nm), and the inner grating region 20 of the substrate 10 has dopants, such as germanium and/or boron, to provide a refractive index n1 of about 1.453, which is less than that of outer region 18 by about 0.005. Other indices of refraction n1,n2 for the grating region 20 and the outer region 18, respectively, may be used, if desired, provided the grating 12 can be impressed in the desired grating region 20. For example, the grating region 20 may have an index of refraction that is larger than that of the outer region 18 or grating region 20 may have the same index of refraction as the outer region 18 if desired.

Figure 26:
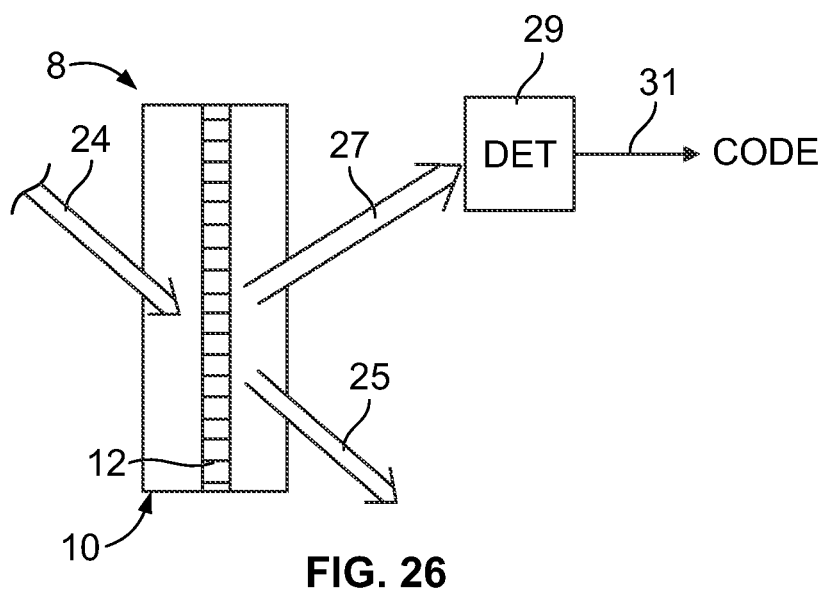
FIG. 26 is a top level optical schematic for reading a code in an optical identification element.

Referring to FIG. 26, an incident light 24 of a wavelength λ, e.g., 532 nm from a known frequency doubled Nd:YAG laser or 632 nm from a known Helium-Neon laser, is incident on the grating 12 in the substrate 10. Any other input wavelength λ can be used if desired provided λ is within the optical transmission range of the substrate (discussed more herein and/or in the aforementioned patent application). A portion of the input light 24 passes straight through the grating 12, as indicated by a line 25. The remainder of the input light 24 is reflected by the grating 12, as indicated by a line 27 and provided to a detector 29. The output light 27 may be a plurality of beams, each having the same wavelength λ as the input wavelength λ and each having a different output angle indicative of the pitches ($\lambda_1$-$\lambda_n$) existing in the grating 12. Alternatively, the input light 24 may be a plurality of wavelengths and the output light 27 may have a plurality of wavelengths indicative of the pitches ($\lambda_1$-$\lambda_n$) existing in the grating 12. Alternatively, the output light may be a combination of wavelengths and output angles. The above techniques are discussed in more detail herein and/or in the aforementioned patent application.

The detector 29 has the necessary optics, electronics, software and/or firmware to perform the functions described herein. In particular, the detector reads the optical signal 27 diffracted or reflected from the grating 12 and determines the code based on the pitches present or the optical pattern, as discussed more herein or in the aforementioned patent application. An output signal indicative of the code is provided on a line 31.

The Grating Writing Process

The diffraction grating(s) 12 may be written or shot, for example, in the manner shown and described in detail in the technique shown and described in the aforementioned patent application Ser. No. 10/661,234 (U.S. Patent Appl. Publ. No. 2004/0233485), filed Sep. 12, 2003, which is incorporated herein by reference in its entirety. The grating 12 may be impressed in the optical fiber or substrate by any technique for writing, impressed, embedded, imprinted, or otherwise forming a diffraction grating in the volume of or on a surface of a substrate 10. Examples of some known techniques are described in U.S. Pat. Nos. 4,725,110 and 4,807,950, entitled "Method for Impressing Gratings Within Fiber Optics", to Glenn et al; and U.S. Pat. No. 5,388,173, entitled "Method and Apparatus for Forming Aperiodic Gratings in Optical Fibers", to Glenn, respectively, and U.S. Pat. No. 5,367,588, entitled "Method of Fabricating Bragg Gratings Using a Silica Glass Phase Grating Mask and Mask Used by Same", to Hill, and U.S. Pat. No. 3,916,182, entitled "Periodic Dielectric Waveguide Filter", Dabby et al, and U.S. Pat. No. 3,891,302, entitled "Method of Filtering Modes in Optical Waveguides", to Dabby et al, which are all incorporated herein by reference to the extent necessary to understand the present invention.

Alternatively, instead of the grating 12 being impressed within the fiber material, the grating 12 may be partially or totally created by etching or otherwise altering the outer surface geometry of the substrate to create a corrugated or varying surface geometry of the substrate, such as is described in U.S. Pat. No. 3,891,302, entitled "Method of Filtering Modes in Optical Waveguides", to Dabby et al, which is incorporated herein by reference to the extent necessary to understand the present invention, provided the resultant optical refractive profile for the desired code is created.

Further, alternatively, the grating 12 may be made by depositing dielectric layers onto the substrate, similar to the way a known thin film filter is created, so as to create the desired resultant optical refractive profile for the desired code.

FIG. 27

Figure 27:
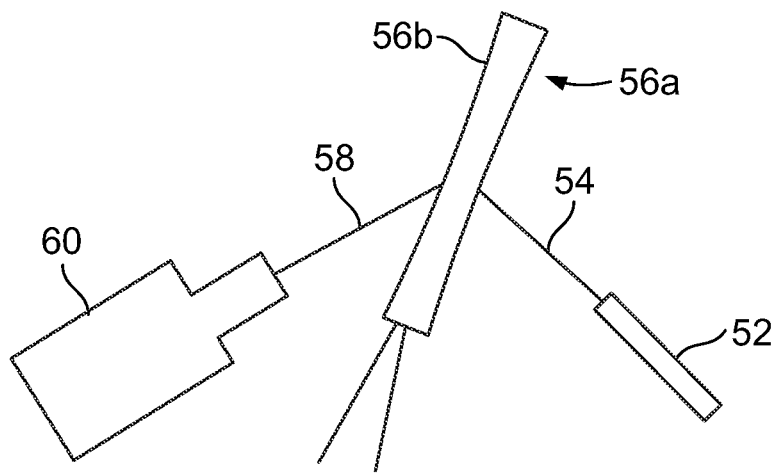
FIG. 27 is a schematic of Bragg grating envelop measurement.

The optical identification element was exposed to 7 collocated gratings and interrogated from the side in the manner described in U.S. Patent Appl. Publ. No. 2004/0233485 incorporated herein by reference. The resulting diffracted beams were imaged onto a CCD camera like that shown in FIG. 27 and the images were captured using a frame grabber card in a personal computer (PC). The Bragg envelop for the two optical identification elements were also measured by capturing the images of the diffracted beams for a range of rotation angles. It was found that under normal exposure conditions, the excess Boron in the core provided enhanced photosensitivity over the standard "photosensitive" telecom fiber.

Figure 28:
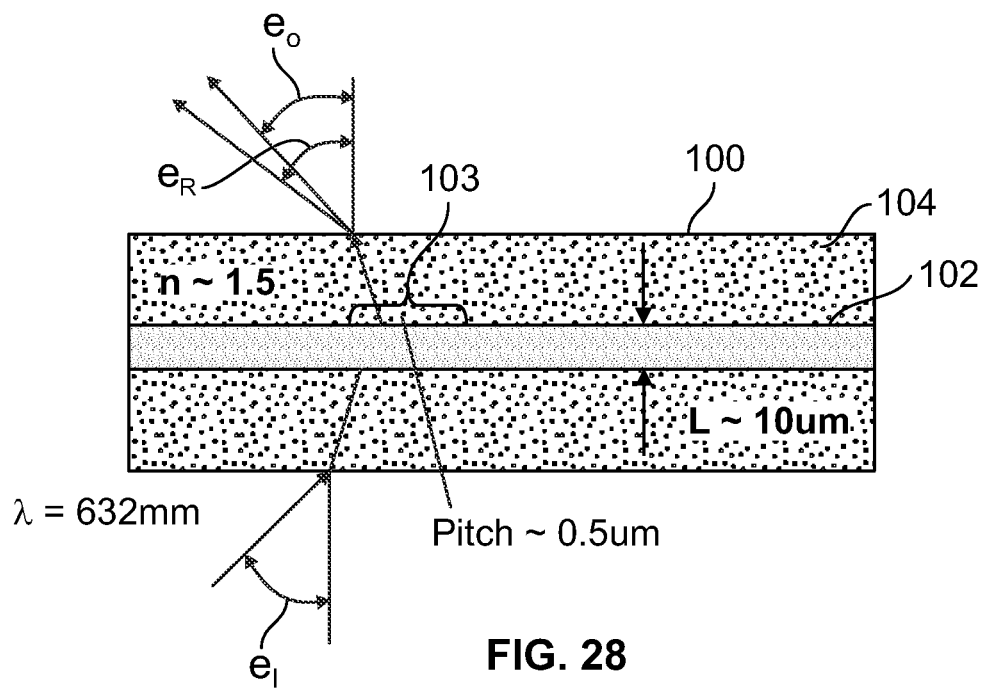
FIGS. 28 and 29 are schematics of a fiber geometry.
Figure 29:
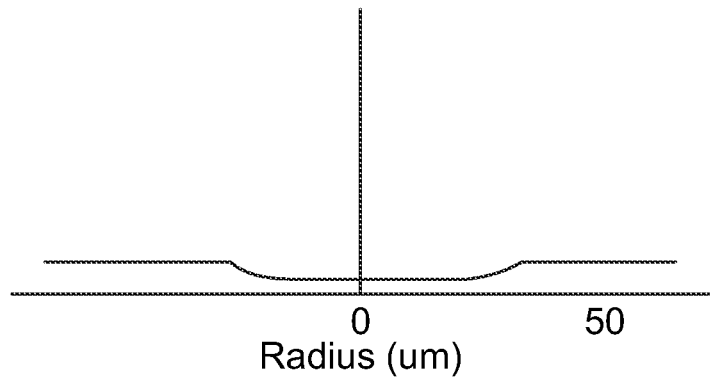
Figure 35:
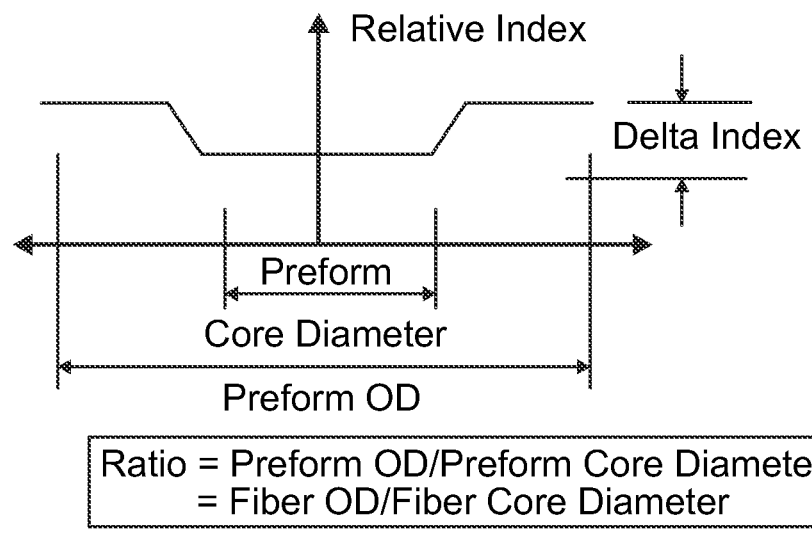
FIG. 35 shows a refractive index profile for a preform.
Figure 30:
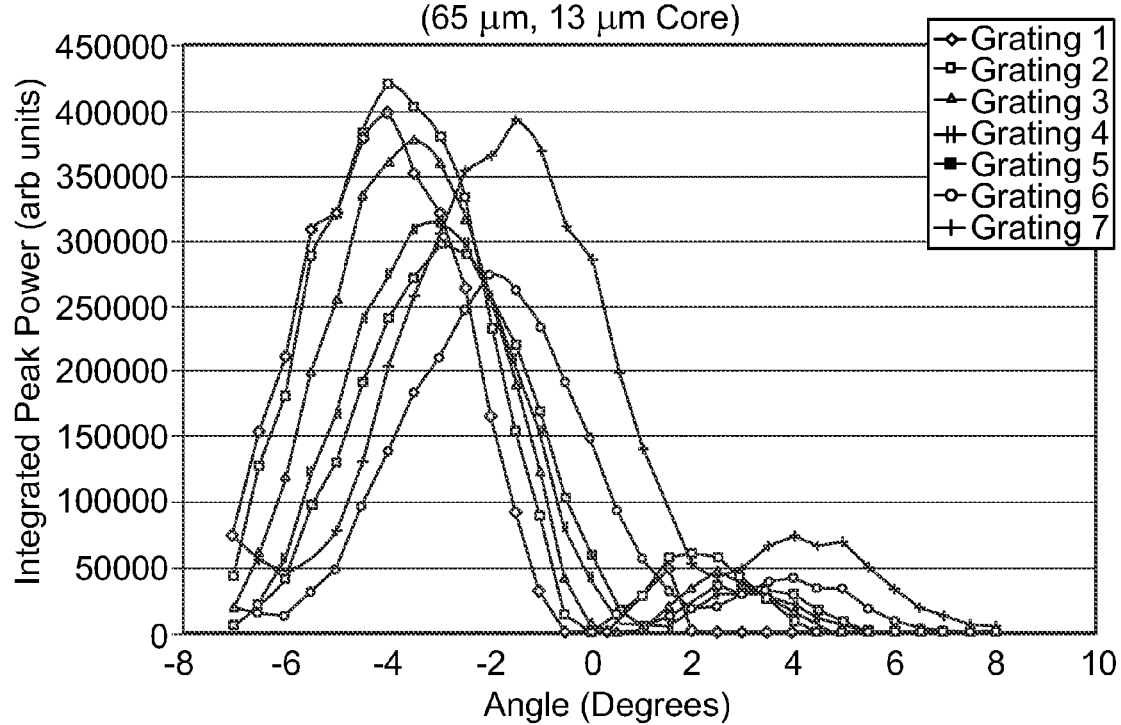
FIG. 30 shows a graph of a Bragg envelop measurement for depressed core fiber with 7 collocated gratings (65 μm, 13 μm core), having the integrated peak power (arbitrary units) plotted in relation to the angle (degrees) of incidence.
Figure 31:
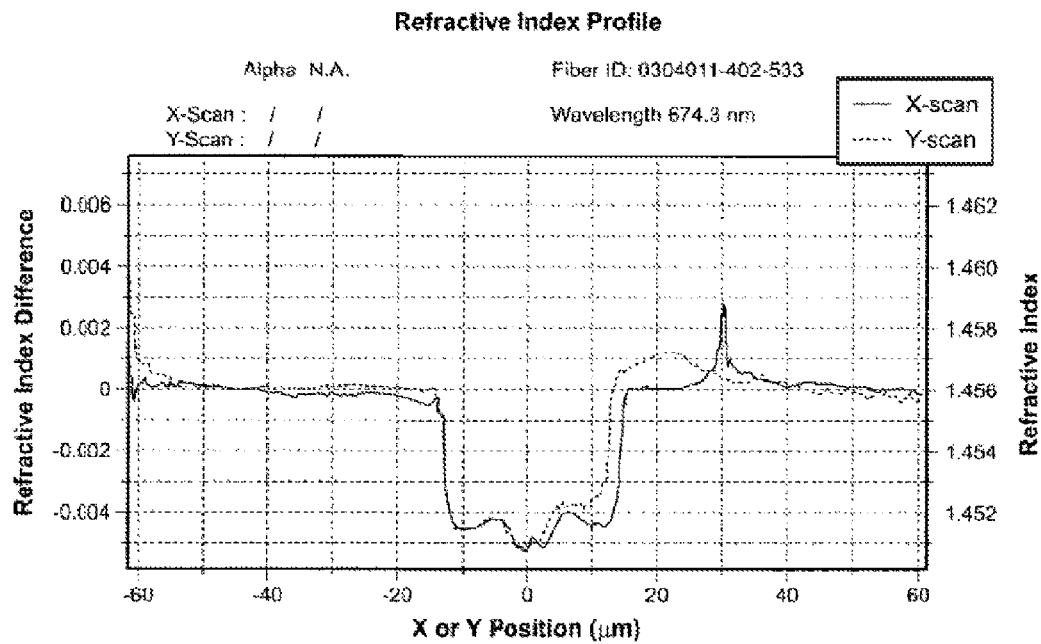
FIG. 31 shows a refractive index profile for a substrate having an outer diameter (OD) of 125 μm and a core diameter of 253 μm.
Figure 32:
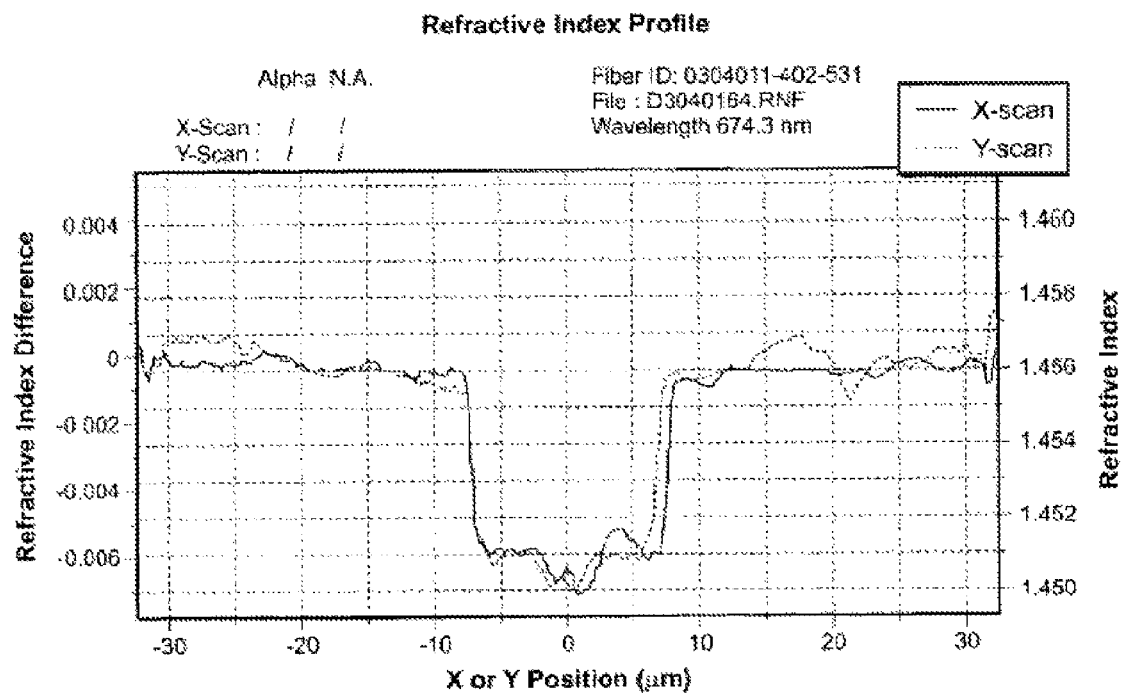
FIG. 32 shows a refractive index profile for a substrate having an outer diameter (OD) of 65 μm and a core diameter of 14 μm.
Figure 33:
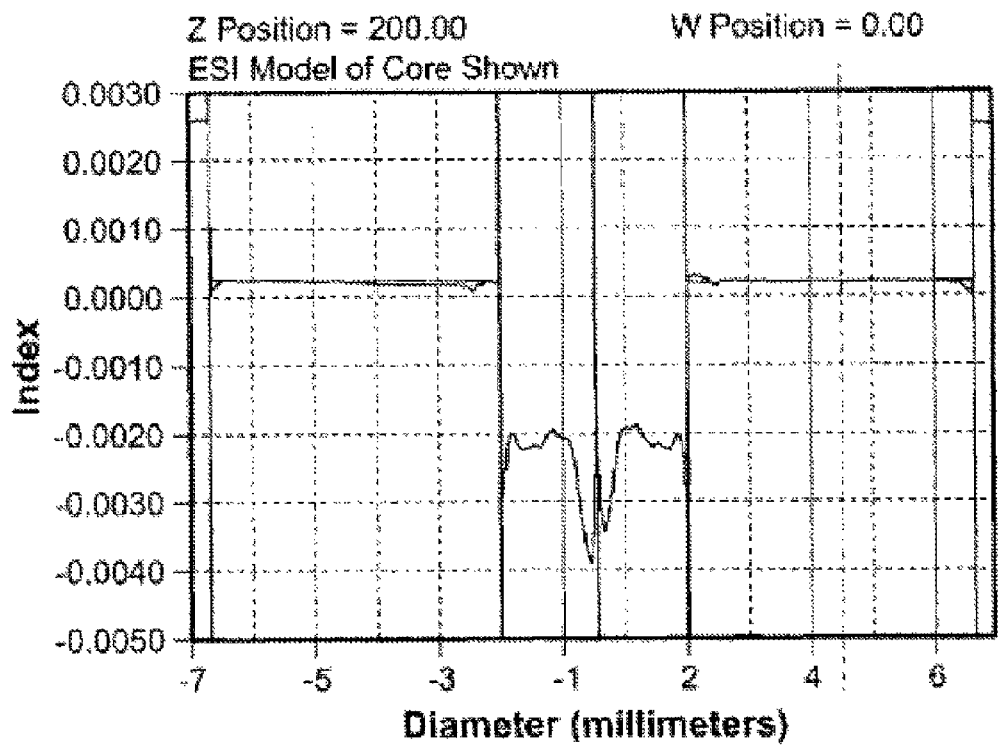
FIG. 33 shows a refractive index profile for a preform having an outer diameter of 13 mm and a core having a diameter of 3 mm.
Figure 34:
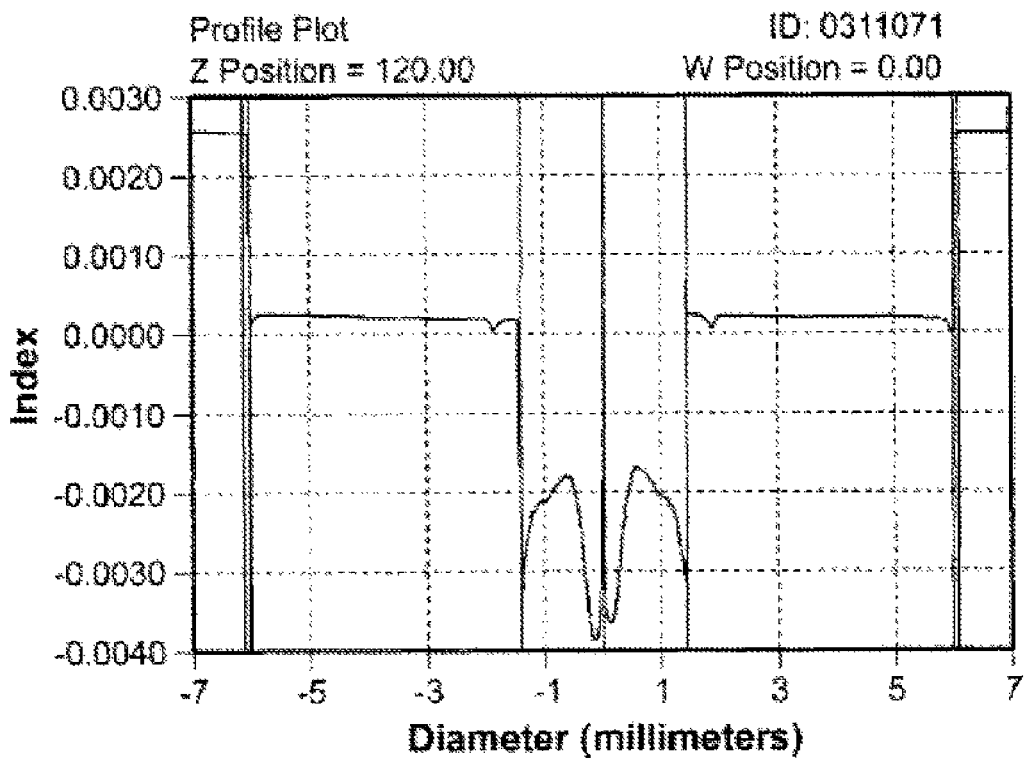
FIG. 34 shows a refractive index profile for a preform having an outer diameter of 12 mm and a core having a diameter of 2.4 mm.

FIG. 28 shows a schematic of the fiber geometry of an optical fiber or substrate 100 having a core 102 with a grating 103 and having a cladding 104. As shown, the core 102 has a length L of about 10 µm and the grating has a pitch of about 0.5 µm. In response to an optical signal having a wavelength λ=632 nanometers (nm) received at an angle $\theta_i$, the grating provides a reflected optical fiber at an angle $\theta_O$ with respect to the normal consisting of a plurality of uniquely distinguishable signals covering an angle range of $\theta_R$. The index of refraction of the cladding and core respectively are 1.458 and 1.455 (i.e. difference of 0.003).

Subject Matter from U.S. Provisional App. No. 60/546,435:

FIG. 36

Figure 36:
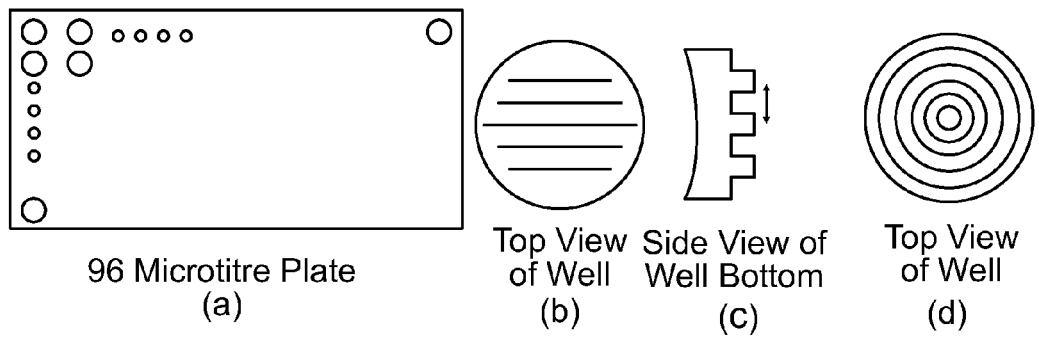
FIGS. 36(a), (b), (c) and (d) show an embodiment of the present invention that uses microtitre plates whose bottoms consist of flat or contoured groove plates.
Figure 37:
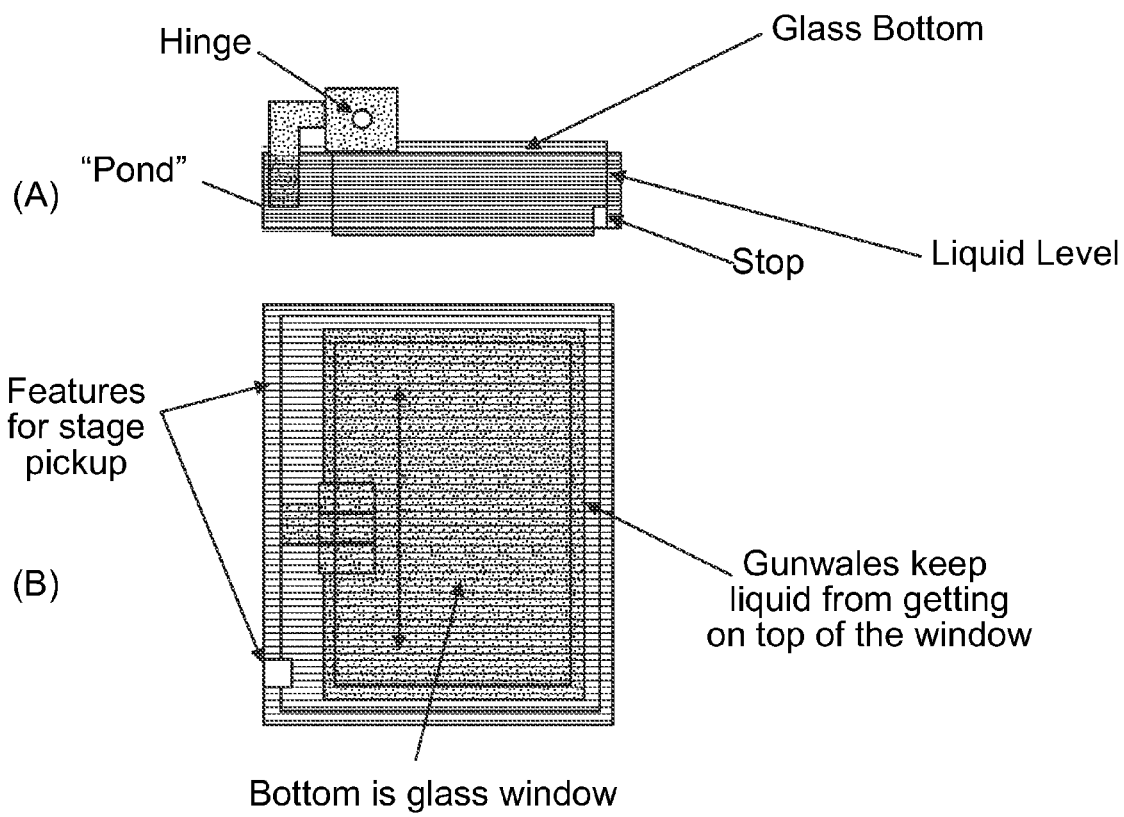
FIGS. 37-41 show a cell or tray design for loading and unloading beads during the bead alignment and interrogation process.
Figure 38:
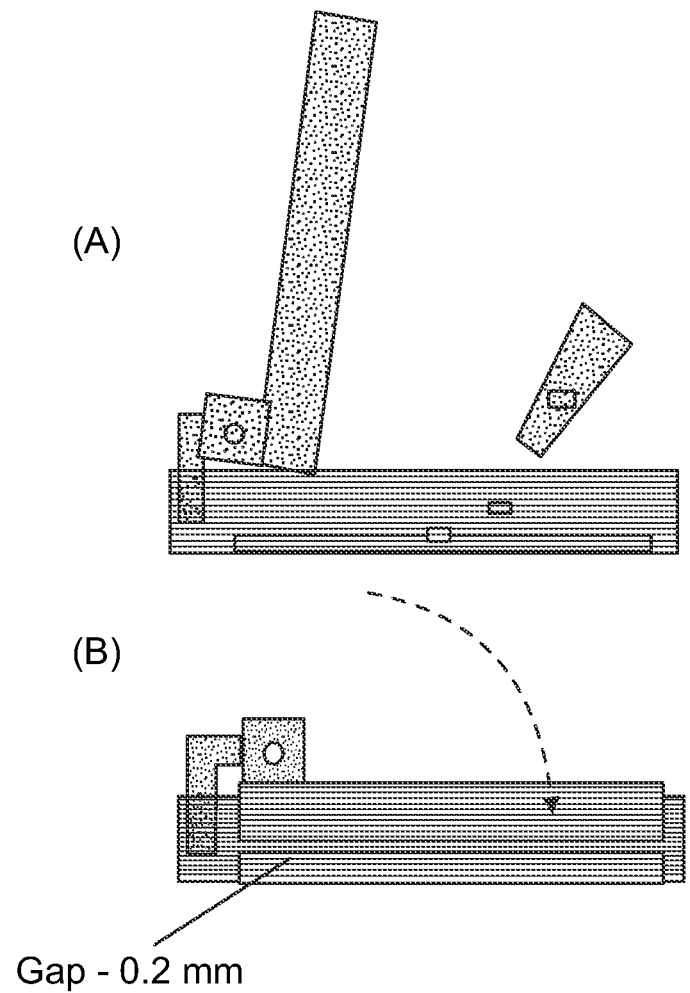
Figure 39:
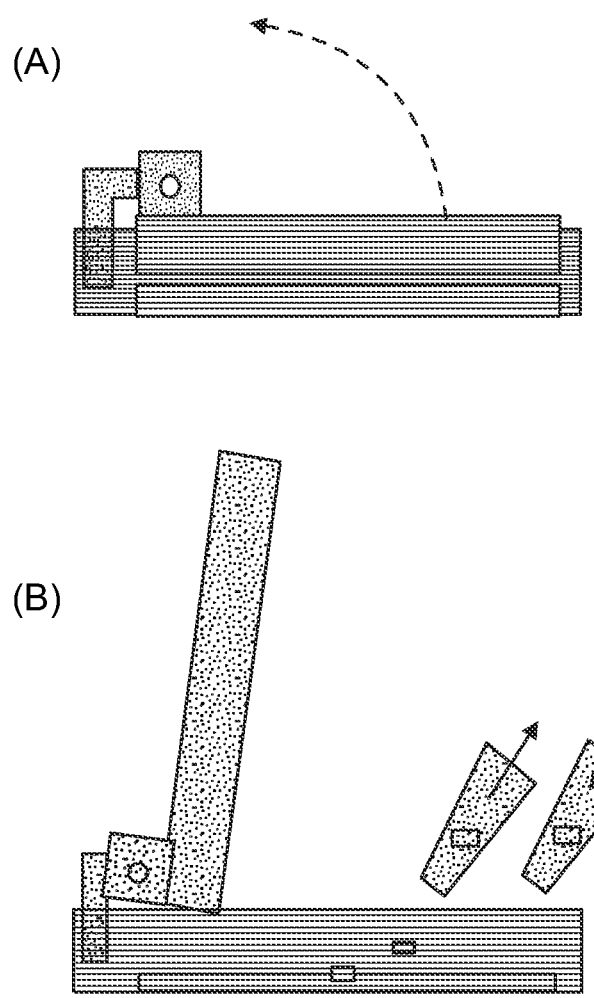

FIGS. 36(a), (b),(c) and (d) show an embodiment of the present invention that uses microtitre plates whose bottoms consist of flat or contoured groove plates. In this embodiment, beads are agitated to align themselves in the groove plates, and then codes and labels are read directly from the bottom of the microtitre plates with standard or custom fluorescence scanners. This embodiment has the advantage of removing the bead transfer step, which in turn increases sample throughput and reduces the requisite investment in fluidic handling automation equipment. In FIG. 36(b), the microtitre plate has straight grooves in the bottom that are about as wide as they are deep (1:1 aspect ratio) and can have a pitch of 1 to 200 microns. In comparison, in FIG. 36(d), the microtitre plate has circular grooves arranged concentrically. In addition, the grooves may be 100% to 200% of the bead diameter, and preferably about 120%. For example, if the bead diameter is 28 microns, then the groove diameter should be about 32 microns. Moreover, it is important to note that the scope of the invention is not intended to be limited only to straight or concentric circular grooves, since embodiments are envisioned using grooves having other geometries, including diamond shaped, swirvy, etc.

FIGS. 37-41

FIGS. 37-41 show a cell or tray design for loading and unloading beads during the bead alignment and interrogation process. The design makes bead loading/unloading more convenient. The goals are to be able to pipette the beads into the cell or tray; easily vacuum or wash the beads from the cell or tray; easily disassemble and clean the cell or tray; and provide an open cell architecture that lets bubbles out but keeps beads wet for hours.

FIGS. 37(a) and (b)

FIGS. 37(a) and (b) show a side and top view of a cell or tray having four sides surrounding a glass plate or bottom with grooves, and having a top hingeably coupled to the cell or tray.

FIGS. 38(a) and (b): Bead Loading

FIGS. 38(a) and (b) show bead loading, with FIG. 38(a) showing the top open and a pipette for providing beads into the tray or cell so as to fill it like a so-called "pond". The cell or tray is stimulated, for example, using a magnetic stir bar, to aid the alignment of the beads in the grooves on the bottom plate. In FIG. 38(b), the top is closed when the beads are aligned.

FIGS. 39(a) and (b): Bead Unloading

FIGS. 39(a) and (b) show bead unloading, with FIG. 39(a) showing the top opening, and FIG. 39(b) showing a vacuum sucking the beads out. Alternatively, the cell or tray can be turned sideways and the beads flushed out with a jet of liquid.

FIGS. 40-41

Figure 40:
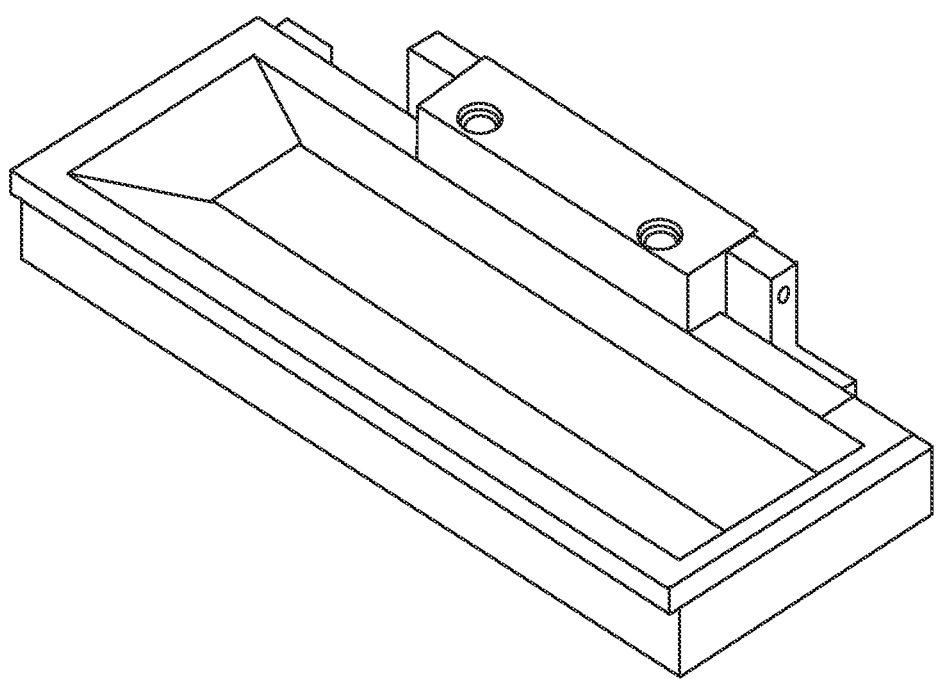
Figure 41:
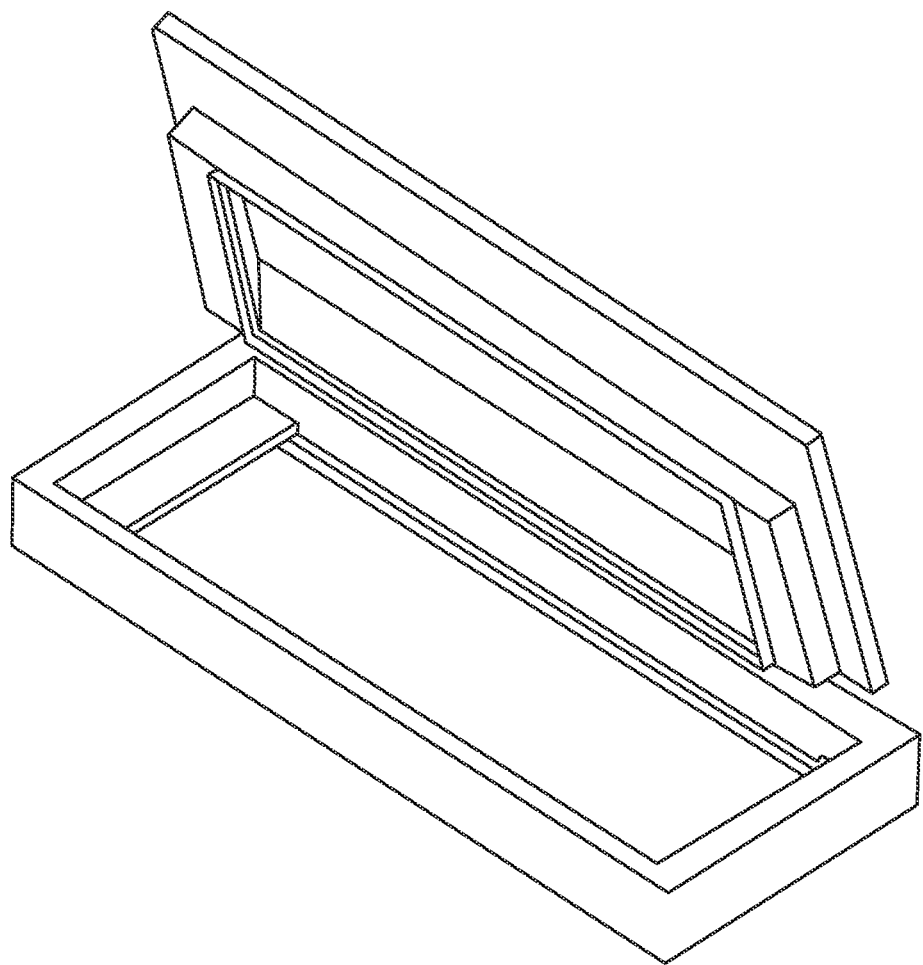

FIG. 40 shows an elevated perspective of the cell or tray with the cover down, while FIG. 41 shows an elevated perspective of the cell or tray with the cover up.

Figure 42:
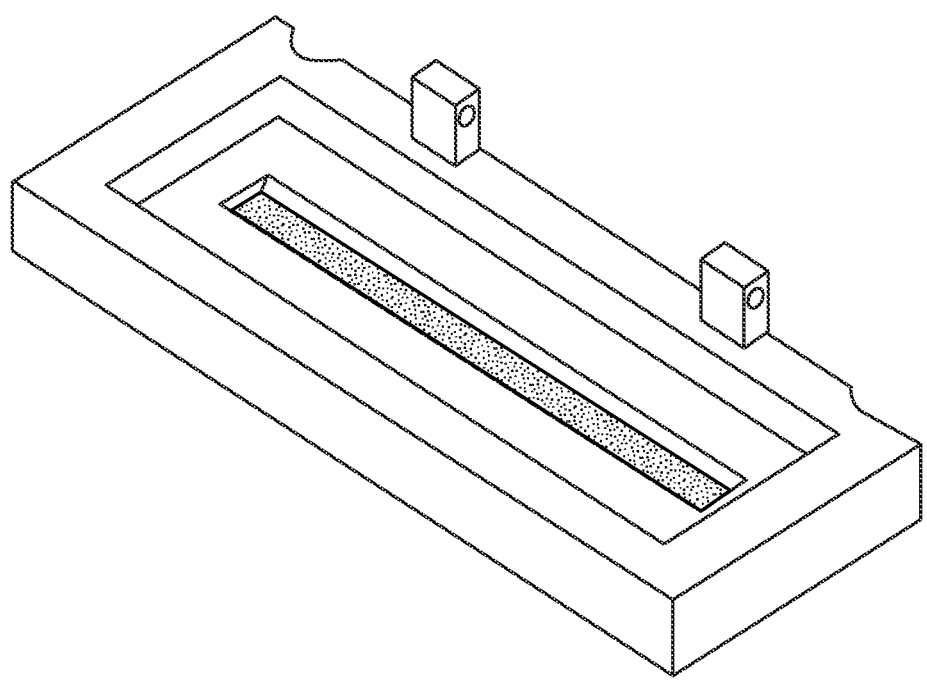
FIG. 42 shows an alternative embodiment in which the bead alignment device has a narrow window.

FIG. 42: Bead Alignment Device Having Narrow Groove Plate

FIG. 42 shows an alternative embodiment in which the bead alignment device having a narrow window. As shown, the grooves are in a section of the bottom plate, not across entire bottom. In response to some stimulation, the beads are coralled in narrow window and fall into alignment.

Figure 43:
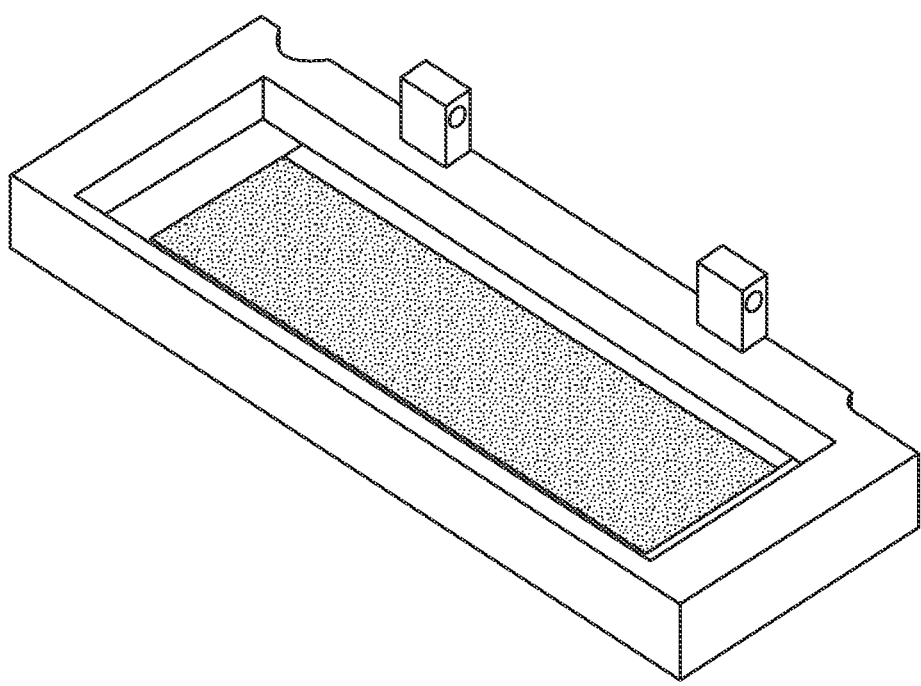
FIGS. 43-45 illustrate bead alignment devices having wide windows.
Figure 44:
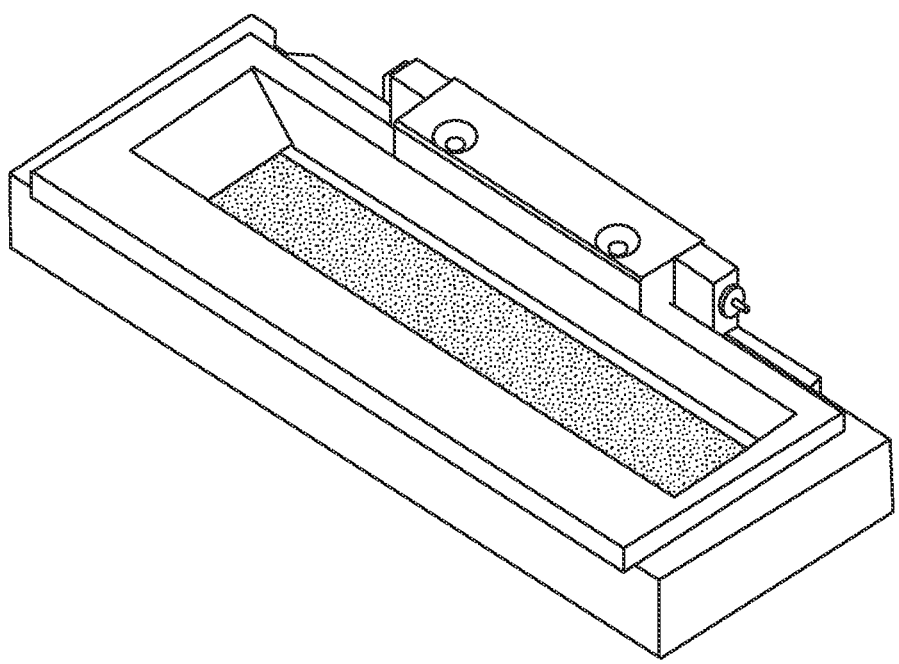
Figure 45:
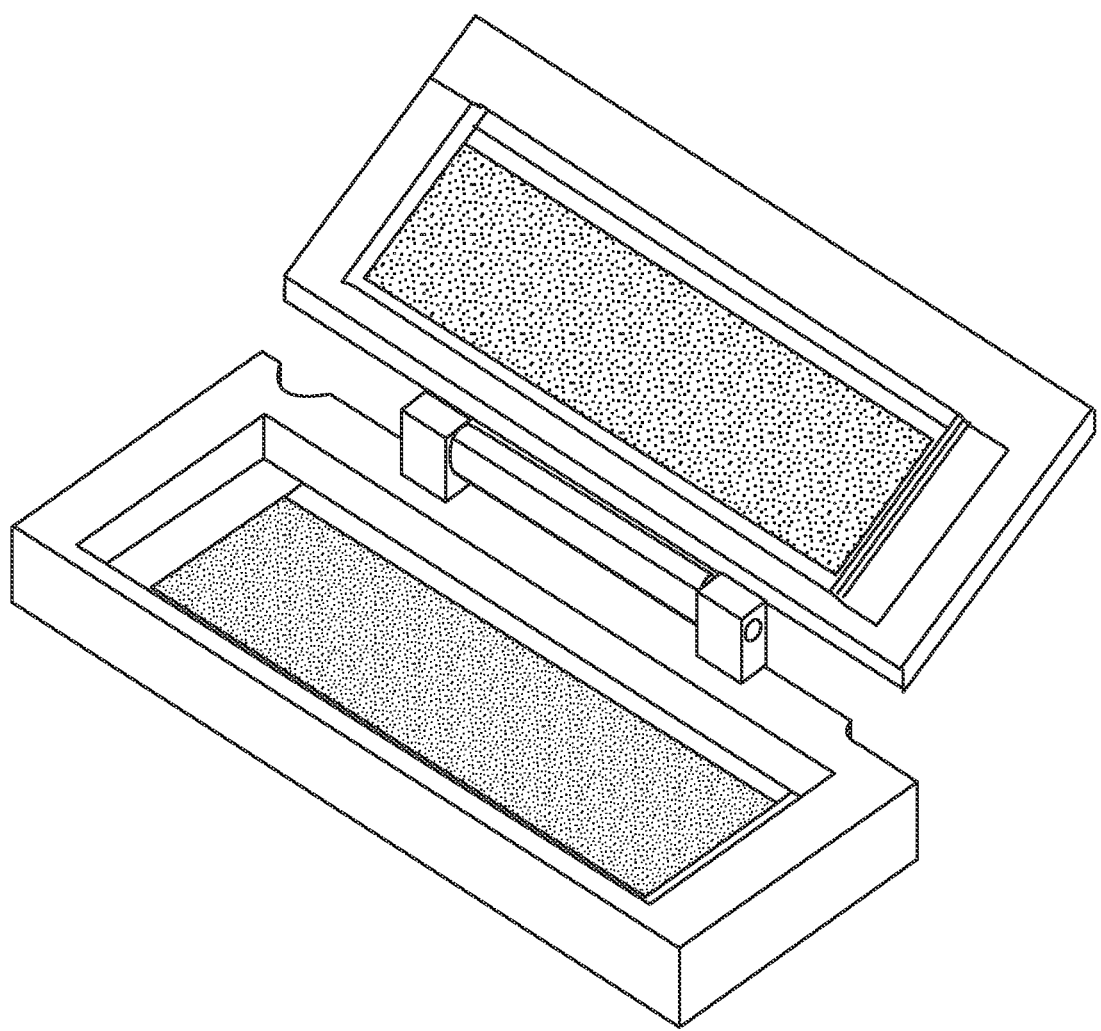

FIGS. 43-45: Bead Alignment Device Having Wide Window

In FIG. 43, the grooves extend substantially along the entire base. When the solution having the microbeads is provided to the bead alignment device, the beads align themselves in the grooves. Consistent with that discussed above, typically the bead alignment device is stimulated to encourage bead movement into and alignment in the grooves.

Figure 46:
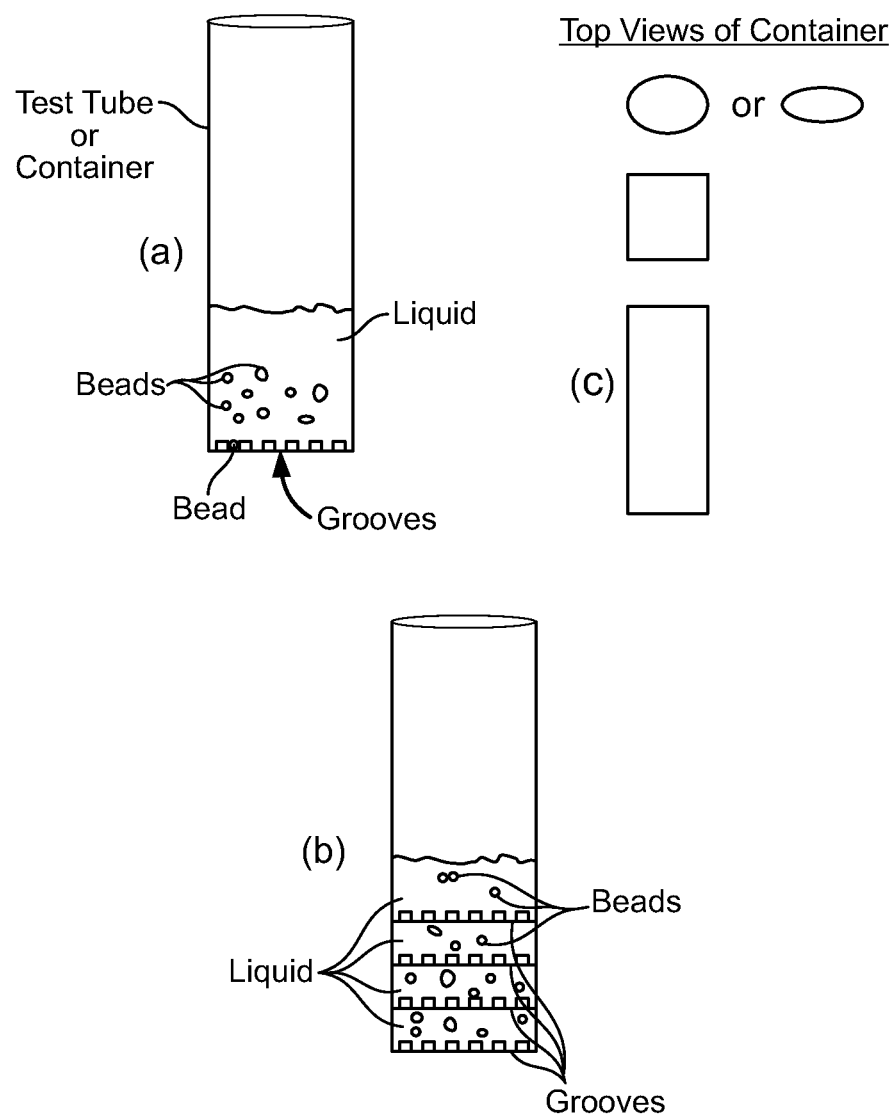
FIGS. 46(a), (b) and (c) show an alternative embodiment of the alignment cell or tray in the form of a test tube or other container.

FIGS. 46(a), (b), (c)

FIGS. 46(a), (b) and (c) show an alternative embodiment of the alignment cell or tray in the form of a test tube or other container. In FIG. 46(a), the grooves are arranged in the bottom of the test tube for aligning the beads contained in the liquid. In FIG. 46(b), the container is shown having multiple levels of grooved platforms, which may be perforated to allow liquid and/or the beads to flow between levels. FIG. 46(c) shows top views of various containers, which may have different geometric shapes, including circular, oval, square, rectangular. The scope of the invention is not intended to be limited to any particular container shape.

Subject Matter from U.S. Provisional App. No. 60/547,013:

FIG. 47

Figure 47:
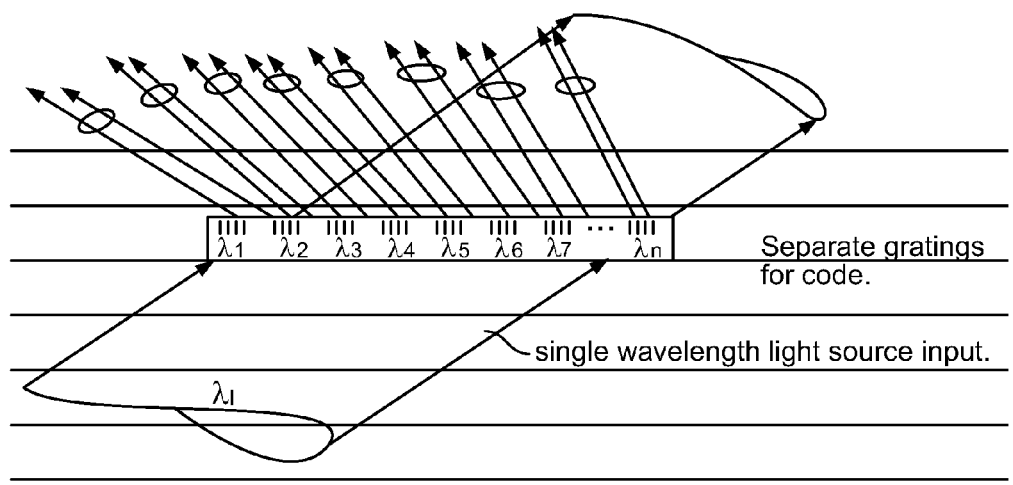
FIG. 47 shows an optical signal from a single wavelength light source input arranged in relation to a microbead having multiple base gratings with wavelengths $\lambda_1$-$\lambda_n$.

FIG. 47 shows an optical signal from a single wavelength light source input arranged in relation to a microbead having multiple base gratings with wavelengths $\lambda_1$-$\lambda_n$. The output light beams have angles that are indicative of the code, similar to that described herein or in copending U.S. patent application Ser. No. 10/661,234 (U.S. Patent Appl. Publ. No. 2004/0233485), filed Sep. 12, 2003, incorporated herein by reference. The base grating may be a single wavelength grating or a plurality of overlapped gratings, such as is described herein or in copending U.S. patent application Ser. No. 10/661,234 (U.S. Patent Appl. Publ. No. 2004/0233485), filed Sep. 12, 2003, incorporated herein by reference.

FIG. 48

Figure 48:
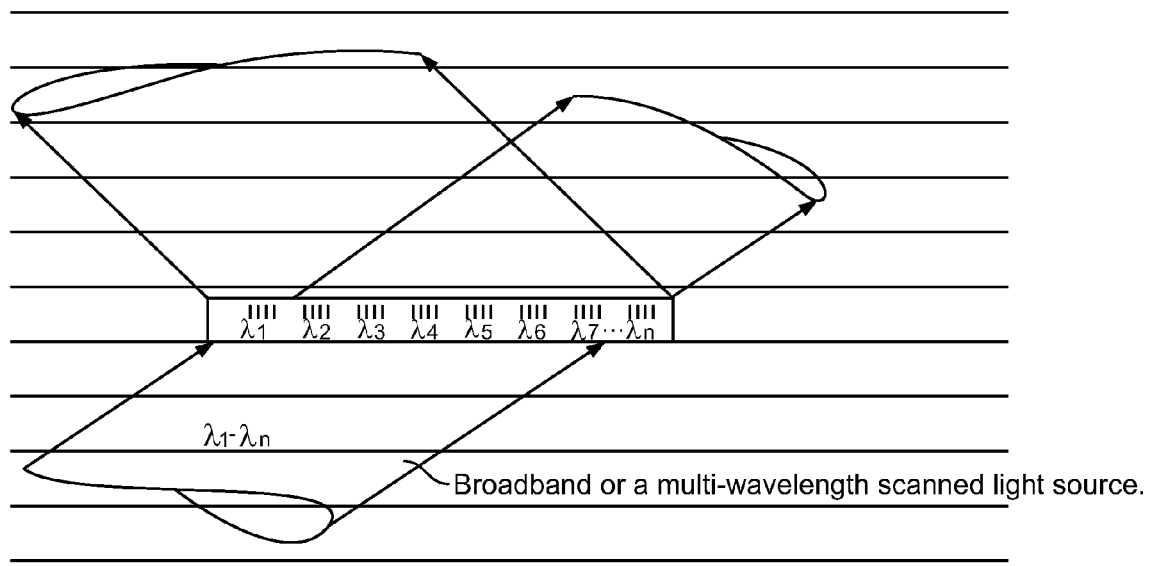
FIG. 48 shows an optical signal from a broadband or a multiwavelength scanned light source arranged in relation to a microbead having multiple base gratings with wavelengths $\lambda_1$-$\lambda_n$.

FIG. 48 shows an optical signal from a broadband or a multiwavelength scanned light source arranged in relation to a microbead having multiple base gratings with wavelengths $\lambda_1$-$\lambda_n$. The output beam has wavelengths and/or angles indicative of the code—similar to that described herein or in copending U.S. patent application Ser. No. 10/661,234 (U.S. Patent Appl. Publ. No. 2004/0233485), filed Sep. 12, 2003, incorporated herein by reference. The base grating may be a single wavelength grating or a plurality of overlapped gratings, such as is described herein or in copending U.S. patent application Ser. No. 10/661,234 (U.S. Patent Appl. Publ. No. 2004/0233485), filed Sep. 12, 2003, incorporated herein by reference.

FIG. 49

Figure 49:
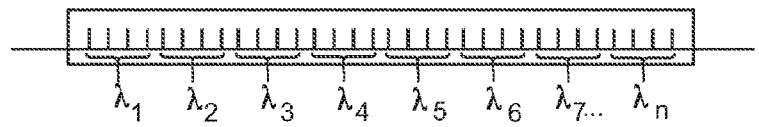
FIG. 49 shows a microbead having multiple wavelengths $\lambda_1$-$\lambda_n$.

FIG. 49 shows a microbead having multiple wavelengths $\lambda_1$-$\lambda_n$. In FIGS. 47-49, the code is made up of individual grating regions that are not overlapped. They can be spatially separated as shown in FIGS. 47-48 or be substantially one spatially continuous grating, as shown below in relation to FIG. 49. The base grating may be a single wavelength grating or a plurality of overlapped gratings, such as is described herein or in copending U.S. patent application Ser. No. 10/661,234 (U.S. Patent Appl. Publ. No. 2004/0233485), filed Sep. 12, 2003, incorporated herein by reference.

FIG. 50

Figure 50:
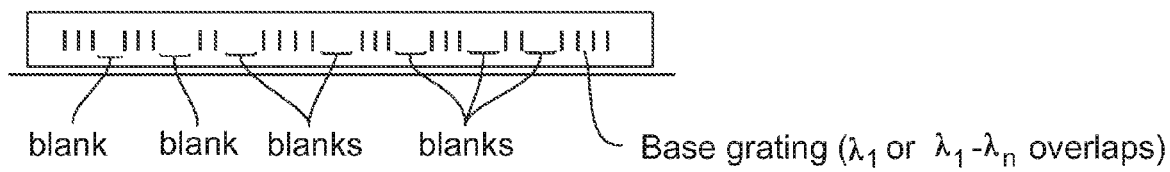
FIG. 50 shows a microbead having multiple wavelengths $\lambda_1$-$\lambda_n$ that are spatially separated by blanks.

FIG. 50 shows a microbead having multiple wavelengths $\lambda_1$-$\lambda_n$ that are spatially separated by blanks. During manufacture, blanks may be created by selective erasing of the base grating, such as by a $Co_2$ Laser, as in U.S. Pat. No. 6,681,067.

Alternatively, the segmented grating may be made by a mask having blank portions.

Alternatively, the code may be based on blanks or constant index regions spatially along a base grating. The base grating may be a single wavelength grating ($\lambda_1$) or a plurality of overlapped gratings $\lambda_1$-$\lambda_n$ overlaps. This may also be a segmented grating.

FIG. 51

Figure 51:
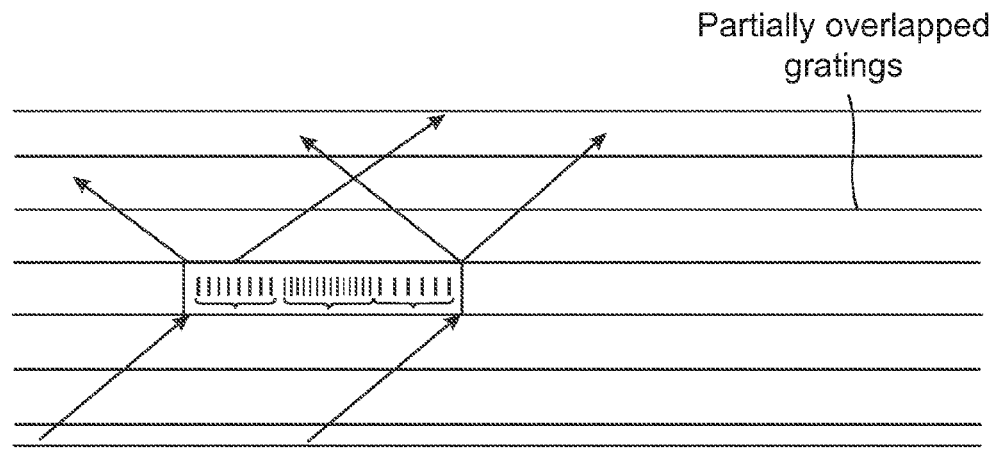
FIG. 51 shows a microbead having partially overlapped gratings.

FIG. 51 shows a microbead having partially overlapped gratings.

FIG. 52

Figure 52:
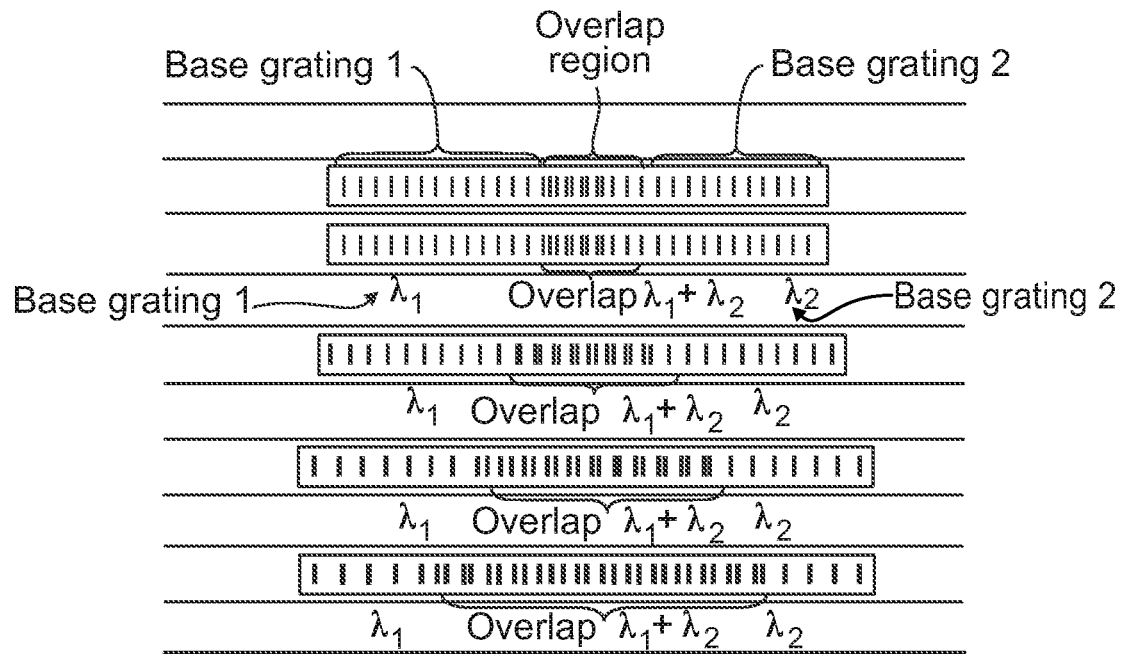
FIG. 52 shows a microbead having multiple base gratings, wherein the (length or) amount of overlap of 2 base gratings determines the code.

FIG. 52 shows a microbead having multiple base gratings, wherein the (length or) amount of overlap of 2 base gratings determines the code. In FIG. 52, the overlap region occurs at the ends of the 2 Base grating(s) ($\lambda_1$-$\lambda_2$). The base grating may be a single wavelength grating or a plurality of overlapped gratings, such as is described herein or in copending U.S. patent application Ser. No. 10/661,234 (U.S. Patent Appl. Publ. No. 2004/0233485), filed Sep. 12, 2003, incorporated herein by reference.

FIG. 53

Figure 53:
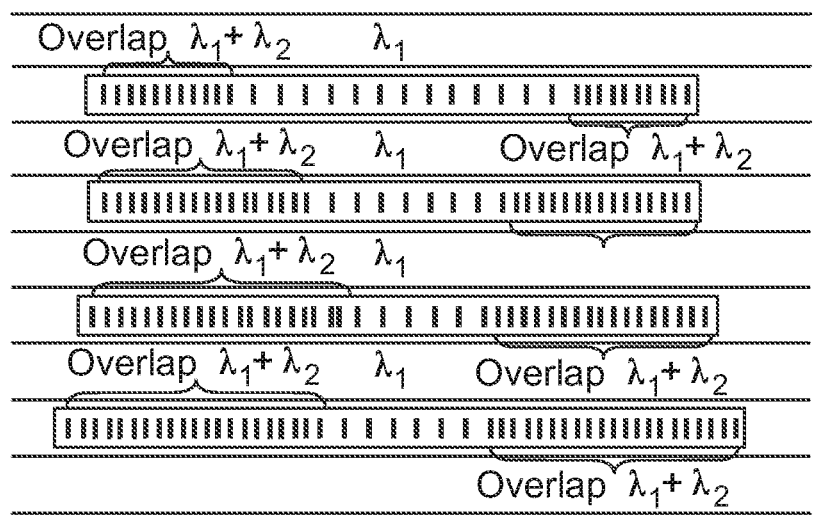
FIG. 53 shows a microbead having multiple base gratings, wherein the overlap occurs at one end or at both ends of a single Base grating(s) ($\lambda_1$).

FIG. 53 shows a microbead having multiple base gratings, wherein the overlap occurs at one end or at both ends of a single Base grating(s) ($\lambda_1$). The base grating may be a single wavelength grating or a plurality of overlapped gratings, such as is described herein or in copending U.S. patent application Ser. No. 10/661,234 (U.S. Patent Appl. Publ. No. 2004/0233485), filed Sep. 12, 2003, incorporated herein by reference.

The present invention may be used with all of the applications/uses described in the above-referenced copending patent applications. It may also be used in any of the various geometries and alternative embodiments described in the above-referenced copending patent applications, which are all incorporated herein by reference.

Unless otherwise specifically stated herein, the term "microbead" is used herein as a label and does not restrict any embodiment or application of the present invention to certain dimensions, materials and/or geometries.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

What is claimed is:

1. An optical system comprising:
microbeads that are structurally distinct and capable of moving independently with respect to one another, the microbeads being encoded and configured to provide output light signals onto a Fourier plane when illuminated by an incident light;
an input light source configured to illuminate the structurally distinct microbeads thereby providing the output light signals, the output light signals configured to be projected onto the Fourier plane in a readable manner;
a reading device positioned to detect the output light signals from the Fourier plane;
a processor configured to perform Fourier plane analysis of the optical light signals to determine corresponding codes of the microbeads; and
a support substrate configured to receive a plurality of the microbeads that are randomly distributed along the support substrate.

2. An optical system of claim 1, wherein the support substrate is configured to orient the microbeads in a predetermined manner for when the microbeads are illuminated.

3. An optical system of claim 1, wherein the system is configured to orient the microbeads in a predetermined manner for when the microbeads are illuminated.

4. An optical system of claim 1, wherein the output light signals are projected on the Fourier plane by scattering incident light off or through the microbeads.

5. An optical system of claim 1, wherein the reading device includes a charge coupled device (CCD).

6. An optical system of claim 1, further comprising a transform lens that is configured to be arranged between the microbeads and the Fourier plane at a distance of about one focal length f from the Fourier plane and at a distance of about one focal length f from the microbeads.

7. An optical system of claim 1, wherein the processor determines the codes based upon detected Fourier components from the output light signals.

8. An optical system of claim 7, wherein information is contained in both a power amplitude and spatial frequency of the Fourier components, the processor analyzing the power amplitude and the spatial frequency of the Fourier components.

9. An optical system of claim 1, wherein the corresponding codes are determined by looking at a presence or absence of predetermined Fourier spatial frequencies.

10. An optical system of claim 1, wherein the output light signals on the Fourier plane form corresponding bar codes or digital images, the respective codes on the microbeads being unintelligible as the corresponding bar code or the corresponding digital image.

11. A system according to claim 1, further comprising a detector configured to detect fluorescence from the microbeads.

12. A system according to claim 1, wherein the processor is configured to identify locations of the randomly distributed microbeads.

13. A system according to claim 1, wherein the processor identifies respective substances that are associated with the microbeads based upon the code.

14. A system according to claim 1, wherein the processor includes one or more microprocessor-based architectures.

15. An optical system comprising:
microbeads that are structurally distinct and capable of moving independently with respect to one another, the microbeads being encoded and configured to provide output light signals onto a Fourier plane when illuminated by an incident light;
an input light source configured to illuminate the microbeads thereby providing the output light signals, the output light signals configured to be projected onto the Fourier plane in a readable manner;
a reading device positioned to detect the output light signals from the Fourier plane; and
a processor configured to perform Fourier plane analysis of the optical light signals to determine corresponding codes of the microbeads, wherein the processor identifies chemical probes immobilized to the microbeads based upon the code.

16. A method for reading encoded microbeads, comprising:
- providing a plurality of microbeads having individually identifiable codes, the microbeads being structurally distinct and capable of moving independently with respect to one another, the microbeads being provided onto a support substrate and randomly distributed along the support substrate;
- illuminating the microbeads with an incident light, the codes providing corresponding output light signals indicative of the respective codes, the corresponding output light signals of the microbeads being projected on a Fourier plane; and
- reading the respective codes from the Fourier plane.

17. A method according to claim 16, wherein the output light signals are projected on the Fourier plane by scattering the incident light off or through the microbeads.

18. A method according to claim 16, wherein each of the codes comprises a variation in at least one of an effective refractive index or optical absorption of the respective microbead.

19. A method according to claim 18, wherein the variation in at least one of the effective refractive index or optical absorption is located within an inner region that is surrounded by an optically transparent outer region.

20. A method according to claim 16, further comprising identifying the microbeads by looking at a presence or absence of predetermined Fourier spatial frequencies.

21. A method for reading encoded microbeads, comprising:
- providing a plurality of microbeads having individually identifiable codes;
- illuminating the microbeads with an incident light, the codes providing corresponding output light signals indicative of the respective codes, the corresponding output light signals of the microbeads being projected on a Fourier plane; and
- reading the respective codes from the Fourier plane, wherein the codes of the microbeads are correlated to chemical probes that are immobilized to the microbeads, the method further comprising identifying the chemical probe using the code.

22. A method according to claim 21, further comprising determining whether the chemical probes have selectively bound to a target analyte after the microbeads are exposed to the target analyte.

* * * * *